US012573503B2

(12) United States Patent
Ishikawa et al.

(10) Patent No.: US 12,573,503 B2
(45) Date of Patent: Mar. 10, 2026

(54) INFORMATION PROCESSING DEVICE AND INFORMATION PROCESSING METHOD

(71) Applicant: PARAMOUNT BED CO., LTD., Tokyo (JP)

(72) Inventors: Takashi Ishikawa, Tokyo (JP); Yuuki Nakamura, Tokyo (JP); Yutaka Imada, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 163 days.

(21) Appl. No.: 18/225,432

(22) Filed: Jul. 24, 2023

(65) Prior Publication Data

US 2024/0127946 A1    Apr. 18, 2024

(30) Foreign Application Priority Data

Oct. 13, 2022    (JP) ................................. 2022-164923

(51) Int. Cl.
     *G16H 40/67*      (2018.01)
     *G16H 20/10*      (2018.01)
     *G16H 80/00*      (2018.01)

(52) U.S. Cl.
     CPC ............. *G16H 40/67* (2018.01); *G16H 20/10* (2018.01); *G16H 80/00* (2018.01)

(58) Field of Classification Search
     CPC ......... G16H 40/20; G16H 80/00; G16H 15/00
     See application file for complete search history.

(56) References Cited

U.S. PATENT DOCUMENTS

| | | | |
|---|---|---|---|
| 9,251,313 B2 | 2/2016 | Ross et al. | |
| 2018/0280243 A1* | 10/2018 | Velani | ................... A61J 7/0472 |
| 2019/0029588 A1* | 1/2019 | Weffers-Albu | .......... A61B 5/11 |
| 2019/0167181 A1* | 6/2019 | Jedwab | ................ A61B 5/4205 |

(Continued)

FOREIGN PATENT DOCUMENTS

WO    WO-2019079643 A1 *   4/2019     ........... A61B 5/0022

OTHER PUBLICATIONS

Forkan, Abdur Rahim Mohammad, and Ibrahim Khalil. "A clinical decision-making mechanism for context-aware and patient-specific remote monitoring systems using the correlations of multiple vital signs." Computer methods and programs in biomedicine 139 (2017): 1-16. (Year: 2017).*

*Primary Examiner* — Jason B Dunham
*Assistant Examiner* — Constantine Siozopoulos
(74) *Attorney, Agent, or Firm* — BIRCH, STEWART, KOLASCH & BIRCH, LLP

(57)          ABSTRACT

An information processing device of this embodiment includes a communication unit configured to communicates with a first terminal device and a second terminal device, the first terminal device being held by a medical caregiver, the second terminal device being held by a care assistant and a processing unit configured to acquire a medical information and a care assistance information, the medical information including a first method how to deal with a diagnosis of a patient taken by the medical caregiver, the care assistance including a second method how to deal with a status of the patient taken by the care assistant through the communication unit, wherein the processing unit is configured to provide the medical information and the care assistance information in association with the patient on the first terminal device and the second terminal device.

17 Claims, 29 Drawing Sheets

10

200A(200)

100

200B(200)

(56)        References Cited

U.S. PATENT DOCUMENTS

| 2019/0175093 | A1  | 6/2019 | Suzuki |  |
| 2020/0113435 | A1* | 4/2020 | Muhsin | ............... A61B 5/4833 |
| 2021/0029600 | A1  | 1/2021 | Balan et al. |  |

* cited by examiner

Figure 11:
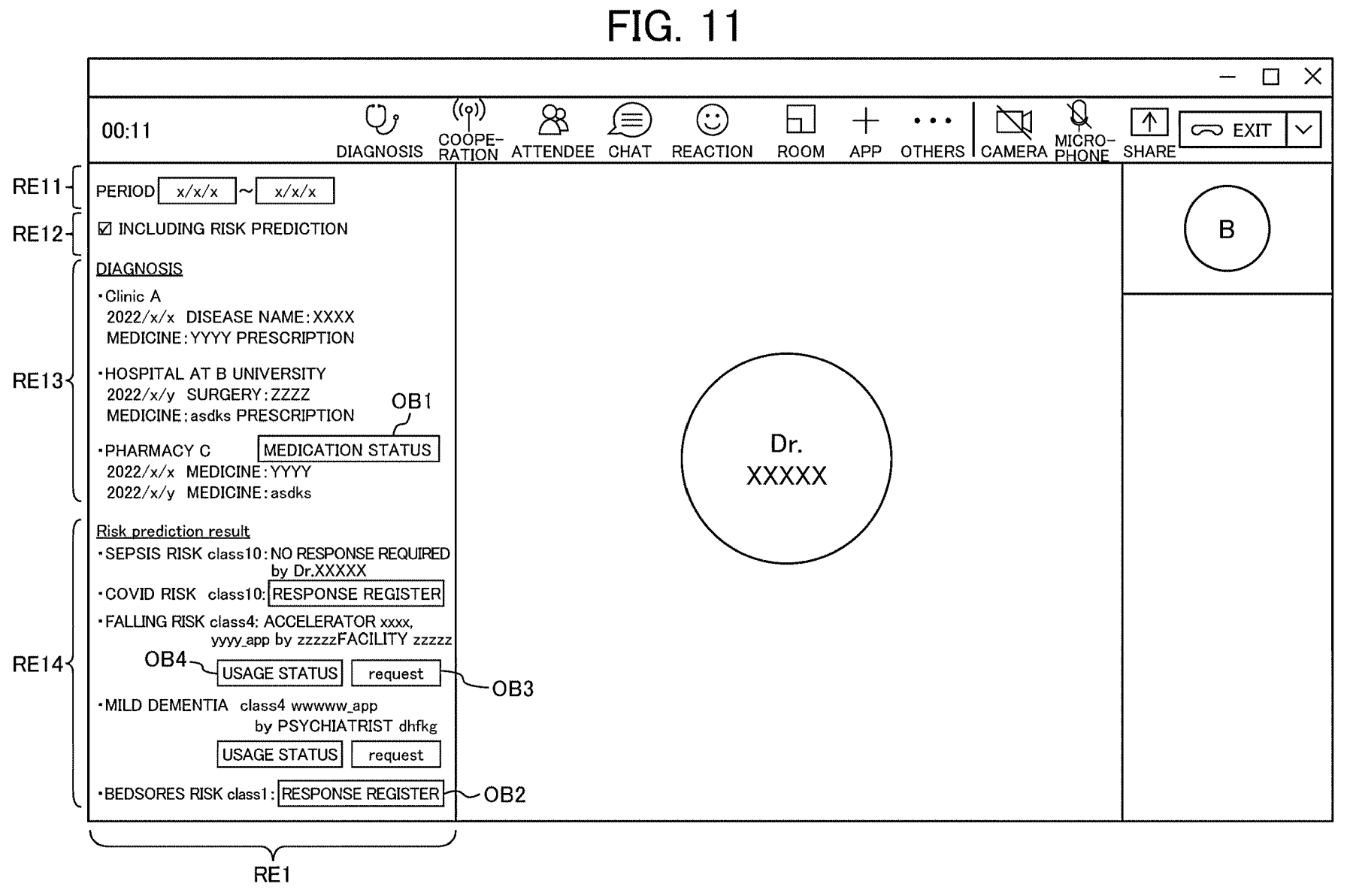

DIAGNOSIS   COOPE-RATION   ATTENDEE   CHAT   REACTION   ROOM   APP   OTHERS   CAMERA   MICRO-PHONE

↰ EXIT   SHARE

B

RE11 — PERIOD  x/x/x ~ x/x/x

RE12 — ☑ INCLUDING RISK PREDICTION

RE13 —
DIAGNOSIS
· Clinic A
  2022/x/x  DISEASE NAME:XXXX
  MEDICINE:YYYY PRESCRIPTION
· HOSPITAL AT B UNIVERSITY
  2022/x/y  SURGERY:ZZZZ
  MEDICINE:asdks PRESCRIPTION
· PHARMACY C      MEDICATION STATUS ← OB1
  2022/x/x  MEDICINE:YYYY
  2022/x/y  MEDICINE:asdks RE14 —
Risk prediction result
· SEPSIS RISK class10: NO RESPONSE REQUIRED
                       by Dr.XXXXX
· COVID RISK  class10: RESPONSE REGISTER
· FALLING RISK class4: ACCELERATOR xxxx,
       yyy.app by zzzzzFACILITY zzzzz
   OB4 — USAGE STATUS    request ← OB3
· MILD DEMENTIA  class4 wwwww.app
       www_app
       by PSYCHIATRIST dhfkg
       USAGE STATUS    request
· BEDSORES RISK class1: RESPONSE REGISTER ← OB2

RE1

Dr. XXXXX

BX        BC

BXs1

BXs2

FIG. 18B

| MEDICATION MANAGEMENT APPLICATION        —  □  ✕ | | | | | |
|---|---|---|---|---|---|
| RECORDING THE MOVIE | PLEASE PRESS THE BUTTON "RECORDING THE MOVIE" OR THE BUTTON "STORING THE RECORD" | | | | STORING THE RECORD |
| PERSON IN CHARGE | abc | USER | xyz | AT LUNCH BEFORE EATING MEAL | |
| MEDICINE ID | XYZ_AT LUNCH BEFORE EATING MEAL | | | DETER-MINATION | OK |

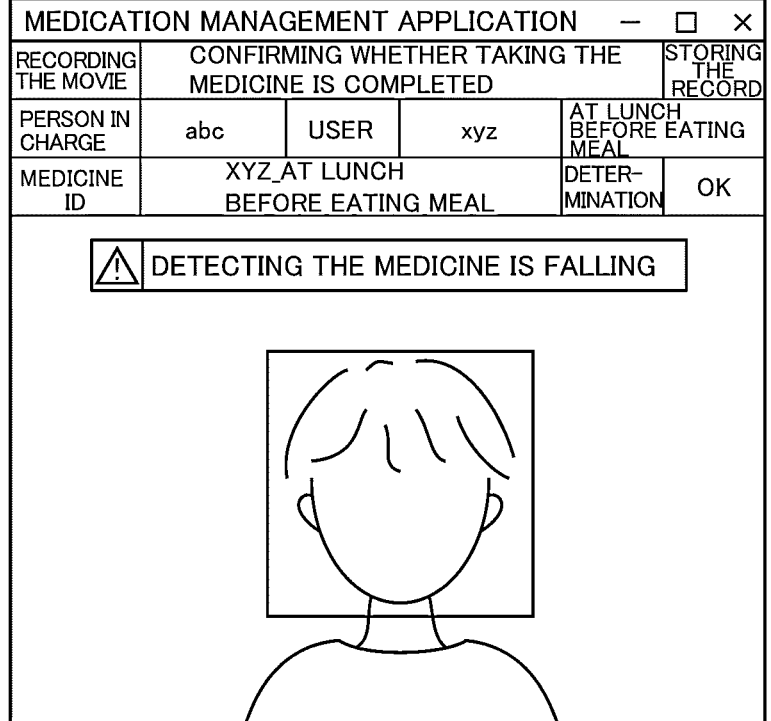

FIG. 19

| MEDICATION MANAGEMENT APPLICATION        —  □  ✕ | | | | | |
|---|---|---|---|---|---|
| RECORDING THE MOVIE | CONFIRMING WHETHER TAKING THE MEDICINE IS COMPLETED | | | | STORING THE RECORD |
| PERSON IN CHARGE | abc | USER | xyz | AT LUNCH BEFORE EATING MEAL | |
| MEDICINE ID | XYZ_AT LUNCH BEFORE EATING MEAL | | | DETER-MINATION | OK |

⚠ DETECTING THE MEDICINE IS FALLING

USAGE STATUS

USAGE STATUS

COOPERATION STATUS

USAGE STATUS WHEN COOPERATING
WITH THE SEAT SENSOR

INFORMATION PROCESSING DEVICE AND INFORMATION PROCESSING METHOD

CROSS-REFERENCE TO RELATED APPLICATIONS

This Non-provisional application claims priority under 35 U. S. C. § 119 (a) on Patent Application No. 2022-164923 filed in Japan on 13 Oct. 2022, the entire contents of which are hereby incorporated by reference.

BACKGROUND

1. Field

The present embodiment relates to the information processor and the information processing method, etc.

2. Description of the Related Art

Conventionally, there are known systems in medical care and assistance. For example, The U.S. Patent Publication No. 9251313 discloses a user interface for performing telemedicine and telemedicine. The U.S. Patent Application Publication No. 2021/029600 also discloses a method for predicting a patient's risk based on information such as electronic medical records.

BRIEF DESCRIPTION OF THE DRAWINGS

FIG. 11 is a screen example displayed on a first terminal device and a second terminal device.

FIG. 18B shows a screen example to display the results of the barcode recognition processing in medication management.

FIG. 19 shows a screen example to display a warning in medication management.

FIG. 20 shows a screen example to display a medication status.

FIG. 21 shows a screen example to display a usage status of a tacit knowledge.

FIG. 22 is a schematic diagram illustrating the experience processing of tacit knowledge in a virtual space.

DESCRIPTION OF THE PREFERRED EMBODIMENTS

Figure 1:
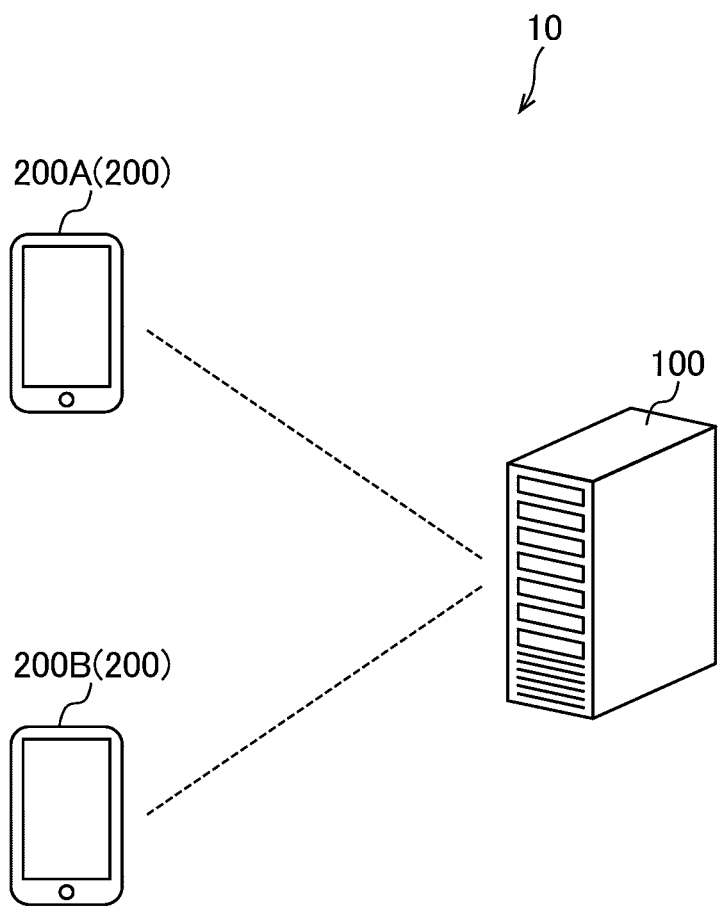
FIG. 1 shows a configuration example of the information processing system including an information processing device.

In general, one aspect of the present application is an information processing device including a communication unit configured to communicates with a first terminal device and a second terminal device, the first terminal device being held by a medical caregiver, the second terminal device being held by a care assistant and a processing unit configured to acquire a medical information and a care assistance information, the medical information including a first method how to deal with a diagnosis of a patient taken by the medical caregiver, the care assistance including a second method how to deal with a status of the patient taken by the care assistant through the communication unit, wherein the processing unit is configured to provide the medical information and the care assistance information in association with the patient on the first terminal device and the second terminal device.

Another aspect of the present application is an information processing method including acquiring a medical information from a first terminal device, the medical information including a first method how to deal with a diagnosis of a patient taken by a medical caregiver, acquiring a care assistance information from a second terminal device, the care assistance including a second method how to deal with a status of the patient taken by the care assistant, and providing the medical information and the care assistance information in association with the patient on the first terminal device and the second terminal device.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, computer-executable instructions, a program, and/or a computer. By way of illustration and not limitation, both an application running on a server and the server can be a component.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable (or machine-readable) device or computer-readable (or machine-readable) storage/communications media. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

The present embodiment will be described below with reference to the drawings. In the case of drawings, identical or equivalent elements shall be denoted by the same symbol, and duplicate descriptions shall be omitted. It should be noted that this embodiment described below does not unreasonably limit the contents of the claims. In addition, not all of the configurations described in this embodiment are essential components of this disclosure.

1. A System Configuration Example

The FIG. 1 shows a configuration example of the information processing system 10 including the information processing device according to this embodiment. The information processing system 10 includes, for example, a server system 100 and a terminal device 200. The terminal devices 200 may include, for example, a first terminal device 200A used by medical caregiver such as nurse in hospitals and a second terminal device 200B used by care assistant such as caregivers working in nursing facilities. In the following description, when it is not necessary to distinguish the multiple terminal devices from each other, the terminal device 200 is simply denoted.

The information processing system 10 according to the present embodiment shares information such as the measures taken by the medical caregiver or care assistant to the patient in, for example, the medical or care assistance (including nursing) scene. In the following description, when it is not necessary to distinguish the medical caregivers and care assistants from each other, the word "caregivers" is simply denoted. The medical caregivers include doctors, nurses, pharmacists, etc. The care assistants include care managers, qualified caregivers, visiting helpers, etc. In addition, in the method of this embodiment, occupational therapists and physical therapists may be included as medical caregivers or care assistants. For example, the information processing system 10 may anticipate a patient's risk (see U.S. Patent Application Publication No. 2021/029600 described above) and collect and present the actions taken by medical caregivers and care assistants to the patient in response to the patient's risk. According to the method of this embodiment, each specialist such as the doctor, the nurse, and the care manager can easily know the results of the actions taken by other specialists to a patient. Therefore, it is possible to avoid overlapping actions or to take actions that complement the actions taken by other specialists. As a result, it is possible to build a community comprehensive care system that comprehensively implements medical, nursing, and life support care in the community. In home care, the patient's family (family caregivers) may assist the patient. The caregivers in this embodiment corresponds to the caregivers with specialized tacit knowledge, a family caregiver may not be included in the caregiver in this embodiment. However, the method of the present embodiment is not limited to this, and the family caregiver may also become the caregiver in this embodiment.

As will be described later, the information processing system 10 according to the present embodiment may provide instructions to other medical caregivers or care assistants so that appropriate assistance can be provided without regard to proficiency by digitizing the "hunch" or "tacit knowledge" of the medical caregivers or care assistants in the medical facilities or the nursing facilities, for example. In this case, the information processing system 10 may perform processing for sharing information about the tacit knowledge used for the patient care among multiple specialists. The information processing system 10 may also include a third terminal device 200C or the like used by the developer of a tacit knowledge application or a tacit knowledge device 400, as described later with reference to FIG. 4, and transmit information about the usage status of the tacit knowledge or the like to the third terminal device 200C. Other specific aspects of the information processing system 10 of this embodiment can be modified in various ways. More details will follow.

The server system 100 shown in FIG. 1 is electrically or communicably connected to the first terminal device 200A and the second terminal device 200B via a network, for example. The network here is, for example, a public communication network such as the Internet. However, the network is not limited to the public communication network and may be a LAN (Local Area Network) or the like. For example, the server system 100 may communicate in accordance with the IEEE 802.11 standard. However, various modifications can be made to the communication method between the devices.

The server system 100 may be one server or include multiple servers. For example, the server system 100 may include a database server and an application server. The database server may store information transmitted from the terminal device 200 (in a narrow sense, the contents of the action taken for the patient). The application server performs various processing. The application server performs processing related to the server system 100 in, for example, FIGS. 10A and 10B, which will be described later. In addition, at least part of the processing performed by the terminal devices 200 in the following description and the tacit knowledge device 400 described later with reference to FIGS. 5 to 7, etc., may be performed by the application server. The multiple servers here may be physical servers or virtual servers. When virtual servers are used, the virtual servers may be provided on one physical server or distributed among multiple physical servers. As described above, the detailed configuration of the server system 100 in this embodiment can be modified in various ways.

The first terminal device 200A shown in FIG. 1 is a device used, for example, by doctors, nurses, pharmacists, etc., who are medical caregivers. Here, the first terminal device 200A is a mobile terminal device such as a smartphone or tablet device, for example. However, the terminal device 200 may be any other device such as a PC (Personal Computer), headset, wearable device such as AR (Augmented Reality) glass or MR (Mixed Reality) glass. One medical caregiver may also use multiple terminal devices 200. For example, a medical caregiver may use both a smartphone and a headset. The terminal device 200 in this embodiment may be a device carried by a medical caregiver, or the terminal device 200 may be a device installed at a prescribed location in the medical facility such as a hospital or pharmacy.

The second terminal device 200B shown in FIG. 1 is a device used by, for example, a care manager, a caregiver, etc., who are care assistants. The second terminal device 200B can be realized by various devices as well as the first terminal device 200A.

Figure 2:
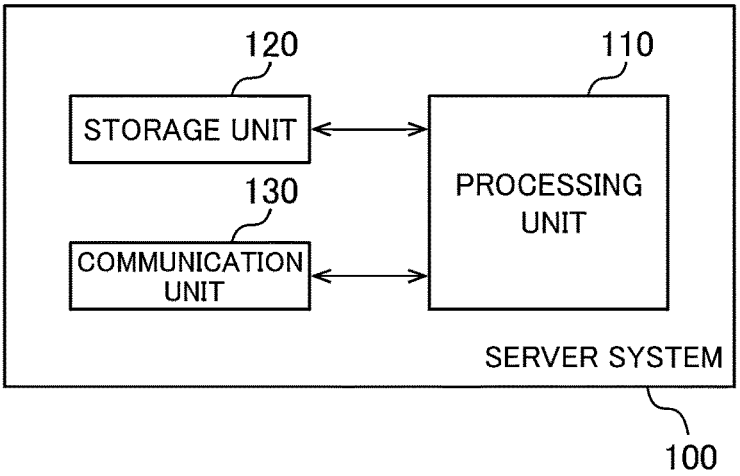
FIG. 2 shows a configuration example of a server system.

The FIG. 2 is a block diagram showing a detailed configuration example of the server system 100. The server system 100 includes, for example, a processing unit 110, a storage unit 120, and a communication unit 130. However, the configuration of server system 100 is not limited to FIG. 2, various modification such as some configurations may be omitted and others are added can be possible.

The processing unit 110 of this embodiment is composed of the following hardware. The hardware can include at least one of a circuit for processing digital signals and a circuit for processing analog signals. For example, the hardware can consist of one or more circuit devices mounted on a circuit board and one or more circuit elements. The one or more circuit devices can be, for example, integrated circuits (ICs), field-programmable gate arrays (FPGAs), etc. One or more circuit elements are, for example, resistors, capacitors, etc.

The processing unit 110 may be realized by the following processors. The server system 100 of this embodiment includes a memory for storing information and a processor operating based on the information stored in the memory. The information is, for example, a program and various kinds of data. The memory may be the storage unit 120 or other memory. The processor includes hardware. The processor can use various processors such as a CPU (Central Processing Unit), a GPU (Graphics Processing Unit), and a DSP (Digital Signal Processor). The memory can be a semiconductor memory such as an SRAM (Static Random Access Memory), a DRAM (Dynamic Random Access Memory), or a flash memory, or can be a register, a magnetic storage device such as a hard disk drive (HDD), or an optical storage device such as an optical disk device. For example, the memory stores instructions that can be read by a computer, and the processor executes the instructions to realize the functions of the processing unit 110 as processing. The instructions here can be instructions in the instruction set that make up the program, or instructions that instruct the processor's hardware circuits to operate.

The storage unit 120 is a work area of the processing unit 110 and stores various information. The storage unit 120 can be realized by various memories, and the memory may be a semiconductor memory such as SRAM, DRAM, ROM (Read Only Memory), or flash memory, a register, a magnetic storage device, or an optical storage device.

The communication unit 130 is an interface for communication through a network, and if the server system 100 performs wireless communication, the communication unit 130 includes, for example, an antenna, an RF (radio frequency) circuit, and a baseband circuit. However, the server system 100 may perform wired communication, and in this case, the communication unit 130 may include a communication interface such as an Ethernet connector and a control circuit of the communication interface. The communication unit 130 may operate the communication based on control signals from the processing unit 110 or may include a processor for communication control different from the processing unit 110. The communication unit 130 may operate the communication based on, for example, the scheme specified in IEEE 802.11 or IEEE 802.3 standard. However, various modifications can be made to the detailed communication scheme.

Figure 3:
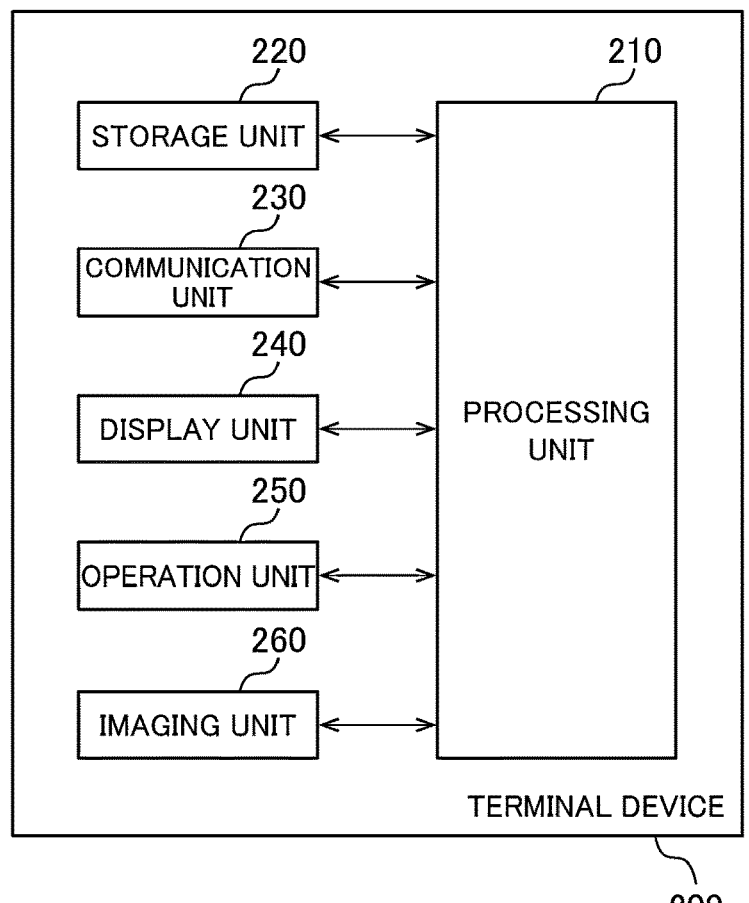
FIG. 3 shows a configuration example of a terminal device.

The FIG. 3 is a block diagram showing a detailed configuration example of the terminal device 200. The terminal device 200 may include, for example, a processing unit 210, a storage unit 220, a communication unit 230, a display unit 240, an operation unit 250, and an imaging unit 260. However, the configuration of the terminal device 200 is not limited to FIG. 3, and modifications such as omitting some configurations or adding others can be performed.

The processing unit 210 is composed of hardware including at least one of a circuit for processing digital signals and a circuit for processing analog signals. The processing unit 210 may also be realized by a processor. The processor can use various processors such as a CPU, GPU, DSP, etc. The function of the processing unit 210 is realized as processing by the processor executing instructions stored in the memory of the terminal device 200.

The storage unit 220 is the work area of the processing unit 210. The storage unit 220 is realized by various memories such as the SRAM, the DRAM and the ROM. The storage unit 220 may store information (medical information or care assistance information to be described later) input by caregivers such as medical caregivers or care assistants. The storage unit 220 may also store tacit knowledge applications to be described later (e.g., positioning applications).

The communication unit 230 is an interface for communication through a network and includes, for example, an antenna, an RF circuit, and a baseband circuit. The communication unit 230 communicates with a server system 100 through, for example, a network. The communication unit 230 may perform wireless communication in accordance with, for example, the IEEE 802.11 standard with the server system 100.

The display unit 240 is an interface for displaying various information and may be a liquid crystal display, an organic EL display, or a display of another type. The operation unit 250 is an interface for accepting user operations. The operation unit 250 may be a button or the like provided in the terminal device 200. In addition, the display unit 240 and the operation unit 250 may be a touch panel constructed as one unit.

The imaging unit 260 has an image sensor that can output image information by taking images in a predetermined range. The image information here may be a still image or a moving image. The image information may be color or monochrome. The imaging unit 260 may also include a depth sensor to detect the distance to the subject such as the patient or a sensor (e.g., an infrared sensor) to detect the heat of the subject such as the patient.

The terminal device 200 may also include some components which are not shown in FIG. 3. For example, the terminal device 200 may include various sensors that are, for example, a motion sensor such as an acceleration sensor, a gyro sensor, a pressure sensor, and a Global Positioning System (GPS) sensor, etc. The terminal device 200 may also include a light emitting unit, a vibration unit, a sound input unit, a sound output unit, etc. The light emitting unit is, for example, an LED (light emitting diode), which emits light. The vibration unit is, for example, a motor which can vibrate. The sound input unit is, for example, a microphone. The sound output unit is, for example, a speaker, and provides sound to notify the alarm or notifications. Moreover, the multiple terminal devices 200 are not limited to the same configuration. For example, the first terminal device 200A and the second terminal device 200B may have different configurations.

The information processing device of this embodiment may include a communication unit that communicates with the first terminal devices 200A used by medical caregivers and the second terminal devices 200B used by care assistants, and a processing unit that can perform processing based on information transmitted from the first terminal devices 200A and the second terminal devices 200B. For example, the communication unit of the information processing device may correspond to the communication unit 130 in FIG. 2, and the processing unit may correspond to the processing unit 110 in FIG. 2. However, the processing which should be executed by the information processing device in this embodiment may be realized by distributed processing of multiple devices, for example, by distributed processing between the server system 100 and the terminal devices 200. An example in which the information processing device is the server system 100 will be described below.

The processing unit 110 in the information processing device acquires medical information representing the results of the medical caregiver's handling of a prescribed patient and care assistance information representing the results of the care assistant's handling of the prescribed patient via the communication unit 130. Then, the processing unit 110 performs processing in the first terminal device 200A and the second terminal device 200B to present the medical information and care assistance information in association with the prescribed patient. For example, the processing unit 110 presents information including care assistance information in the first terminal device 200A used by the medical caregivers. The processing unit 110 presents information including medical information in the second terminal device 200B used by the care assistants. For example, the processing unit 110 may transmit the screen itself, which will be described later, to the first terminal device 200A using FIG. 11, or may transmit information for displaying the screen (e.g., markup language) to the first terminal device 200A. Moreover, the processing unit 110 performs processing to present information including medical information in the second terminal device 200B of the care assistants. As the result of this, the results of handling by other specialists can be presented to specialists in the field of medical care and assistance, that is medical caregivers and care assistants. Therefore, it is possible to achieve comprehensive care for the prescribed patient.

Figure 4:
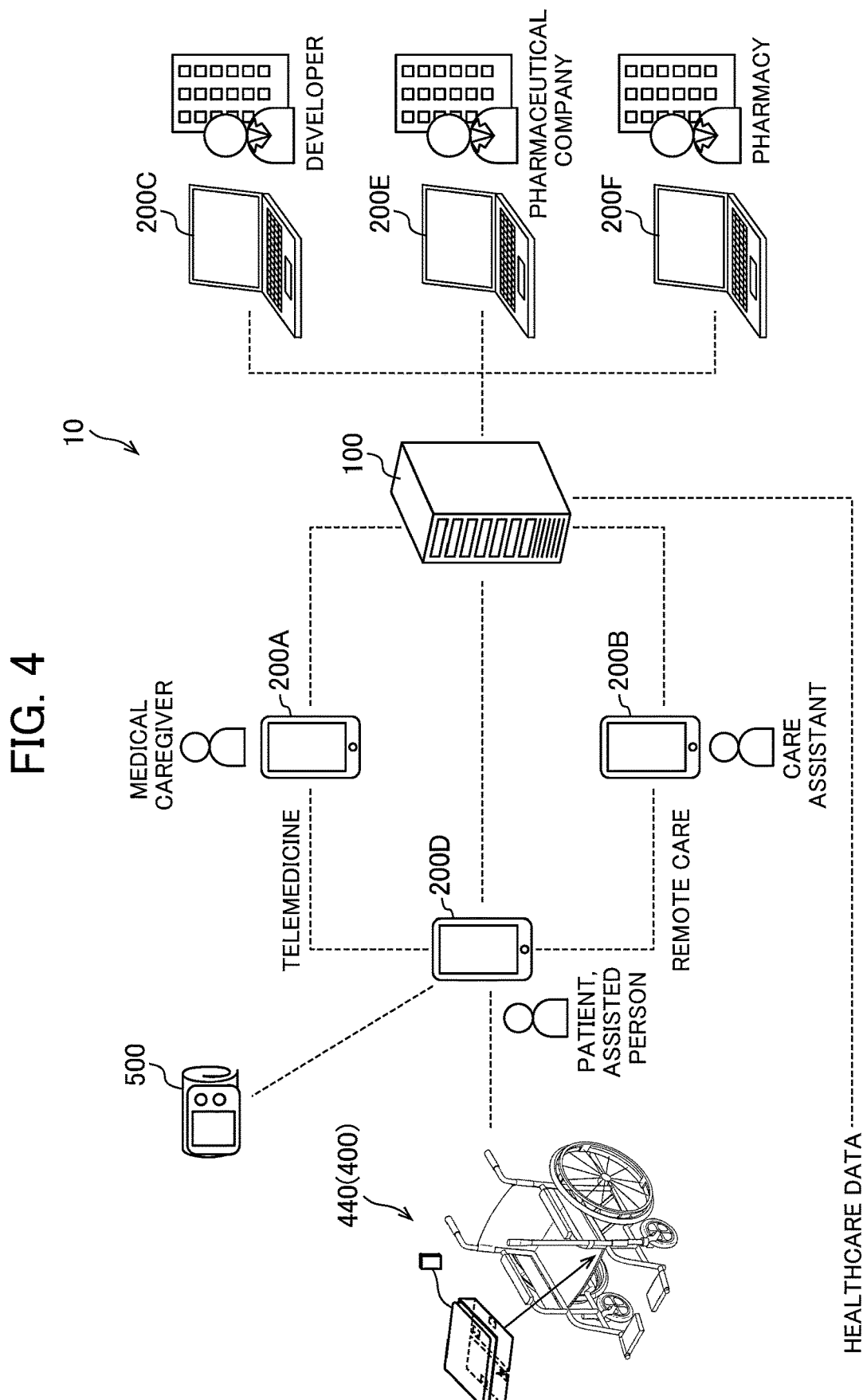
FIG. 4 shows a detailed configuration example of an information processing system.

Moreover, the information processing system 10 in this embodiment is not limited to the example in FIG. 1, and may include other components. The FIG. 4 is a diagram to explain other configuration examples in the information processing system 10. As shown in FIG. 4, the information processing system 10 may include a server system 100, a terminal device 200, a tacit knowledge device 400, and a device 500. The terminal device 200 may include a third terminal device 200C, a fourth terminal device 200D, a fifth terminal device 200E, and a sixth terminal device 200F in addition to the first terminal device 200A and the second terminal device 200B. The third terminal device 200C to the sixth terminal device 200F can be realized by various devices as well as the first terminal device 200A.

The fourth terminal device 200D shown in FIG. 4 is a terminal device 200 used by, for example, a patient to be diagnosed by medical caregivers or assisted person who is assisted by an caregivers such as care assistants. In the following, the patient or assisted person is simply referred to as a patient. The fourth terminal device 200D may also include a terminal device used by an assistant (e.g., a family of the patient) who assists the patient in home care. As shown in FIG. 4, a telemedicine (telemedicine) may be executed between the patient and the caregivers such as the medical caregivers, for example, by the first terminal device 200A and the fourth terminal device 200D. In addition, telemedicine may be executed between the patient and the caregivers such as the care assistants by the second terminal device 200B and the fourth terminal device 200D.

For example, the fourth terminal device 200D may be a device in which the tacit knowledge application can execute. The tacit knowledge application may perform processing according to the tacit knowledge of an expert in the field of the medical care or the care assistance. The tacit knowledge here is information that represents the results of determinations or detailed actions taken by an expert in the field of the medical care or the care assistance, for example. For example, the server system 100 may perform processing to digitize the tacit knowledge by performing machine learning based on a data set in which correct data given by a skilled caregiver are associated with input data. The correct data may include a correct answer data which the skilled caregiver allocates and an incorrect answer data which the skilled caregiver allocates. For example, the tacit knowledge corresponds to a learned model generated by machine learning. The input data may also be sensing data, for example, the output of a sensor provided around the patient or the output of a sensor attached on the patient. The tacit knowledge application acquires sensing data and outputs output data representing the determination of the expert and actions the expert may take by inputting the sensing data into a learned model. In addition, the tacit knowledge includes the correct answer data shown in FIG. 8A and FIG. 8B, and the tacit knowledge application may perform processing (for example, superimposing processing) to present the correct answer data along with the input data. The detailed examples of tacit knowledge will be described later using FIG. 5 to FIG. 9, etc.

In this way, the tacit knowledge of experts can be provided to patients and their families who are not specialists in medical care, nursing care, or care assistance, so that appropriate actions or determinations can be encouraged.

The tacit knowledge applications are not limited to those that operate in the fourth terminal device 200D, but may also operate in the first terminal device 200A or the second terminal device 200B. For example, it is possible to encourage appropriate actions or determinations regardless of the skill level by using the tacit knowledge of the skilled caregiver even if the caregivers don't have enough skill for the medical care, the nursing care, or the care assistance.

The tacit knowledge device 400 is a device that can perform processing in accordance with the tacit knowledge of a skilled caregiver in medical care, nursing care, or care assistance. The tacit knowledge here is similar to the example of the tacit knowledge application. In FIG. 4, a seat sensor 440 is exemplified as the tacit knowledge device 400, but the tacit knowledge device is not limited to this seat sensor 440, other devices can be the tacit knowledge device 400. For example, the tacit knowledge device 400 may include other devices such as a swallowing choke detection device 460 described later using FIG. 6, a bedside sensor 420, and a detection device 430 described later using FIG. 7.

For example, the tacit knowledge device 400 is placed around the patient or attached on the patient. For example, if the patient is a user who uses telemedicine or telemedicine services at home, the tacit knowledge device 400 may be placed in the patient's home. For example, the tacit knowledge device 400 may send the result (for example the sensing data itself, inputting data, determinations from the sensing data, recommended actions to be taken from the sensing data) according to the tacit knowledge to the fourth terminal device 200D used by the patient, and the fourth terminal device 200D may send the result to the server system 100. Alternatively, the tacit knowledge device 40 may be connected to the network and send the result to the server system 100 without connecting the fourth terminal device 200D.

In addition, the tacit knowledge device 400 may be located in the medical facilities such as hospitals, nursing facilities, home or the like. In this case, the result of the tacit knowledge device 400 may be transmitted to the server system 100 via the first terminal device 200A or the second terminal device 200B, or may be transmitted to the server system 100 via a management server or the like in the medical facilities or nursing facilities. Alternatively, the tacit knowledge device 400 may be connected to the network and the result may be transmitted to the server system 100 without connecting the first terminal device 200A or the like.

The device 500 in FIG. 4 is a device used for the patient and includes various devices that do not use the tacit knowledge. For example, a blood pressure meter is shown as the device 500 in FIG. 4, but the device 500 may include other devices such as an activity meter, a thermometer, etc. Also, the device 500 here may broadly include the devices placed in the patient's environment, such as a thermometer, a hygrometer, an illuminometer, etc.

By using the information processing system 10 shown in FIG. 4, it becomes possible to digitize and provide the tacit knowledge of skilled caregivers, and the server system 100 can collect and provide information about the tacit knowledge. Detailed examples of modes of using tacit knowledge will be described later with reference to FIG. 21 to FIG. 24, etc.

Also, as shown in FIG. 4, the information processing system 10 may include a third terminal device 200C used by developers of tacit knowledge applications and tacit knowledge devices 400. For example, the server system 100 may perform processing to cause the third terminal device 200C to present statistical data of usage of tacit knowledge devices developed by developers. Further, the server system 100 may perform processing to present an usage status of the tacit knowledge devices developed by developers, an usage status of other devices and applications to the third terminal device 200C. For details of information provided to developers will be described later in FIG. 26 to FIG. 29, etc. The other devices here may be other tacit knowledge devices 400 or devices 500 that do not use tacit knowledge.

Also, the server system 100 of this embodiment may collect the patient's health care information. The health care information here may be, for example, data in the electronic medical records (EMRs) or data in the personal health records (PHRs). The health care information may also include information acquired from tacit knowledge devices 400 or devices placed around the patient other than tacit knowledge devices 400. The health care information may also include the data acquired by the device 500 which is a wristwatch-type device that measures patient activity, etc.

And the server system 100 may predict the patient risk based on the health care information. The prediction result of the patient risk is output to the first terminal device 200A to the sixth terminal device 200F. Various techniques are known for method to predict the patient risk and output method to output the prediction result of the patient risk, such as those disclosed in U.S. Patent Application Publication No. 2021/029600, and they are widely applicable in this embodiment.

The server system 100 may also calculate an index representing a patient's ADL (Activities of Daily Living) based on information such as the health care information and output of the tacit knowledge applications or the tacit knowledge devices 400. The ADL here may be basic activities of daily living (BADL), instrumental activities of daily living (IADL), or both. Various indicators such as Barthel Index and DASC-21 are known as indicators of ADL, and either one of them or a different indicator may be used in this embodiment. The estimated ADL may be used if the tacit knowledge is used by the tacit knowledge devices, for example, as described later with reference to FIG. 24. Details will be discussed later.

The fifth terminal device 200E is a terminal device used, for example, by a pharmaceutical company. The server system 100 may collect information on, for example, the prescription status and medication status of a pharmaceutical company's product, and transmit the collected information to the fifth terminal device 200E. The server system 100 may also transmit the prediction result of the patient's risk along with this information to the fifth terminal device 200E.

The sixth terminal device 200F is a terminal device used, for example, in a pharmacy. The server system 100 acquires information about the medicine prescribed to the patient, for example, from the sixth terminal device 2000F, and performs processing to provide this information to other terminal devices 200. In FIG. 4, the sixth terminal device 200F is illustrated to indicate that the server system 100 can collect information from the pharmacy, but in view of the fact that the sixth terminal device 200F is used by pharmacists and equivalent medical caregivers, it may be considered that the sixth terminal device 200F is included in the terminal devices 200 used by medical caregivers.

As described above, in this embodiment, the server system 100 can (1) collect various types of information such as information from the terminal device 200, information from the tacit knowledge device 400, and other health care information, (2) perform various processes such as the risk prediction of the patient based on the collected information, and (3) provide the collected information and processing results such as the risk prediction of the patient to the terminal device 200, etc. At that time, the information processing system 10 of this embodiment can be used to provide comprehensive care appropriately, because the information processing system 10 can communicates the plurality of terminal devices 200 used by at least multiple caregivers including the medical caregivers and the care assistants.

In this embodiment, this information can be shared among multiple specialists (caregivers) by transmitting the information to each terminal device 200 as described above, but there are various possible methods to share the information. For example, the following information sharing methods may be considered.

Sharing information about patients that does not include results of an expert determination Sharing information including the medical information, the care assistance information which includes the results of expert determination the medical information may include the tacit knowledge.

the medical information may include responses to the risk of the patient and methods how to deal with the risk of the patient.

Sharing information on processing results using the tacit knowledge (e.g. through the tacit knowledge devices)

the information on medication status determined using the tacit knowledge (e.g. through the tacit knowledge devices)

the information on usage status of tacit knowledge (e.g. through the tacit knowledge devices)

The information that does not include results of an expert determination described above is, for example, patient attribute information or information sensed using devices 500 (the biological information of the patient, etc.). The medical information, the care assistance information which includes the results of expert determination is, for example, information representing medical diagnosis or care assistance results. In addition, the medical information or the like may include the tacit knowledge determined to be useful to the target patient. In addition, the medical information or the like may include information related to responses to the risk of the patient of the target patient or methods how to deal with the risk of the patient, as described later with reference to FIG. 11, etc. In addition, when the tacit knowledge is set to the tacit knowledge device for the target patient, the information representing the results of the usage state of the tacit knowledge may be also shared. The information here may include the results determined by the tacit knowledge device 400 or the tacit knowledge application. In addition, the results determined by the tacit knowledge may include information on the medication status and the usage status of the tacit knowledge, as described later with reference to FIGS. 20 and 21.

Some of the information shared here may also be used to input other information or to activate other devices. For example, the medical information or the like may be input to other device such as the server system 100 or the tacit knowledge devices by performing diagnose or the like based on patient attribute information or information from the device 500. If the information representing the medication prescription is input as the medical information to the server system 100, the medication management using the tacit knowledge device may be started. In addition, based on the results of medication status whether the patient take the medicine appropriately, the content of responses to the risks, such as changes in medication or restarting taking the same medicine, may be changed. In particular, in this embodiment, the information input by multiple specialists (caregivers) is shared, so that one specialist can use the information input by another specialist for his or her own determination what kinds of tacit knowledge should be used to the target patient. Therefore, collaboration across disciplines is facilitated, and as a result, comprehensive care can be adequately provided. Details of sharing information will be discussed later.

The information processing device of this embodiment is not limited to a system realized by the server system 100, and may be realized by any of the terminal devices 200 described above or a combination of two or more terminal devices 200. For example, the method of the present embodiment can be applied to terminal device 200, which includes an acquisition unit that acquires the medical information representing the results of medical caregiver's handling from the first terminal device 200A used by the medical caregivers, and acquires the care assistance information representing the results of the care assistant's handling from the second terminal device 200 B used by the care assistants, and the processing unit 210 configured to perform processing in the first terminal device 200A and the second terminal device 200B to make the medical information and the care assistance information present in association with the patient. The acquisition unit here may be a part of the processing unit 210, for example, or the communication unit 230.

Moreover, a part or all of the processing performed by the information processing system 10 of this embodiment may be realized by a program. In a narrow sense, the processing performed by the information processing system 10 is the processing performed by the processing unit 110 of the server system 100, but the processing may be the processing performed by the processing unit 210 of the terminal devices 200. In addition, the processing performed by the information processing system 10 may be the processing performed by the processor included in the tacit knowledge devices 400. The processing performed by the information processing system 10 may be the processing performed by two or more of the server system 100, the terminal devices 200 and the tacit knowledge devices 400.

The program according to this embodiment can be stored in, for example, a non-temporary information storage medium (information storage device) which is a computer-readable medium. The information storage media can be realized by, for example, optical disks, memory cards, HDDs, or semiconductor memories. The semiconductor memories are, for example, ROM. The processing unit 110 performs various processing of this embodiment based on a program stored in the information storage medium. That is, the information storage medium stores a program for making the computer function as the processing unit 110 or the like. A computer is a device equipped with an input device, a processing unit, a storage unit and an output unit. Specifically, the program according to this embodiment is a program for making a computer execute each step described later with reference to FIG. 10A, and FIG. 10 B, etc.

Also, the method of this embodiment can be applied to an information processing method including each step described below. The information processing method includes a step of acquiring medical information representing the results of medical caregiver's handling of a given patient from a first terminal device 200A used by the medical caregivers, a step of acquiring the result of the care assistance information representing the results of the care assistant's handling of the patient from a second terminal device 200B used by the care assistants, and a step of performing processing to present the medical information and the care assistance information in association with the patient in the first terminal device 200A and the second terminal device 200B.

2. Devices and Applications Related to Tacit Knowledge

Next, a detailed example of a tacit knowledge device 400 and a tacit knowledge application related to this embodiment will be described.

2.1 The Seat Sensor

Figure 5:
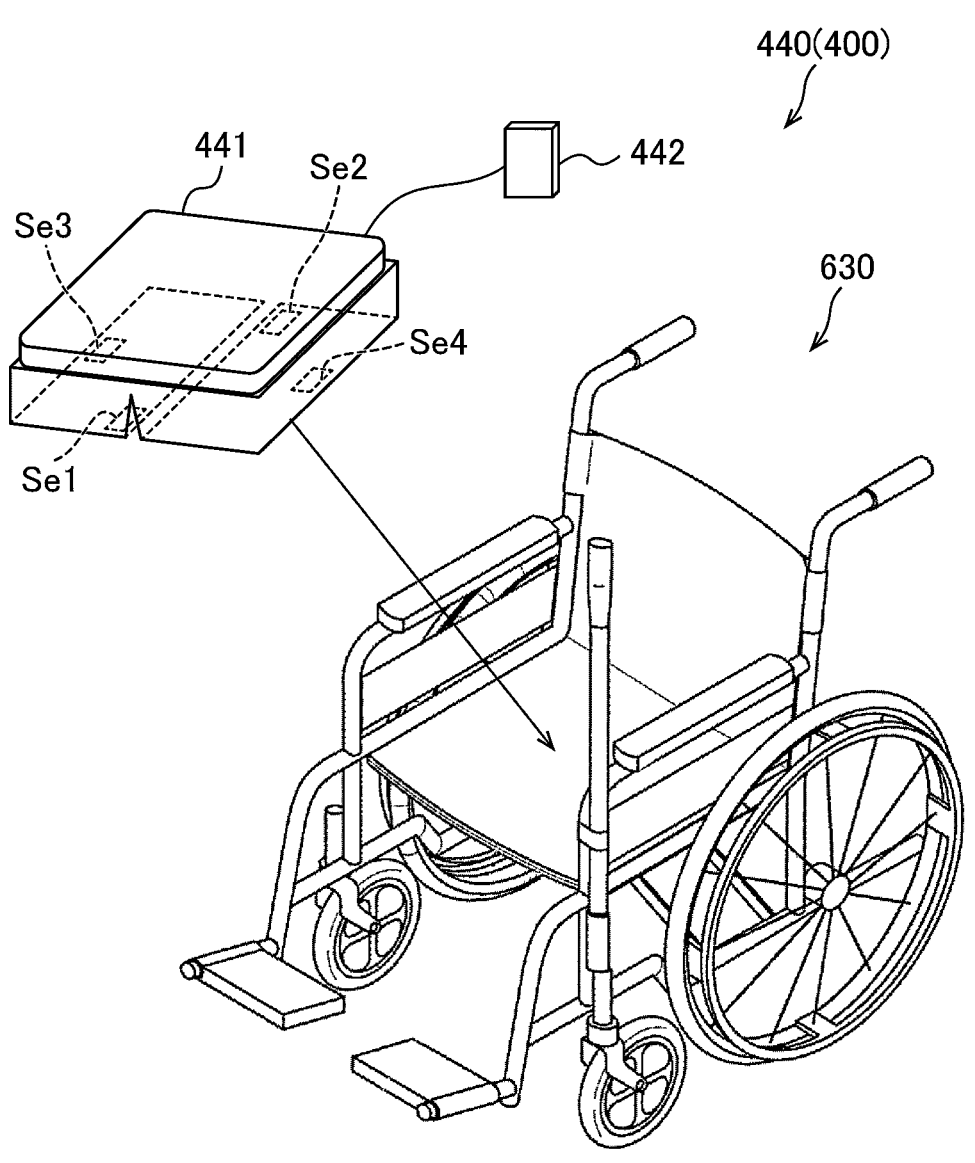
FIG. 5 shows a configuration example of a seating sensor.

The FIG. 5 is an example of the tacit knowledge device 400, for example, a diagram showing the seat sensor 440 placed on the seat surface of a wheelchair 630. The seat sensor 440 includes a pressure sensor that outputs a pressure value and the seat sensor 440 will outputs the pressure value if the patient sits the wheelchair 630. The seat sensor 440 may include a plurality of pressure sensors to detect a pressure distribution from the outputs of the pressure sensors.

For example, the seat sensor 440 may determine, based on the pressure value of the pressure sensor or the pressure distribution of the pressure sensors, whether the patient's posture when sitting in the wheelchair 630 (Hereafter, it is also described as a sitting posture) is normal (a balanced posture), a forward tilted posture, left or right side tilted posture, or any of several other postures. The forward tilted posture refers to a posture in which the center of gravity of the patient is shifted forward more than usual, and side tilted posture refers to a posture in which the center of gravity of the patient is shifted to either the left or right more than usual. Both forward tilted posture and left or right side tilted posture correspond to a posture in which the risk of falling from the seat surface is relatively high, and the seat sensor 440 may determine the risk possibility of falling to determine whether the patient falls from the seat surface.

However, the amount tilted from the normal posture (a balanced posture) which the patients have the falling risks in care assistance, etc. depends on the attributes of the patients. Even if two patients had tilted a first amount from the normal posture, a first patient may not have any falling risk and a second patient may have falling risk. The attributes of the patients here include sex, age, height, weight, medical history, ADL, etc. Therefore, the tacit knowledge of the specialist regarding the sitting posture may be digitized by providing the correct data with the pressure value or the pressure distribution from the specialist. For example, the specialist may allocate, to the correct data, the determination result regarding the normal posture, the forward tilted posture, the left or right side tilted posture. That is a first determination result may be allocated to a correct answer data which the specialist think the patients have highly risk for falling, a second determination result may be allocated to a wrong answer data which the specialist think the patients have relatively low risk for falling. Alternatively the specialist may allocate, to the correct data, the time-series data of the pressure value mapped on a two-dimensional plane or pressure distribution (e.g., the time-series change of the center of gravity position). The server system 100 performs machine learning using the data combining the pressure value or the pressure distribution and the correct data as training data to output a learned model (software) that discriminates the normal posture, the forward tilted posture, and the left or right side tilted posture based on the pressure value or the pressure distribution. The seat sensor 440 performs the processing according to the tacit knowledge by operating according to the learned model.

In the example of FIG. 5, four pressure sensors Se1 to Se4 are arranged on the back side of a cushion 441 which is arranged on the seat surface of the wheelchair 630. The pressure sensor Se1 is a sensor arranged forward compared to the pressure sensor Se2, The pressure sensor Se2 is a sensor arranged backward compared to the pressure sensor Se1, the pressure sensor Se3 is a sensor arranged to the right, and the pressure sensor Se4 is a sensor arranged to the left. Here, the forward, backward, left, and right represent the direction as seen from the patient when the patient is seated in the wheelchair 630.

As shown in FIG. 5, the pressure sensors Se1 to Se4 are electrically connected or capable of communicating to a control unit 442. The control unit 442 includes a processor for controlling the pressure sensors Se1 to Se4 and a memory configured to serves as the work area of the processor. The processor detects the pressure value by operating the pressure sensors Se1 to Se4.

The patients sitting in the wheelchairs 630 may experience pain in the buttocks and change the posture to displace the buttocks. For example, a posture of the patient in which the buttocks are displaced more forward than usual is the forward tilted posture, and a posture of the patient in which the buttocks are displaced laterally to the right side or the left side is the left of right side tilted posture. Also, the forward tilted posture, and the left of right side tilted posture may occur simultaneously, and the center of gravity of the patient may shift obliquely. The seat sensor 440 can appropriately detect whether the posture of the patient is the forward tilted posture, or the left of right side tilted posture by detecting a change in the position of the buttocks using a pressure sensor arranged on the cushion 441 as shown in FIG. 5. For example, the seat sensor 440 determines the forward tilted posture if the value of the pressure sensor Se1 increases by more than a prescribed amount compared to the initial state, and determines the left of right side tilted posture when the value of the pressure sensor Se3 or Se4 increases by more than a prescribed amount compared to the initial state. For example, the tacit knowledge of the specialist may be a threshold to determine the forward tilted posture or the left of right side tilted posture.

Also, the seat sensor 440 senses the pressure values of the pressure sensors Se1 to Se4 and outputs the pressure values of the pressure sensors Se1 to Se4 to the server system 100. The data should be output to the server system 100 as the sensing data may include the determination results whether the posture of the patient is normal, the forward tilted posture, or the left of right side tilted posture, the determination results or evaluation results of the possibility of falling, etc. The control unit 442 may include a light emitting unit and the light emitting unit may be used to inform or notify an alarm that the posture of the patient is not normal to the caregivers. As the result of this, the caregivers can easily understand the change of the sitting posture of the patient in the wheelchair 630 by notifying the alarm, so that the falling of the patient can be suppressed.

2.2 Swallowing Choke Detection Device

Figure 6:
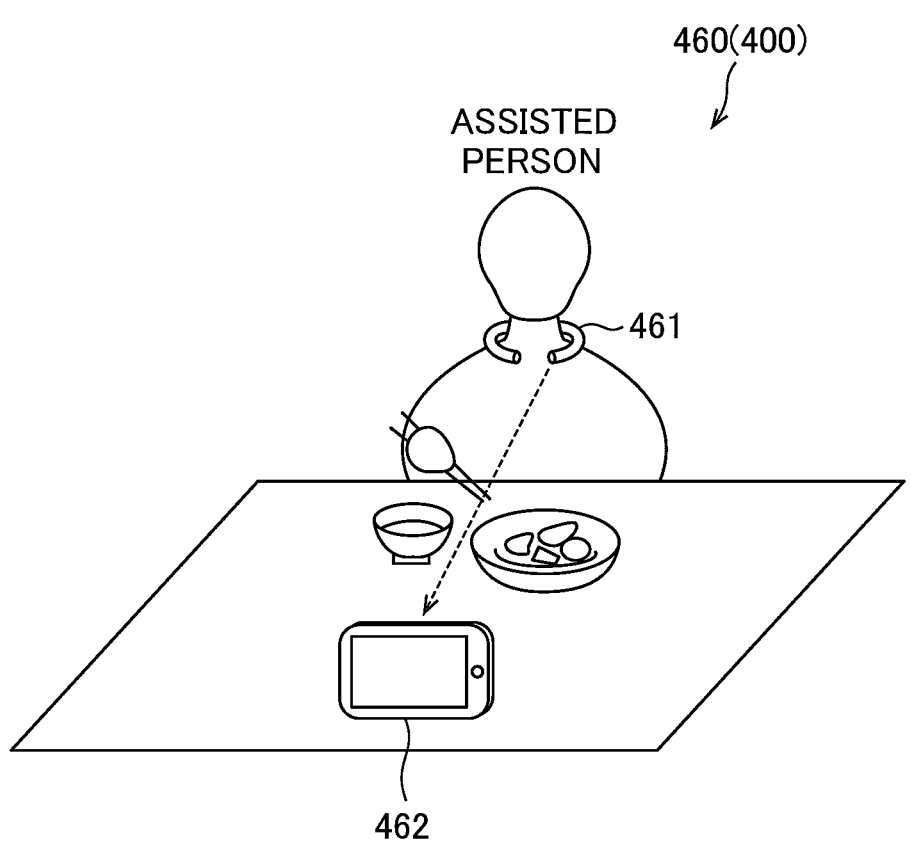
FIG. 6 shows a configuration example of a swallowing choke detector.

The FIG. 6 is one example of the tacit knowledge device 400, and is a diagram illustrating a swallowing choke detection device 460 used in a meal care assistance. As shown in FIG. 6, the swallowing choke detection device 460 includes a throat microphone 461 which the patient can wear around the patient's neck and a terminal device 462 with a camera.

The throat microphone 461 outputs audio data from swallowing, coughing, etc. of the patient. The camera of the terminal device 462 outputs an image of the patient's eating. The terminal device 462 is, for example, a smartphone or tablet-shaped PC placed on a table where the patient eats. The throat microphone 461 is electrically connected or communicable to the terminal device 462 using Bluetooth® or the like, and the terminal device 462 is electrically connected or communicable to the server system 100 through a network. However, the terminal device 462 may be electrically connected or communicable to the server system 100 through the second terminal device 200*b* or the fourth terminal device 200*d*, or both the throat microphone 461 and the terminal device 462 may be directly connected to the server system 100, and the detailed connection mode can be implemented in various variations.

For example, the swallowing choke detection device 460 determines whether there is a patient's choke and swallowing based on the audio data of the throat microphone 461. A device for detecting swallowing using a microphone which the patient wear around the patient's neck is described in, for example, "Swallowing action measurement device and swallowing action support system" U.S. patent application Ser. No. 16/276,768, filed Feb. 15, 2019. This patent application is incorporated by reference herein in its entirety. Based on the audio data, the processor can detect the number of choking, the time of choking (Time of occurrence, duration, etc.), and whether or not the patient swallows.

The camera in the terminal device 462 can detect the patient's mouth, eyes, and objects such as chopsticks, spoons, etc. which the patient uses by imaging the patient from the front direction as shown in, for example, FIG. 6. Various methods for detecting these facial recognition and objects based on image processing are known, and the known methods can be widely applied in this embodiment.

For example, a skilled caregiver such as the specialist may determine various kinds of things described below based on the audio data of the throat microphone 461 (for example, waveform data representing audio) and the image captured by the camera in the terminal device 462, and input determination result as the correct data (including the correct answer data and the wrong answer data). The server system 100 generates the learned model by performing machine learning based on a data set in which both the audio data, the captured image and the correct data are associated. The swallowing choke detection device 460 may realize processing according to the tacit knowledge by executing each of the following processing based on the learned model.

For example, the swallowing choke detection device 460 can determine whether or not the patient's mouth is open, whether or not the meal or food is out of the patient's mouth, and whether or not the patient is biting the meal or food based on the captured image of the camera. The swallowing choke detection device 460 can also determine whether or not the patient's eyes are open based on the captured image. The swallowing choke detection device 460 can also determine whether or not the objects such as chopsticks, spoons, etc. are near the tableware, whether or not the patient is holding the objects, and whether or not the meal or food is spilled based on the captured image.

In this method, based on this information, the swallowing choke detection device 460 may estimate the patient's situation in the meal regarding whether the patient is swallowing, choking, or other situations. For example, the swallowing choke detection device 460 may request information about meals based on the detection results of swallowing or choking and the detection results whether the patient's mouth is open or not.

For example, the swallowing choke detection device 460 may determine whether the patient is choking frequently based on the number of times and the time of choking and output the results whether the patient is choking frequently. For example, the swallowing choke detection device 460 may determine that patient is choking frequently if the number of times of choking per unit time exceeds a threshold.

The swallowing choke detection device 460 may also determine the swallowing time from the timing the patient closes his or her mouth to the timing the patient swallows, based on the results of whether the patient is swallowing and the results of whether the patient's mouth is open or not. In this way, for example, if the number of swallowing is decreasing compared to previous meal, a detailed situation can be determined, such as whether the action of putting food into the mouth itself is not being performed or whether the patient is not swallowing even after putting food into his or her mouth. For example, the swallowing choke detection device 460 may start counting up the timer when the mouth moves from an open state to a closed state based on the captured image of the terminal device 462 and stop counting up the timer when the swallowing choke detection device 460 detects that the patient is swallowing by the throat microphone 461. The period during counting up the timer represents the swallowing time. In this way, it is possible to accurately determine if there is a high risk of aspiration in eating a meal or food and if there is a situation in which the caregiver should perform some action.

In addition, the swallowing choke detection device 460 may determine the eating pace of meals based on the swallowing time. The swallowing choke detection device 460 may also determine whether swallowing time is relatively long or not based on changes in the swallowing time in a single meal (e.g., increase amount or ratio to swallowing time compared to when the patient starts eating, etc.) or the processor may calculate, for the same patient, the average swallowing time, etc. in each of the multiple meals and determine whether the swallowing time of the patient has increased or not based on the changes in the average swallowing time of the patient.

In addition, the swallowing choke detection device 460 can determine whether the patient is in a situation where he or she is unable to open the mouth even when the caregiver takes the spoon to the patient, etc., by using the results of whether the patient's mouth is open or not based on the captured image of the terminal device 462. Thus, in a situation where the patient is reluctant to open the mouth, if the swallowing time is prolonged, the swallowing choke detection device 460 can estimate that a situation where the food remains in the mouth occurs. The swallowing choke detection device 460 can also determine whether the patient has been unable to chew food by using the results of recognition of whether food is getting out of the patient's mouth or whether the patient is chewing food using the captured images. For example, if the number of chewing is normal but the swallowing time is relatively long, the swallowing choke detection device 460 presumes that the patient has been unable to chew food. In addition, if the swallowing choke detection device 460 detects the patient's eyes are closed using the captured images, the swallowing choke detection device 460 presumes the patient is drowsy or sleeping.

In addition, the swallowing choke detection device 460 can determine whether the situation is such as playing with food, not being able to hold a bowl, or not doing anything by performing object recognition processing (object detection processing) of chopsticks, spoons, etc., using the captured image. For example, if an object such as the spoon overlaps the hand of a patient, but the period until the patient take the object (spoon) to his or her mouth is equal to or greater than a predetermined threshold, the swallowing choke detection device 460 can determine that the patient cannot hold a bowl or is playing with food. Also, if an object such as the spoon does not overlap the hand of a patient, and the period when the patient's gaze is directed to food (cooking) is equal to or greater than a predetermined threshold, the swallowing choke detection device 460 can determine that the patient is watching food without doing anything.

In addition, the swallowing choke detection device 460 may determine the swallowing ability of a patient based on the number and frequency of choking, the severity of choking, the change in swallowing time, etc. determined by the method described above.

In addition, the swallowing choke detection device 460 determines the occurrence timing of swallowing and the amount of swallowing based on the audio data detected by the throat microphone 461, and the feature amount of the audio data may vary according to various situations. The feature amount here may be the amplitude in the waveform of the audio data, the frequency, or the wave number included in one swallowing. For example, the audio data of swallowing may vary depending on factors such as the consistency and thickness of the food and the pace of eating the meal. In addition, it has been found that the audio data of swallowing changes based on the patient's physical condition, even if the consistency of the food is the same. Therefore, the swallowing choke detection device 460 may obtain a feature quantity representing the audio data of swallowing based on the output of the throat microphone 461 and estimate the patient's physical condition based on the feature quantity.

In addition, the swallowing choke detection device 460 of this embodiment may be used for patient medication management as described later with reference to FIGS. 17 to 19. Details of medication management will be described later.

2.3 Bedside Sensors and Detectors

Figure 7:
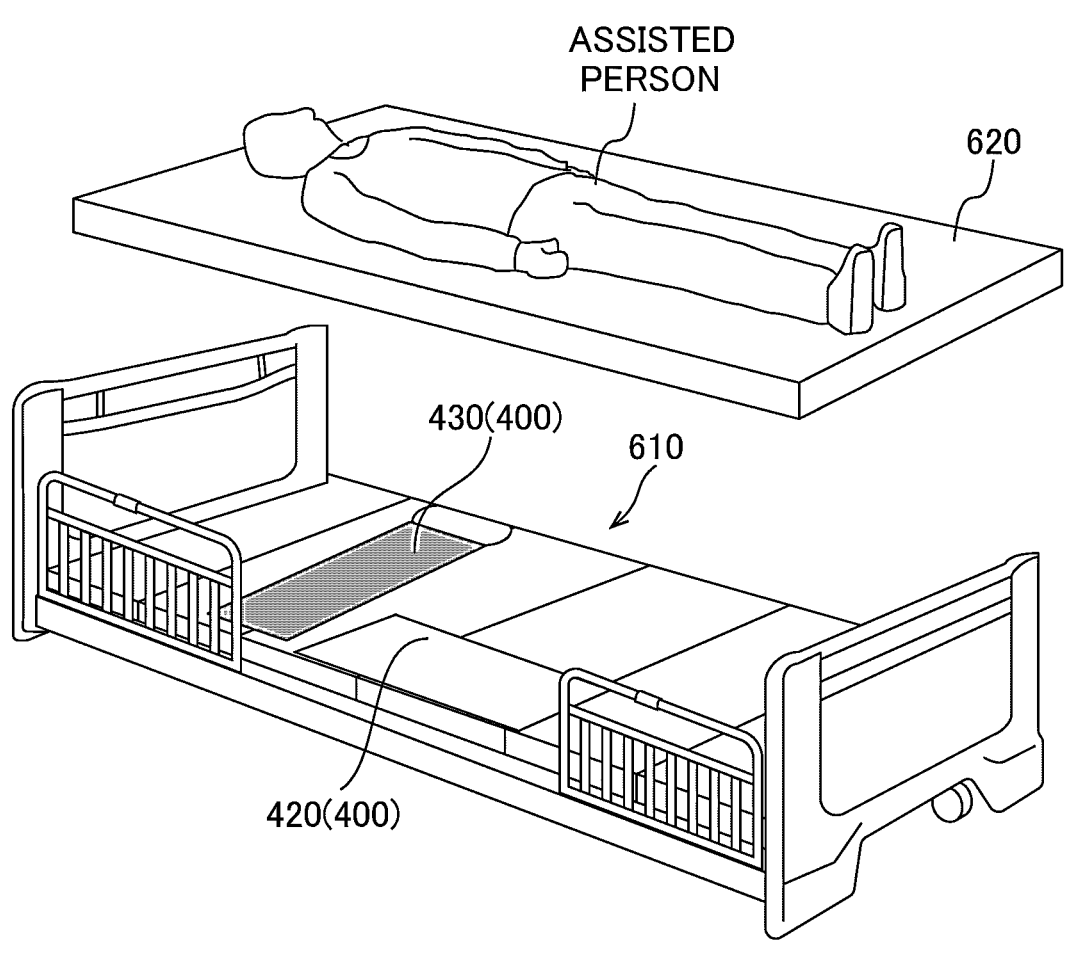
FIG. 7 shows a configuration example of a bedside sensor and detector.

The FIG. 7 is a diagram illustrating an example of the tacit knowledge device 400, which is the bedside sensor 420 and a detection device 430 arranged on the sections of a bed 610. The bedside sensor 420 and the detection device 430 are sheet-type or plate-type devices arranged between the sections of the bed 610 and a mattress 620, for example, as shown in FIG. 7. The bed 610 includes a plurality of sections and the bed 610 can move each section to raise up a height of the bed 610, to tilt the bed or to raise or lower the section corresponding to the back part or leg part.

The bedside sensor 420 includes a pressure sensor that outputs a pressure value, and is arranged on the side of the section that the patient uses to get into or get out of the bed 610. In the example of FIG. 7, the bedside sensor 420 is arranged on the front side of the bed 610. At this time, as shown in FIG. 7, a fall prevention fence is arranged on the front side of the bed 610, and the bedside sensor 420 may be arranged in a position where the fence is not provided. In this way, the patient who gets into and gets out of the bed 610 once performs the sitting action on the bedside sensor 420. The bedside sensor 420 may output time-series pressure data to the server system 100 as the sensing data. Alternatively, the bedside sensor 420 may determine whether the patient starts action by executing the processing described below and output the determination result to the server system 100 as the sensing data. For example, the server system 100 generates a learned model by performing machine learning on the input data, which is a pressure value, based on the training data to which the result of the skilled caregiver's determination is given as the correct data. The bedside sensor 420 performs the following processing by inputting a pressure value into the learned model.

The bedside sensors 420 perform processing to determine the patient's movement on the bed 610, for example, from pressure values. For example, if the patient stands up from the bed 610, it is assumed that the patient moves from a supine position on the bed to a sitting position on the bedside (Below, it is described as sitting posture), and then performs the standing up action by applying force to the section surface. The pressure value detected by the bedside sensor 420 may increase in the order of lying down, sitting down, and standing up action. For example, the bedside sensor 420 may determine that the patient starting the action when a change from sitting down to standing up action is detected based on a comparison process between the pressure value and a given threshold. Alternatively, in terms of detecting the standing up action at a faster stage, the bedside sensor 420 may determine that the patient starting the action when a change from lying down to sitting down is detected based on a comparison process between the pressure value and a given threshold.

Alternatively, when the patient continues the standing up action, the patient's buttocks may rise from the surface of the section, so the pressure value output from the pressure sensor is greatly reduced. Therefore, the bedside sensor 420 may determine that the patient starts the standing up action when the pressure value increases above the first threshold and then decreases below the second threshold, which is smaller than the first threshold, based on the time series change of the pressure value. In addition, various modifications can be made to the detailed processing content of the starting action determination.

The detection device 430 shown in FIG. 7 is a device configured to sense information about whether the patient is sleeping or not. The detection device 430 includes a pressure sensor (e.g., a pneumatic sensor) configured to output a pressure value. For example, the server system 100 generates a learned model by performing machine learning on input data, which is a pressure value, based on training data in which the result of the skilled caregiver's determination is given as the correct data. The detection device 430 generates a learned model by inputting a pressure value into the learned model.

The detection device 430 detects body vibration (body movement and vibration) of the patient via the mattress 620 if the patient is in the bed 610. The detection device 430 may calculate any information about the respiration rate of the patient, the heart rate of the patient, the amount of activity of the patient, the posture of the patient, whether the patient is awake or sleeping, and whether the patient is staying or getting out of the bed 610 based on the body vibrations detected by the detection device 430. The detection device 430 may also determine whether the patient is a non-REM sleep state and a REM sleep state and determine the depth of sleeping of the patient. For example, the detection device 430 may analyze the periodicity of body movement, and the respiratory rate of the patient and the heart rate of the patient may be calculated from the peak frequency. The analysis of the periodicity may be, for example, Fourier transform. The respiratory rate of the patient is the number of breaths per unit time. The heart rate of the patient is the number of heartbeats per unit time. The unit time is, for example, one minute. In addition, the detection device 430 may calculate the number of detected body vibrations during a sampling unit time as the amount of activity. In addition, since the detected pressure value will decreases if the patient is standing on the floor compared to when the patient is staying in the bed 610, it is possible to determine whether the patient is in the bed 610 based on the pressure value and its time-series change of the pressure value.

For example, the detection device 430 may output the data acquired from the pressure sensor to the server system 100 as the sensing data. Alternatively, the detection device 430 may output the information about the respiration rate of the patient, the heart rate of the patient, the amount of activity of the patient, the posture of the patient, whether the patient is awake or sleeping, and whether the patient is staying or getting out of the bed 610 to the server system 100 as the sensing data.

The detection device 430 may also determine whether the patient starts moving from for example the bed 610. For example, the detection device 430 may determine that the patient has started moving if the patient is getting out of the bed. Alternatively the detection device 430 may determine that the patient has started moving if the patient is awake from a state that the patient is sleeping under the viewpoint to detect starting moving at an earlier stage. The detection device 430 may output the results whether the patient starts moving as the sensing data to the server system 100.

2.4 Positioning Application

In this embodiment, the positioning application used to adjust the posture of the patient may be used as the tacit knowledge application. The positioning application may be operated or executed in a fourth terminal device 200D used by a patient or his or her family described below, but the positioning application may be operated or executed in other devices such as the first terminal device 200A or the second terminal device 200B.

The positioning application is an application software or program that provides or presents the desired position of person or an object, the desired posture of the person or the object in the bed 610 or the wheelchair 630. The person of the positioning application here may be, for example, the patients, the caregivers, or both. Also, the objects are cushions, diapers, and surrounding furniture and further any other objects. The positioning applications may also present or provide the desired position of the person or the object, the desired posture of the person or the object in a patient's living room, etc.

For example, the positioning applications may operate in a setting mode that performs settings or in a usage mode that supports the caregivers adjusts the positions or the postures of the person or the object according to the settings. In the setting mode, for example, the positioning application acquires the correct data including the images of the person or the object at the desired position or the desired posture. The skilled caregivers may set the images of the desired position or the desired posture using his or her tacit knowledge here. For example, the skilled caregivers may take images of the person (the patient, the caregiver, or both) or the object at the desired position or the desired posture and register the image as the correct data. Then, in the usage mode, the positioning application superimposes the transparent correct data over current image acquired from the camera of the terminal device 200 to adjust the desired position or the desired posture of the person or the object.

Figure 8A:
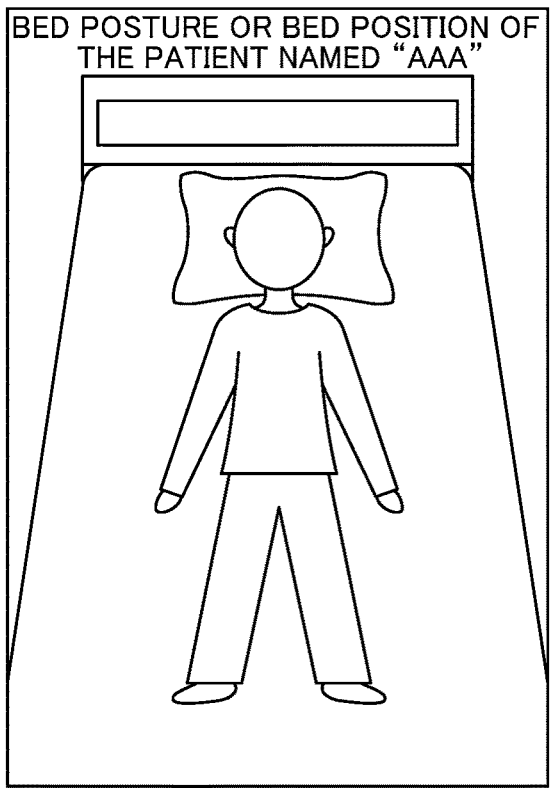
FIG. 8A is an example of correct data in a positioning application.
Figure 8B:
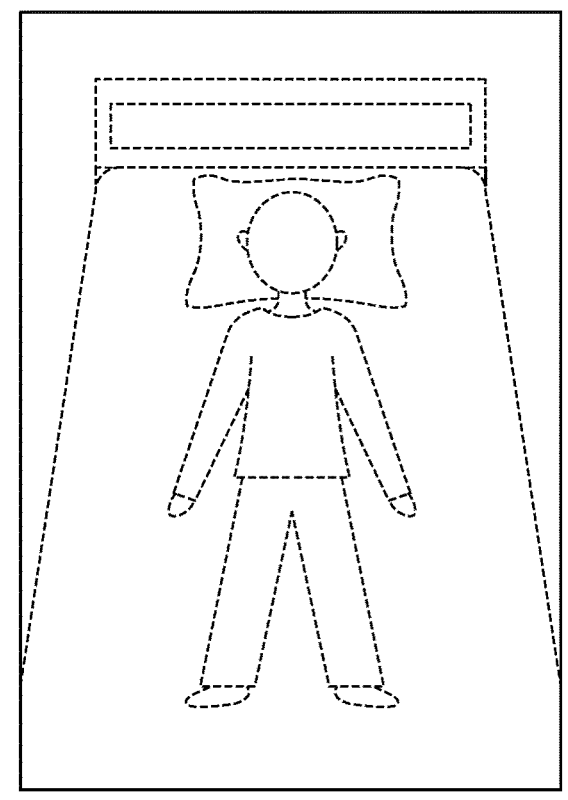
FIG. 8B is an example of correct data displayed transparently in the position application.

The FIG. 8A is an example of the correct data set in the setting mode. In the example in FIG. 8A, the image information representing the desired position or the desired posture of the patient with the name "AAA" lying on the bed 610 is acquired as the correct data. The FIG. 8B is an image example where the correct data is superimposed on the captured image in the usage mode and an image example of the transparent correct data. For example, the fourth terminal device 200D superimposes the image of FIG. 8B (the transparent correct data) over the current image of the person to be adjusted in the position or the posture. The caregivers can adjust the position or the posture of the person or the object by using the captured image so that the position or the posture of the person or the object is closer to the correct data. Although an example of superimposing the image of the correct data over the captured image is described here, the positioning application may output the determination result (OK or NG) of whether the position or the posture of the person or the object is appropriate.

Figure 9:
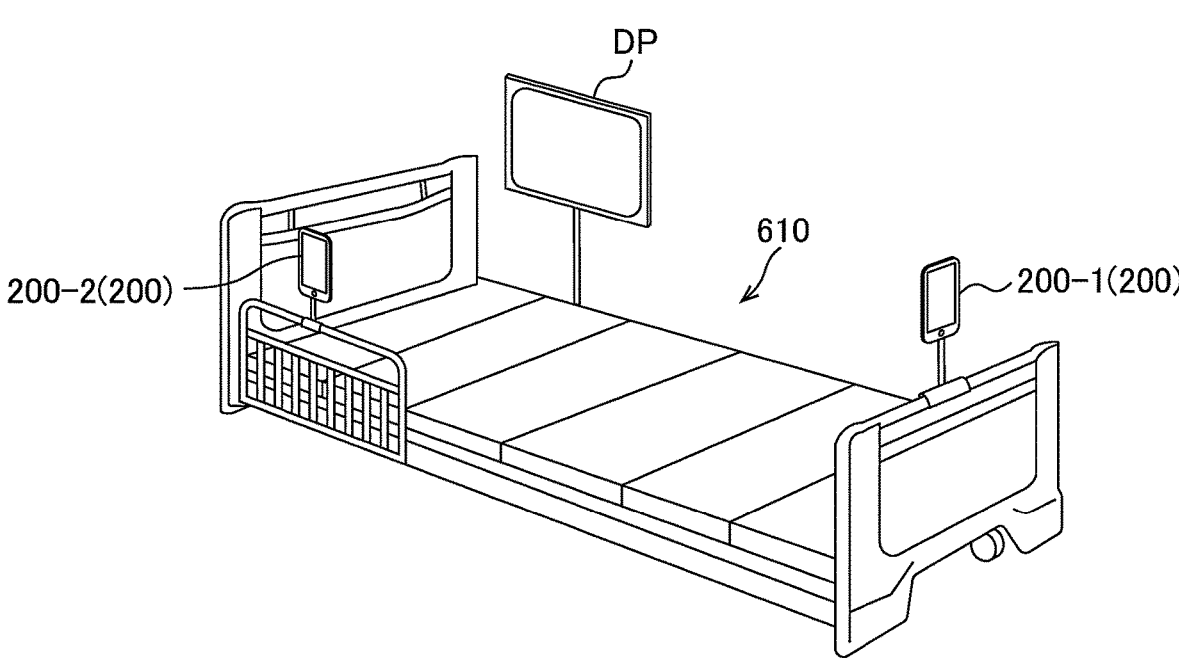
FIG. 9 is an example of devices provided around a bed.

The FIG. 9 is a diagram showing an example of device arrangement around the bed 610 when the positioning application is used to adjust the position or the posture (Hereafter described as bed position) of a person or an object in the bed 610. As shown in FIG. 9, the fourth terminal device 200D in this embodiment may be a terminal device 200-1 attached to the footboard side of the bed 610, a terminal device 200-2 attached to the side rail of the bed 610, or both. However, the position where the fourth terminal device 200D is attached is not limited to this, this device 200D may be attached to another position on the bed 610, or the fourth terminal device 200D may be attached to another position on the bed 610 where the patient can be captured (for example, the walls of the living room, furniture, etc.). Alternatively, the fourth terminal device 200D may be carried by the care assistants or other caregivers, and the processing described below may be performed by activating the positioning application and grasping the fourth terminal device 200D while the care assistant is around the bed such as standing on the footboard side or the side rail side of the bed 610.

For the bed 610, a display DP may be arranged on the opposite side of the terminal device 200-2. The display DP may be attached to the bed 610 or may be attached or arranged in another position that is naturally viewable by the care assistant to adjust the position or the posture of the person or the object using the positioning application. For example, the display DP may be attached to a wall surface or may be attached to a stand that stands independently on the floor. Also, the display DP may be omitted.

The fourth terminal device 200D is, for example, a device such as a smartphone including an imaging unit 260 (camera). The fourth terminal device 200D displays an image in which the correct data (FIG. 8B) is superimposed over the captured image on a display DP or on a display unit 240 of the fourth terminal device 200D.

The positioning application can support the caregivers adjusts a bed position or a bed posture of the person. For example, the positioning application may be used to control the person's posture to suppress the pressure ulcers of the patient or to control an arrangement of cushions. The positioning application may also be used to control the patient's posture when the caregiver changes a diaper of the patient or to control the arrangement of the diapers of the patient. The positioning applications are not limited to those used to adjust the bed position or the bed posture and may be used to adjust the position or the posture of the patient or the object in the wheelchairs 630.

3, Interface for the Medical Caregivers or the Care Assistants

Next, the method for sharing information between the medical caregivers and the care assistants is explained.

3.1 Processing Flow

Figure 10A:
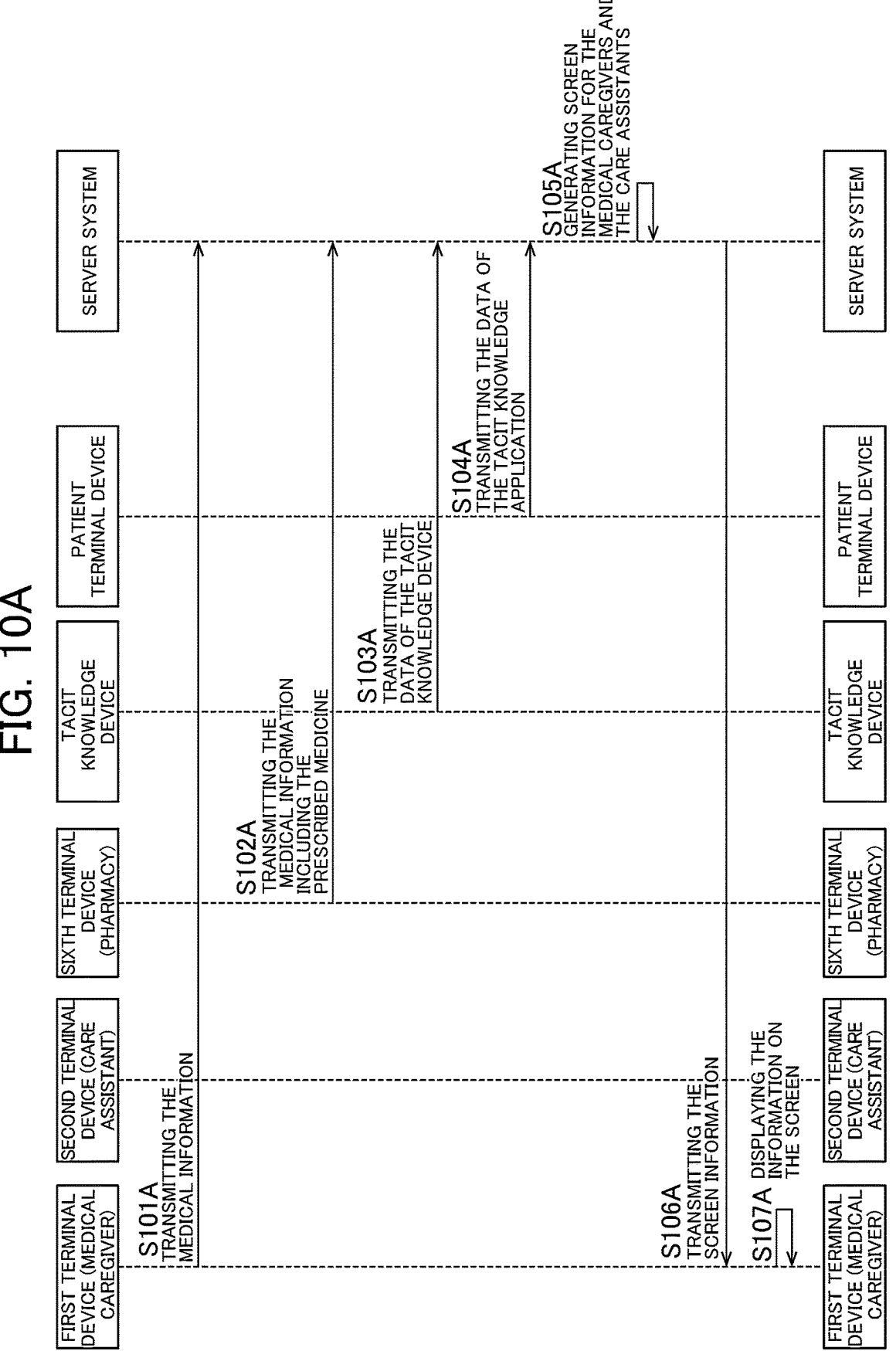
FIG. 10A is a sequence diagram illustrating the processing to share medical and care assistance information.
Figure 10B:
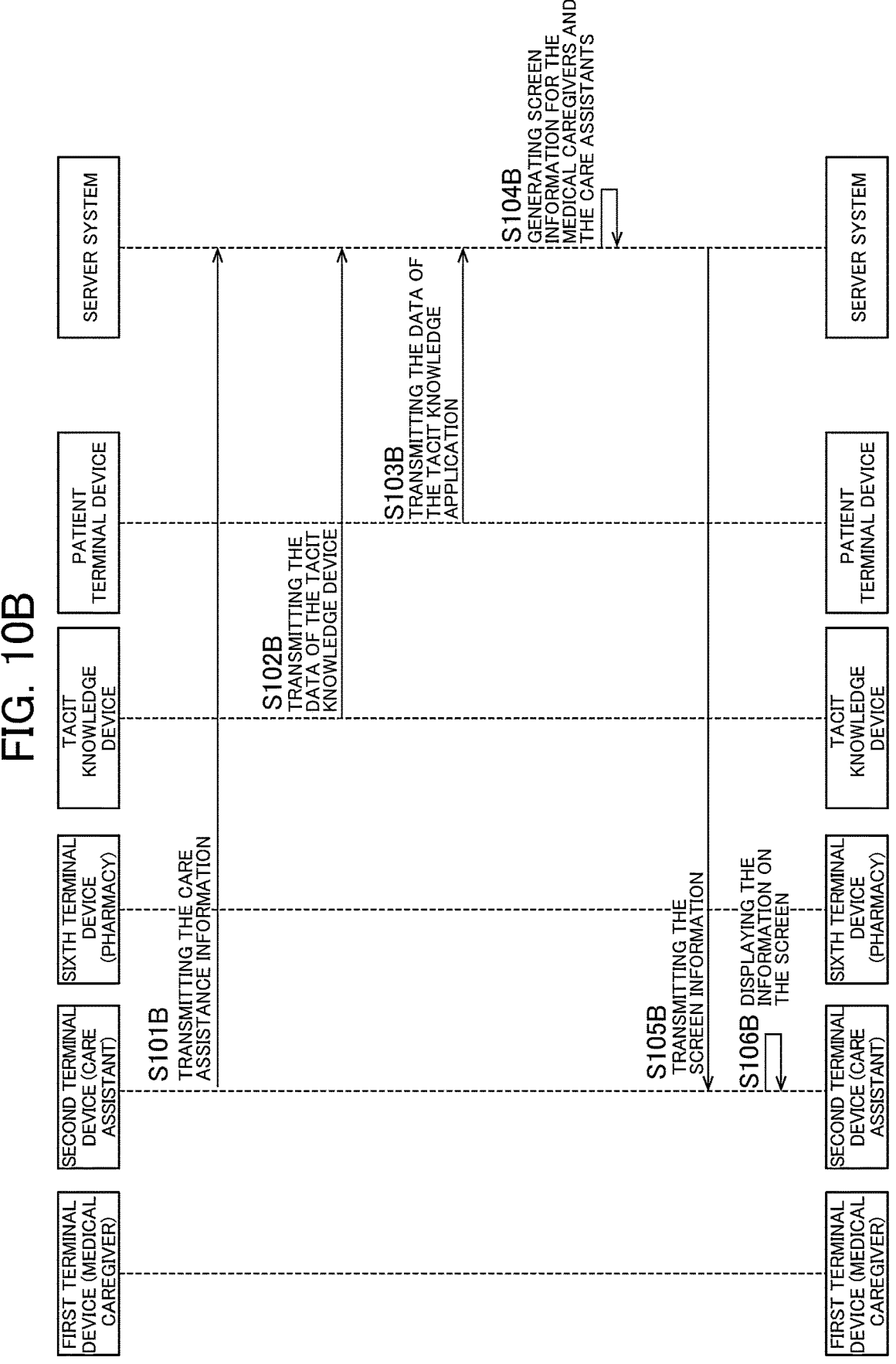
FIG. 10B is a sequence diagram illustrating the processing to share medical and care assistance information.

The FIGS. 10A and 10B are sequence diagrams for explaining a processing of the information processing system 10 of this embodiment, and particularly for explaining a processing for sharing the medical information from the first terminal device 200A and the care assistance information from the second terminal device 200B.

The FIG. 10A is a diagram for explaining a processing related to the first terminal device 200A of the medical caregivers. Firstly, in the step S101A, the first terminal device 200A sends the medical information to the server system 100. For example, the medical caregiver may conduct patient telemedicine (telemedicine) by using the medical information from the first terminal device 200A and the fourth terminal device 200D.

For example, the first terminal device 200A and the fourth terminal device 200D of this embodiment may operate according to application software including a Web meeting function. The first terminal device 200A transmits the images of the medical caregivers and audio data of the medical caregivers to the fourth terminal device 200D. The fourth terminal device 200D transmits the images of the patients and audio data of the patients to the first terminal device 200A. The Web conferencing is executed, in a narrow sense, by the server system 100 of this embodiment, but may be executed via other devices. The medical caregivers may ask some questions to the patient and may input the diagnosis based on the response to the some questions using the operation unit 250 of the first terminal device 200A. Thus, the first terminal device 200A acquires the medical information including the diagnosis, and transmits the medical information to the server system 100 in the step S101A.

Also, if the medical caregiver issues a medicine prescription to the patient based on telemedicine, the pharmacy provides the patient with the medicine based on the medicine prescription. The medicine may be provided face to face at the pharmacy, or the patient and the pharmacist may conduct a consultation remotely using the fourth terminal device 200D and the sixth terminal device 200F, and the medicine may be provided by mail or other methods based on the diagnosis. In this case, in the step S102A, the sixth terminal device 200F used at the pharmacy transmits the medical information including the medicine prescribed to the patient to the server system 100. If no prescription is issued, the processing in the step S102A may be omitted.

The information from other devices included in the information processing system 10 may also be transmitted to the server system 100. For example, in the step S103A, the tacit knowledge device 400 executes a processing according to the tacit knowledge and transmits the processing result of the tacit knowledge device 400 to the server system 100. Also in the step S104A, the fourth terminal device 200D operates according to the tacit knowledge application and transmits the result of the tacit knowledge device 400 to the server system 100. The processing of the steps S103A and S104A may be performed independently of the processing of the steps S101A and S102A, for example. For example, the telemedicine and telemedicine may be performed regularly, and in the intervening period, the care assistance by a family member using the tacit knowledge may be performed. In this case, the tacit knowledge applications and the tacit knowledge devices 400 transmit the information related to the care assistance by the family to the server system 100.

Alternatively, the processing of the steps S103A and S104A may be performed in conjunction with the processing of the steps S101A and S102A. For example, when the caregivers preform the remote diagnostics with the patient or the family member of the patient in the telemedicine, the fourth terminal device 200D may transmit the processing result of the tacit knowledge application or the tacit knowledge device 400 to the first terminal device 200A. The medical caregivers may then input the medical information based on the processing results of the tacit knowledge application or the tacit knowledge device 400 in addition to the diagnosis of the telemedicine. Similarly, the fourth terminal device 200D may transmit the processing results of the tacit knowledge application or the tacit knowledge device 400 to the second terminal device 200B, and the care assistants may input the care assistance information based on the processing results of the tacit knowledge application or the tacit knowledge device 400 in addition to the diagnosis of the telemedicine.

The processing of the steps S103A and S104A is not mandatory, and one of the step S103A and S104A or both may be omitted. The processing of the steps S101A to S104A in FIG. 10 A is not limited to those executed in this order, and each processing may be executed at an arbitrary timing.

After the processing of the steps S101A to S104A, in the step S105A, the server system 100 generates or updates screen information for the medical caregivers and the care assistants based on the information acquired in the steps S101A to S104A. For example, if the information related to the target patient has not been generated, the server system 100 generates a screen related to the target patient based on the information acquired in the steps S101A to S104A. If the information related to the target patient has already been generated, the server system 100 also updates a screen related to the target patient based on the information acquired in the steps S101A to S104A. The information from various terminal devices 200 used by the caregivers (the medical caregivers, the care assistants, or both) in charge of the patient is used to generate or update the screen related to the target patient For example, if the caregivers (specialists) other than the medical caregivers shown in FIG. 10A is in charge of the same target patient and the information from the terminal device 200 of this caregivers (specialists) is stored in the server system 100, that information will also be displayed in the screen related to the target patient.

The processing in the step 105A may also include processing to predict the risk of the patient and processing to estimate the ADL of the patient. For example, the processing unit 110 of the server system 100 may predict the risk of the patient based on the method disclosed in The U.S. Patent Application Publication No. 2021/029600. Here, the risk represents an element affecting the life, the health, the daily life, of the patient in the field of the medical care and the care assistance. For example, the risk may represent the risk of suffering from a specific disease, or the risk may be the risk of incidents that may occur in the medical care or the care assistance in daily life, such as falling and bedsores.

The processing unit 110 may also perform the processing to estimate the risks based on the tacit knowledge. For example, the skilled medical caregivers diagnose the patient himself or herself, conduct the interview with the patient, observe daily activities of the patient, determine whether there are the incident risks for the patient, and input the determination result whether there are the incident risks for the patient as correct data. The correct data may be, for example, input by the first terminal device 200A. The server system 100 generates a learned model by performing machine learning based on the training data in which the correct answer data is associated with the input data about the target patient. The medical caregivers may input the determination result as well as the type of parameters (data) used to determine whether there are the risks for the patient and the period of time to be determined. The server system 100 may specify the type and period of data to be used as the input data based on this information. The processing unit

110 determines whether there are the risks for the patient by inputting the input data into the learned model. For example, for each of the multiple risks, the processing unit 110 may determine the certainty or possibility with whether the risk occurs as numerical data from 0 to 1. The input data here includes, for example, the processing result of the tacit knowledge application and the sensing data output by the tacit knowledge device 400. The input data may also include information on patient attributes, etc.

The processing unit 110 may also perform processing to acquire or estimate ADL of the patient based on the tacit knowledge. For example, the server system 100 may generate a learned model tp estimate the ADL of the patient by acquiring the result of ADL determined by the skilled caregivers as the correct answer data and performing the machine learning based on the correct answer data in the same manner as the processing to estimate the risks based on the tacit knowledge. The processing unit 110 may estimate the index value of the ADL of the patient by inputting the input data into the learned model. The input data here is similar to, for example, the input data using the processing to estimate the risks based on the tacit knowledge, but various modifications such as omitting some data or adding other data can be performed. In the same way as the processing to estimate the risks, the medical caregivers may use the first terminal device 200A to input the types of parameters (data) used to determine or estimate ADL of the patient and the period to determine or estimate ADL of the patient. For example, the medical caregivers may input the data of which tacit knowledge device 400 is used as the input data. The server system 100 may specify the type and period of data to be used as the input data based on this information. For example, the processing unit 110 outputs numerical data representing the degree of ADL.

Also, the learned model here may include RNN (Recurrent Neural Network) such as LSTM (Long Short Term Memory). Then, the processing unit 110 may predict future changes in ADL of the patient by inputting the input data, which is time-series data, into the learned model. This prediction related to the future changes enables not only current estimation of ADL of the patient but also the prediction of ADL of the patient in the future, so that it is possible to take measures such as advance preparations for necessary actions in the future.

In the step S106A, the server system 100 transmits the screen information to the first terminal device 200A. In the step S107A, the display unit 240 of the first terminal device 200A displays the screen corresponding to the screen information. As the result of this, the first terminal device 200A of the medical caregivers can display the medical information transmitted by the medical caregivers with respect to the target patient and other information transmitted by other caregivers (which may include other medical caregivers, or the care assistants) with respect to the target patient in the screen. For example, if the processing shown in FIG. 10B, which will be described later, is performed before the processing shown in FIG. 10A, the server system 100 has already acquired the care assistance information input from the care assistants. Therefore, in the step S107A, it becomes possible to make the first terminal device 200A of the medical caregivers display a screen including the care assistance information input by the care assistants in charge of the same patient.

The FIG. 10B is a diagram illustrating the processing of the second terminal device 200B of the care assistants. Firstly, in the step S101B, the second terminal device 200B transmits the care assistance information to the server system 100. For example, the care assistants use the second terminal device 200B and the fourth terminal device 200D to provide a remote care assistance (a care assistant conducted remotely) to the patient.

For example, the second terminal device 200B of this embodiment may also operate according to application software including the Web meeting function. The second terminal device 200B transmits images captured by the care assistants and the audio data acquired by the care assistants such as the voice of the care assistants to the fourth terminal device 200D. The fourth terminal device 200D transmits images of the patient captured by patient or patient's family member and the audio data including the patient's voice to the second terminal device 200B. The care assistants conduct the interview with the patient, provides care guidance or care instruction to the patient or the patient's family, etc., and, inputs the result of the interview using the operation unit 250 of the second terminal device 200B. In the case of the remote care assistance, the care assistants may set the tacit knowledge suitable for the target patient to the tacit knowledge applications or the tacit knowledge devices. In this way, even in a situation where the caregivers in charge of the target patient is not able to directly see the patient, that is the caregivers in charge of the target patient are not in the location where the patient is, the family members of the patient, etc. can use the tacit knowledge to provide appropriate care assistance. The care assistance information transmitted by the second terminal device 200B may include the setting information of the tacit knowledge applications or the tacit knowledge devices. Although the detailed explanation is omitted in FIG. 10A, the medical information transmitted by the first terminal device 200A may include the setting information of the tacit knowledge applications or the tacit knowledge devices. Accordingly, the second terminal device 200B acquires the care assistance information including results of the care assistance, and in the step S101B, transmits the care assistance information to the server system 100.

The information from other devices in the information processing system 10 may also be transmitted to the server system 100. For example, in the step S102B, the tacit knowledge device 400 performs processing or operates according to the tacit knowledge and transmits the processing result to the server system 100. Also in the step S103B, the fourth terminal device 200D performs processing or operates according to the tacit knowledge application and transmits the processing result to the server system 100. Since the processing of the steps S102B and S103B is similar to the processing of the steps S103A and S104A in FIG. 10A, a detailed description is omitted.

Also, after the processing of the steps S101B to S103B, in the step S104B, the server system 100 generates or updates screen information for the medical caregivers and the care assistants based on the information acquired in the steps S101B to S103B. The processing in the step S104B is similar to the processing in step S105A in FIG. 10A.

Also in the step S105B, the server system 100 transmits the screen information to the second terminal device 200B. In the step S106B, the display unit 240 of the second terminal device 200B displays the screen corresponding to the screen information. As the result of this, the second terminal device 200B which the care assistants hold can display the care assistance information transmitted by this care assistants in charge of the target patient and the information transmitted by other caregivers such as the specialists in charge of the target patient. For example, if the server system 100 performs the processing shown in FIG. 10A before performing the processing shown in FIG. 10B, the server system 100 has already acquired the medical information from the medical caregivers. Therefore, in the step S106B, it becomes possible to have the second terminal device 200B of the care assistants display a screen including the medical information acquired by the medical caregivers in charge of the same patient.

As described above, in the method of this embodiment, since the server system 100 may accumulate the information on the target patient by receiving the medical information from the medical caregivers and the care assistance information from the care assistants and allow the information including the medical information and the care assistance information to review on each terminal device 200, it becomes possible to share information among multiple caregivers in charge of the same patient. For example, it becomes possible to appropriately share determination results and diagnosis, etc. on a target patient between the medical caregivers and the care assistants.

In this embodiment, there may be multiple medical caregivers in charge of the target patient such as a doctor, a registered nurse, and a certified nursing assistant for example, and each of the multiple medical caregivers may have a first terminal device 200A. In this case, the first terminal device 200A of the first medical caregiver may display the medical information entered by the second medical caregiver. Similarly, there may be multiple care assistants in charge of the target patient, and each of the multiple assistants may have a second terminal device 200B. In this case, the second terminal device 200B of the first assistant may display the care assistance information entered by the second assistant.

Thus, in the method of this embodiment, the information described above may be shared among multiple medical caregivers or among multiple care assistants. For example, the information described above may be shared by multiple physicians in different specialties (departments), or the information described above may be shared between physicians and pharmacists. Similarly, the information described above may be shared, for example, between a first care assistant who works during the day and a second care assistant who works during the night, or between a care manager and an on-site caregiver.

3.2 Display Screen Example

The FIG. 11 is a screen example displayed on the display unit 240 of the first terminal 200A or the second terminal 200B. For example, the first terminal device 200A and the second terminal device 200B may operate or preform the processing according to software including the function of conducting a Web conference (Web conference function). The icons such as "microphone," "camera," "chat," and "reaction" displayed on the bar at the top of the screen in FIG. 11 are used for the telemedicine using the Web conference function, remote care assistance using the Web conference function, etc. For example, when the icon of "diagnosing" is selected by the user such as the doctor, the telemedicine using the first terminal device 200A and the fourth terminal device 200D is started, and the Web conference may be set using the icon of "microphone," "camera," "chat," and "reaction" etc. Note that FIG. 11 shows a screen example displayed on the first terminal device 200A used by a physician (Dr. XXXXX) named "XXXXX", but a screen example displayed on the second terminal device 200B is substantially same as the screen example displayed on the first terminal device 200A. If another participant participates while using the Web conference function, the information about the another participant may be displayed on the screen of the first terminal device 200A and the second terminal device 200B. In FIG. 11, the information about the participant with the name "B" is displayed on the right side of the screen of the first terminal device 200A and the second terminal device 200B. The displayed information may be text, an image, or sound acquired by the camera or microphone of the terminal device 200 used by User named "B".

In addition, the software according to this embodiment communicates with the server system 100 through the communication unit 230, and performs the processing for receiving the screen information as shown in the step S106A in FIG. 10A and the step S105B in FIG. 10B, and the processing for displaying the screen corresponding to the screen information as shown in the step S107A in FIG. 10A and the step S106B in FIG. 10B. For example, the processing unit 210 in the first terminal device 200A and the second terminal device 200B may display the area RE1 for displaying the medical information, the care assistance information, the risk prediction results of the target patient, by selecting the "linkage" icon displayed at the top of the screen in FIG. 11 as a trigger.

The area RE1 includes the area RE11 to display the period of the information which displays on the screen the area RE12 to display an object to switch whether the risk prediction results are displayed or not, the area RE13 to display the medical information corresponding to the diagnosis, and the area RE14 to display the risk prediction results.

For example, the area RE11 displays an object representing the start timing of the period to be displayed and an object representing the end timing of the period to be displayed. The server system 100 firstly acquires the start timing of the period and the end timing of the period by default, and transmits the screen information including the medical information and the care assistance information in the designated period to each terminal device 200. The medical caregivers and the care assistants may also input the start timing and end timing of the period in the area RE11. For example, if the server system 10 receive the information to change the designated period from any of the terminal devices 200, the server system 10 may perform the processing to update the screen information to be transmitted to the terminal devices 200 to include the medical information, the care assistance information and the like in the changed period. This processing makes it possible to flexibly change the period to be displayed on the terminal device 200.

The medical caregivers or the care assistants may also switch whether the risk prediction results are displayed or not by manipulating objects (e.g., checkboxes) displayed in the area RE12. For example, the first terminal device 200A and the second terminal device 200B may perform the processing to display the risk prediction results in the area RE14 if the checkboxes are checked, and perform the processing not to display the risk prediction results in the area RE14 if the checkboxes are unchecked.

The details of the medical information corresponding to the diagnosis are displayed in the area RE13. As explained using FIGS. 10A and 10B, the information displayed here includes the information accumulated in the server system 100 prior to the timing of generating the screen information (the steps 105A, S104B). That is, the medical information displayed here represents the past diagnosis prior to a current timing. For example, the medical information includes the information such as the name of the medical institution, date of diagnosing, contents of diagnosis, contents of treatment, contents of prescription, etc. In the example of FIG. 11, for example, the target patient was diagnosed on x (e.g. May) y (e.g. 5), 2022 at the Clinic A, and as a result, the target patient was diagnosed as a disease called "XXXX" and a medicine called "YYYY" was prescribed. This information is displayed in the area RE13. The case of University Hospital B is displayed similar to the case of the Clinic A, for example, a surgical operation called "ZZZ" was performed on x (e.g. August) y (e.g. 10), 2022, and a medicine called "asdks" was prescribed. This information is also displayed in the area RE13.

Also, the medical institution here may include a pharmacy. In the example in FIG. 11, a medicine called "YYYY" was prescribed on x x, 2022 and a medicine called "asdks" was prescribed on x y, 2022 at a pharmacy C. For example, the medicine history is shown in FIG. 11 if the medicine "YYYY" was prescribed at the pharmacy C based on the prescription issued at the clinic A and the medicine "asdks" was prescribed at the pharmacy C based on a prescription issued at the University Hospital B.

The area RE 13 related to the medical information may display the medication status object OB1 for confirming the medication status of the medication in association with the information related to the prescribed medication. For example, the processing unit 110 of the server system 100 performs a processing to estimate the medication status. The display unit 240 in the first terminal device 200A and the second terminal device 200B may display an estimated medication status if the medication status object OB1 is selected. The estimation processing of the medication status will be described later with reference to FIGS. 14 to 19. The screen displaying the medication information will be described later with reference to FIG. 20.

The area RE14 may display the details of the risk prediction results. In the example of FIG. 11, the processing unit 110 determined that the risk of sepsis, the risk of covid, the risk of falling, the risk of mild dementia, and the risk of pressure ulcers were more than or equal to the prescribed thresholds in the processing of the step S105A in FIG. 10A and the step S104B in FIG. 10B. In this example, each risk is classified into Class 0 to Class 10 according to the degree of the risk, and a risk of Class 1 or higher is displayed in this example. However, various modifications can be made to the risk assessment method, selection criteria for the items to be displayed, etc.

And, in the method of this embodiment, it may be possible to input the responses or how to deal with the risk prediction results by the specialists including the medical caregivers and the care assistants for each risk detected by the risk prediction result. As shown in, for example, the covid risk and the pressure ulcer risk, the registration object OB2 may be displayed in the area RE14 and a plurality of the registration objects OB2 corresponds to a plurality of risks detected by the risk prediction result. For example, since FIG. 11 shows a screen example on the first terminal device 200A used by "Dr. XXXXX", if the doctor named "Dr. XXXXX" selects the registration object OB2 corresponding to the risk and sets the responses or how to deal with the risk prediction results, the first terminal device 200A may perform the processing to register the response of the doctor named "Dr. XXXXX" and transmits a result by performing processing related to the response to the server system 100. In this way, the medical caregiver "Dr. XXXXX" will be able to see all information about the target patients and will be able to register their response for the risks of the target patients. Since the registration object OB2 which is same as FIG. 11 may be displayed in the screen of the terminal device 200 of a certain specialist in charge of same patient other than "Dr. XXXXX", the certain specialist can also register the responses how to deal with the risk prediction results of the target patient if selecting the corresponding registration object OB2. That is, according to the method of this embodiment, in addition to sharing the risk prediction results of the patient, it is possible to urge each of the multiple specialists in charge of the target patient to deal with to the potential risk of the target patient. Furthermore, since the server system 100 transmits the screen information including registration results (specifically, the medical information and the care assistance information including the registration results) to each terminal device 200, it is possible to share history information who registers what kinds of responses how to deal with the risk among the multiple specialists. The process flow to transmit the registration results to the server system 100 and to display the screen including the registration results on the terminal device 200 is similar to, for example, the process flow in FIGS. 10A and 10B.

It should be noted that the registration object OB2 shown in FIG. 11 is not limited to those displayed on the terminal device 200 of all specialists. For example, the server system 100 may be able to set an authority whether or not each specialist has the authority to register the responses how to deal with the risk of the target patient. In this case, the server system 100 may perform processing to display the registration object OB2 on the terminal device 200 of the authorized specialist and not to display the registration object OB2 on the terminal device 200 of the unauthorized specialist. In this way, the specialist who have the authority to register the response can be limited to the appropriate specialist. For example, the server system 100 may determine the proficiency level of each caregiver and grant the authority to register the response to the specialist whose proficiency level is more than or equal to a predetermined level. Alternatively, the server system 100 may determine the confidence level from the patient based on sentiment analysis or the like and grant the authority to register the response to the specialist whose confidence level is more than or equal to a predetermined level. Alternatively, the server system 100 may determine the proficiency level or the like for each risk, and determine whether each specialist has the authority to register the response for each risk. The method to grant the authority to register the response is not limited to this method, various modifications can be made to the detailed processing of authorization.

The medical information may include the response how to deal with the risk of the target patient by medical caregivers and the results of the response, because these responses and the results are the determination of the medical caregivers regarding the patient. The care information may include the response how to deal with the risk of the target patient by care assistants and the results of the response, because these responses and the results are the determination of the care assistants regarding the patient. Therefore, the response information for each predicted risk may be displayed as the medical information and the care information on the screen shown in FIG. 11.

Specifically, the server system 100 may determine the target patient's risk of developing sepsis and displays the target patient's risk to the Dr. XXXXX. Dr. XXXXX deems that certain response is unnecessary. In this case, Dr. XXXXX uses the operation unit of the first terminal device 200A to select the object OB2 associated with the sepsis risk and to input that no response is required. In this way, the type of the risk, the contents of the risk, the contents of the responses by the caregivers, and the information of the caregivers who registered the responses are registered in association. In the example of FIG. 11, the type of risk or the contents of the risk corresponds to the "sepsis risk" and the contents of the responses by the caregivers are "no response," and the information of the caregivers who registered the responses is "Dr. XXXXX". If the server system 100 may send the information about the target patient to each terminal device 200, the server system 100 may also send the information about the registered response corresponding to the predicted risk. This makes it possible not only to share the risk results predicted by the server system 100 or by the certain caregiver for example, but also to share the response by other caregivers.

The response in this embodiment may be the prescription of the medicine (the doctors and the pharmacists), the appointment for surgery (the doctor), the execution of rehabilitation (the occupational and the physical therapists), the modification or change of the plan to provide the assistance (the care manager, the caregiver), or any other response. That is, the response in this embodiment may include a variety of responses that can suppress the effect on the patient of the target risk. As noted above, if the caregivers determined that the patient is less affected by the predicted risk, the caregivers may input that no action or no response is required The response in this embodiment may also include the selection of the tacit knowledge to be used for the patient or the usage of the tacit knowledge for the patient. For example, in FIG. 11, for the falling risk of the target patient, the caregiver named "zzzzz" in charge of the target patient and belonged in "ZZZZ" facility, registers the responses of using the tacit knowledge device 400 which is acceleration sensor named xxxx and the tacit knowledge application named yyyy-app. The acceleration sensor xxxx may be, for example, an acceleration sensor worn on the patient. The tacit knowledge application yyyy-app is an application software that performs, for example, processing to detect a foreshadowing of falling based on the acceleration value acquired by the acceleration sensor, or performing a notification processing to prompt the surrounding caregiver to intervene if the tacit knowledge application yyyy-app detects the foreshadowing of falling. The tacit knowledge application yyyy-app may be software that operates on a fourth terminal device 200D used by, for example, the target patient or his or her family, or software that operates on the tacit knowledge device 400.

Similarly, in the example in FIG. 11, for the risk of the mild dementia, a psychiatrist named "dhfkgj" has registered a response to use a tacit knowledge application named "wwwww-app". The tacit knowledge application named "wwwww-app" may be an application software that performs, for example, a detecting process to detect a location of the target patient for suppressing wandering or a notifying process to notify a caregiver if the target patient moves to a specific position. The tacit knowledge application named "wwwww-app" may be another application software to suppress incidents related to the mild dementia (the incidents related to falling, going outside without any permission or without any attendant, or defecating outside the toilet or on another location, etc.) or an application software to suppress the progression of the dementia.

For example, if the medical caregiver selects the certain tacit knowledge, that is, the medical caregiver selects the tacit knowledge devices or the tacit knowledge applications to use the certain tacit knowledge, the first terminal device 200A will transmit the medical information including the certain tacit knowledge (the tacit knowledge devices or the tacit knowledge applications) to the server system 100. Similarly, if the care assistant selects another tacit knowledge that is, the care assistant selects the tacit knowledge devices or the tacit knowledge applications to use the another tacit knowledge the second terminal device 200B will transmit the care assistance information including the another tacit knowledge to the server system 100. That is, the processing unit 110 of the server system 100 may acquire the medical information including information digitizing the tacit knowledge of a skilled medical caregiver and the care assistance information including information digitizing the tacit knowledge of a skilled care assistant. Then, the processing unit 110 of the server system 100 may share the information about the tacit knowledge being applied to the target patient among all caregivers including the medical caregiver in charge of the target patient and the care assistant in charge of the target patient, as shown in FIG. 11 by displaying a screen including information about the tacit knowledge on each terminal device 200. The tacit knowledge selected by the medical caregiver or the care assistant may be the tacit knowledge of the medical caregiver who uses the first terminal device 200A, the tacit knowledge of the care assistant who uses the second terminal device 200B, or the tacit knowledge of a skilled caregiver who is different from any of caregivers described above. For example, as will be described later with the references to FIGS. 23 and 24, the medical caregiver or the care assistant may apply the tacit knowledge which another skilled caregiver creates to the patient by searching the tacit knowledge through the server system 100. In this way, the tacit knowledge that the skilled caregivers find useful can be applied and used to the care assistance for the target patients.

In addition, the server system 100 may send the information that promotes the introduction of recommended tacit knowledge to the fourth terminal device 200D. If the target patient or his or her family approves the introduction of the recommended tacit knowledge in the fourth terminal device 200D, the server system 100 performs processing to introduce the recommended tacit knowledge. For example, the server system 100 may perform processing to install the tacit knowledge devices or the tacit knowledge applications corresponding to the recommended tacit knowledge to the fourth terminal device 200D. Alternatively, the server system 100 may perform processing to update the tacit knowledge application of the recommended tacit knowledge device 400 or to install the updated version tacit knowledge application corresponding to the recommended tacit knowledge. The server system 100 may also send the link information to the EC (electronic commerce) web page or the like to introduce the new tacit knowledge device 400 to the fourth terminal device 200D.

As described above, the tacit knowledge how to deal with the predicted risk as the skilled caregiver's response can appropriately suppress the possibility or influence of each risk in daily life of the target patient. For example, the server system 100 may manage the information about the tacit knowledge by associating the tacit knowledge registered in the server system 100 with the electronic medical record of the patient in the medical service or the nursing software in the nursing care service. It should be noted that the medical service and the nursing care service here are not limited to services provided at hospitals and nursing facilities, etc., and may include various services related to medical and nursing care, such as home-visit medical care, home-visit nursing care and rental of some devices which are used in the medical service or in the nursing care service.

3.3 Requests

In the method of the present embodiment, the processing unit 110 of the server system 100 may perform processing to present information indicating that a review request has been received from the first terminal device 200A on the second terminal device 200B if the server system 100 receives a request from the first terminal device 200A to review the care assistance information associated with the target patient. In this way, the request from the medical caregiver can be used as a trigger to urge the care assistants to review the current care assistance information and reconsider how to update the current care assistance information. For example, in this embodiment, if the care assistant registers a response how to deal with the predicted risk, the medical caregiver may request an update the contents of the response which the care assistant had registered. As the result of this, the responses registered by the care assistant are updated after the medical caregiver reviews the registered responses, allowing for comprehensive care assistance that reflects the tacit knowledge of multiple skilled caregivers.

Similarly, if the processing unit 110 of the server system 100 receives a request from the second terminal device 200B to review the medical information associated with the target patient, the server system 100 may perform processing to present information indicating that a review request has been received from the second terminal device 200B on the first terminal device 200A. In this way, the request from the care assistant can be used as a trigger to urge the medical caregivers to review the current medical information and reconsider how to update the current medical information. In this way, for example, the response registered by the medical caregiver is updated after the care assistant reviews, so that comprehensive care reflecting the opinions or the tacit knowledge of multiple skilled caregivers can be implemented.

The request in this embodiment may be, for example, a request to update the tacit knowledge by changing the tacit knowledge device and the tacit knowledge application. We consider, for example, a case in which there is a target patient who has the risk of falling, another caregiver had already registered the tacit knowledge to handle the risk of falling, and the doctor intends to prescribe a certain medicine for another disease of the target patient by performing the telemedicine remotely, that the doctor diagnosing remotely. Here, the doctor may be able to predict that the risk of falling may be higher than before if the certain medicine is prescribed. In this case, the doctor may request a review of the tacit knowledge which had already applied to the target patient to suppress the risk of falling and had already been set by another caregiver (e.g., a care caregiver) using the first terminal device 200A with the "request" button.

For example, as shown in FIG. 11, the request object OB3 may be displayed in the area RE14 in the display screen of the medical information and the care assistance information in association with the predicted risk. In a narrow sense, the request object OB3 is displayed in association with the risk for which the tacit knowledge is registered as the response among the predicted risks. In the example of FIG. 11, the request object OB3 is displayed in association with the risk of falling and the risk of the mild dementia.

For example, the doctor "Dr. XXXXX" who sees the screen of FIG. 11 may request at least one of updating of the tacit knowledge device 400 (e.g. the acceleration sensor xxxx) and updating of the tacit knowledge application (e.g. the tacit knowledge application software yyyy-app) to the caregiver "zzzzz", by selecting the request object OB3 displayed in association with the risk of falling.

Figure 12:
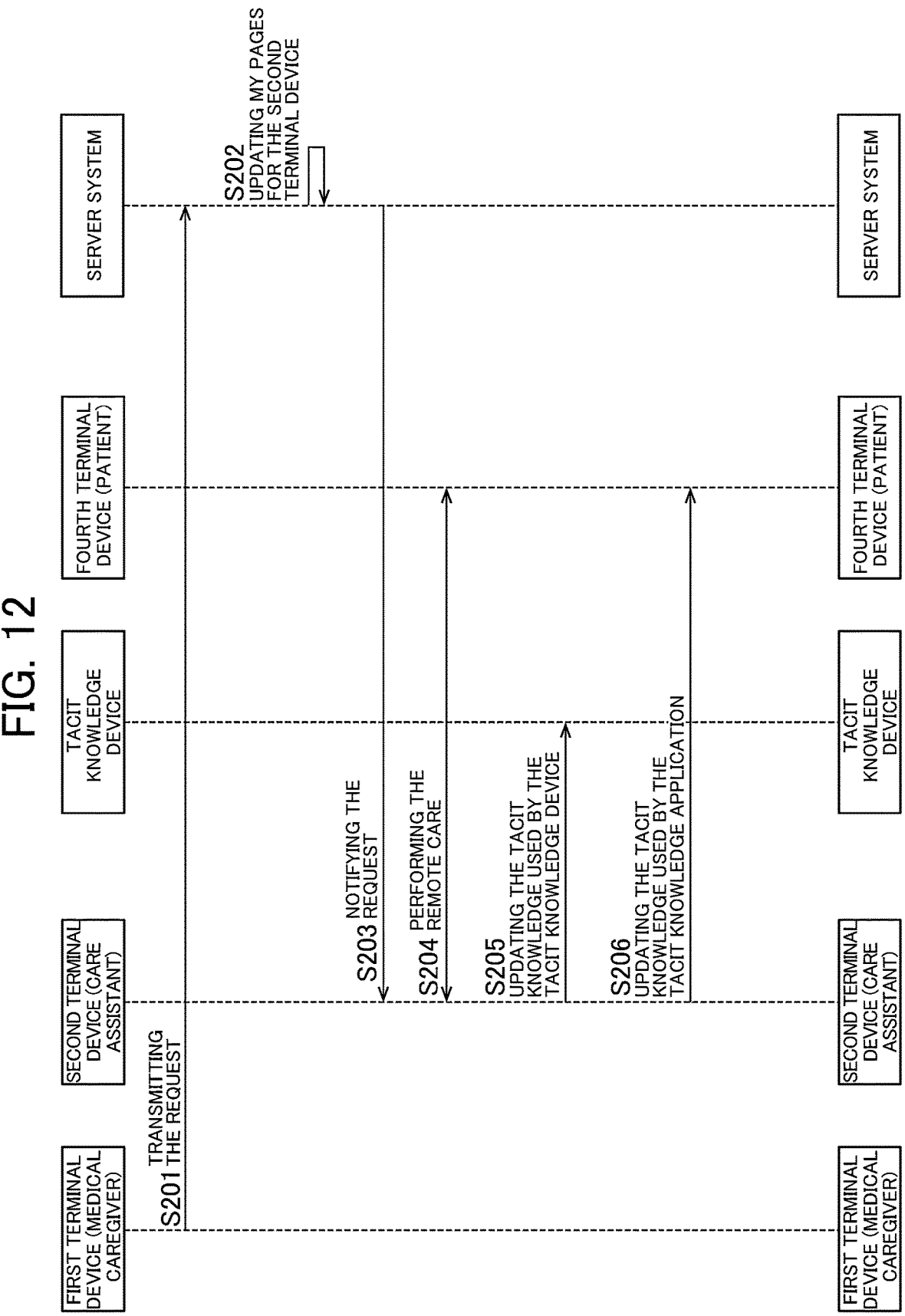
FIG. 12 is a sequence diagram illustrating request processing to update the tacit knowledge.

The FIG. 12 is a sequence diagram illustrating the processing if the medical caregiver requests to review the tacit knowledge including the care assistance information. First, prior to this processing, the processing unit 110 of the server system 100 performs processing to acquire the care assistance information including the information digitizing the tacit knowledge of the skilled caregiver from the second terminal device 200B. In the above example using FIG. 11, the processing to register the acceleration sensor xxxx and the tacit knowledge application yyyy-app is performed from the second terminal device 200B by the caregiver zzzzz who belongs to zzzzz nursing facility, in response to the risk of falling, and the processing unit 110 accepts the processing to register the acceleration sensor xxxx and the tacit knowledge application yyyy-app. The tacit knowledge registered by the caregiver zzzzz here may be the tacit knowledge of the skilled caregiver using the second terminal device 200B or the tacit knowledge of another caregiver. In addition, the tacit knowledge described here may be the tacit knowledge of the medical caregiver. The processing unit 110 transmits the information including the tacit knowledge to the terminal device 200 of each skilled caregiver as shown in FIG. 11.

Then, in the step S201, the operation unit 250 of the first terminal device 200A may receive the operation to select the request object OB3 by the medical caregiver and transmits the information to update the tacit knowledge corresponding to the selected request object OB3 to the server system 100. It should be noted that in the step S201, the medical caregiver may be able to input additional information such as the tendency of the risk fluctuation and the proposal of the desired tacit knowledge, the tacit knowledge device or the tacit knowledge application.

In the step S202, the processing unit 110 updates the screen information for the second terminal device 200B. Specifically, the processing unit 110 performs processing to identify the user who had applied the tacit knowledge which is selected by the request object OB3 to the target patient. Then, the processing unit 110 performs processing to generate the information including the fact the request to update the tacit knowledge has been received as the screen information for transmitting the screen to the second terminal device 200B of the identified user.

In the step S203, the processing unit 110 notifies the request to update the tacit knowledge to the caregiver who uses the second terminal device 200B by transmitting the screen information to the second terminal device 200 through the communication unit 130.

The care assistant receives the notification in the step S203 by activating this software related to this embodiment in the second terminal device 200B. For example, the second terminal device 200B performs processing to display on the display unit 240 the information including the user name or the user id who transmits the request, the contents of the request (e.g., updating of the tacit knowledge), etc. If the care assistant receives this request, the care assistant may start updating the tacit knowledge.

For example, the care assistant performs processing to estimate tacit knowledge more suitable for the target patient by performing the telemedicine remotely with the patient and his or her family using the second terminal device 200B and the fourth terminal device 200D, and inputs or selects the estimated tacit knowledge into the second terminal device 200B. For example, in the step S204, the second terminal device 200B and the fourth terminal device 200D may perform processing related to the Web meeting, and the second terminal device 200B receives the input operation of the selected tacit knowledge by the care assistant. However, it is not essential to perform telemedicine remotely again here. For example, the care assistant may input or select the new suitable tacit knowledge without performing the telemedicine based on the information displayed in FIG. 11 or the contents of the request notification. In this case, the processing of the step S204 can be omitted.

The second terminal device 200B performs processing for introducing the selected tacit knowledge. For example, in the step S205, the second terminal device 200B performs processing to update the selected tacit knowledge application used in the tacit knowledge device 400 by performing processing to update the software on the tacit knowledge device 400 which is already introduced for the target patient. Also in the step S206, the second terminal device 200B performs processing to update the selected tacit knowledge application used in the fourth terminal device 200D by transmitting a new suitable tacit knowledge application to the fourth terminal device 200D. Both of these processes of the step S205 and the step S206 may be performed, or either of them may be omitted. Although FIG. 12 shows an example of updating the tacit knowledge used in the existing tacit knowledge device 400 which is already installed for the target patient, a new tacit knowledge device 400 may be introduced or installed to update the tacit knowledge. In this case, the second terminal device 200B may inquire the fourth terminal device 200D whether or not to introduce or install a new suitable tacit knowledge device 400, and may transmit the information to access a corresponding an EC web page for purchasing the new suitable tacit knowledge device 400. If the caregiver determined that updating the tacit knowledge is unnecessary or the tacit knowledge which is already installed is enough, both the steps S205 and S206 may be omitted. In addition, updating the tacit knowledge may be performed by other devices such as the server system 100.

As described above, if the processing unit 110 of the server system 100 receives the request from the first terminal device 200A to review and reconsider the care assistance information of the target patient (the step S201), the processing unit performs processing in the second terminal device 200B to present the information to encourage the change of the tacit knowledge to be applied to the target patient (the step S202, S203) Thus, in this embodiment, the tacit knowledge registered by the skilled care assistant can be updated based on the tacit knowledge of the medical caregiver who is a specialist in a different field, thus making it possible to provide comprehensive care to the target patient.

In the above, we have described an example in which a medical caregiver sends the request to update the tacit knowledge to be applied to the target patient which is registered by the skilled care assistant, but this is not limited to this example. For example, as shown in FIG. 11, the tacit knowledge how to deal with the risk of the mild dementia may be registered by other medical caregivers. The medical caregivers may then send the request to update the tacit knowledge registered by other medical caregivers. In this case, the server system 100 may receive the request to update the installed tacit knowledge from a given first terminal device 200A and send the information to the other first terminal device 200A to encourage the change of the installed tacit knowledge to be applied to the target patient.

Figure 13:
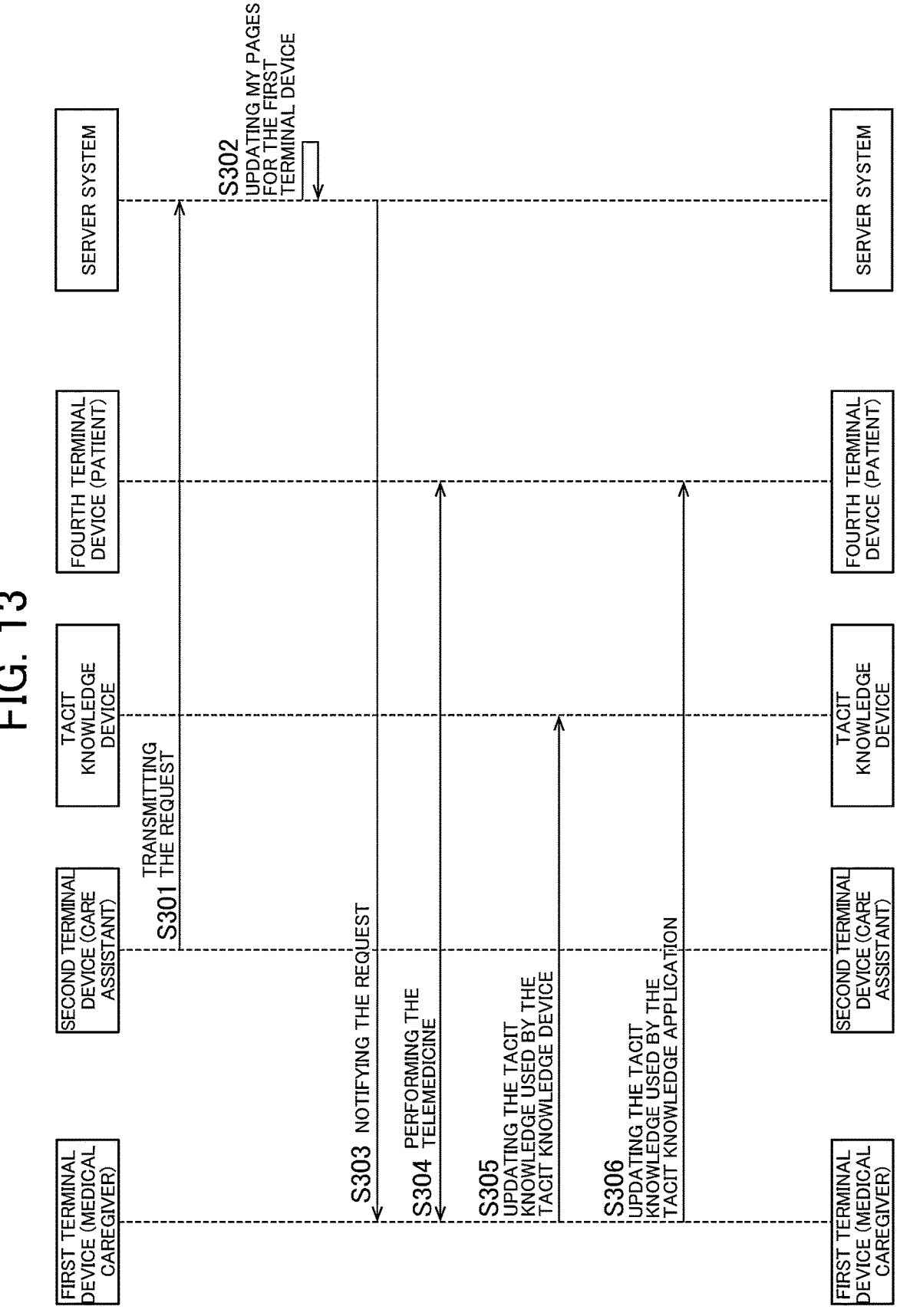
FIG. 13 is a sequence diagram illustrating request processing to update the tacit knowledge.

Moreover, the request to update or reconsider the installed tacit knowledge is not limited to the one received from the medical caregivers, but may be received from the care assistants. For example, care assistant may send the request to update or reconsider the installed tacit knowledge if the care assistant determined that the installed tacit knowledge is not suitable for the target patient. The FIG. 13 is a sequence diagram illustrating the processing flow in this case. Firstly, prior to this processing, the processing unit 110 of the server system 100 performs processing to acquire the medical information including the information digitizing the tacit knowledge of a skilled medical caregiver from the first terminal device 200A.

In the step S301, the operating unit 250 of the second terminal device 200B receives the operation to select the request object OB3 by the care assistant and sends the request to update the selected tacit knowledge update to the server system 100. In the step S302, the processing unit 110 updates the screen information for the first terminal device 200A. In the step S303, the processing unit 110 sends the screen information to the first terminal device 200A via the communication unit 130 to notify the medical caregiver using the first terminal device 200A of the request to update the selected tacit knowledge.

By performing telemedicine (telemedicine) with the patient using the first terminal device 200A and the fourth terminal device 200D, the medical caregiver estimates the tacit knowledge more suitable for the target patient and input or select the tacit knowledge into the first terminal device 200A (the step S304). The telemedicine can be omitted.

In the step S305, the first terminal device 200A performs processing to update the installed tacit knowledge used in the tacit knowledge device 400 by performing processing to update the software on the tacit knowledge device 400 which is already installed for the target patient. In the step S306, the first terminal device 200A also performs processing to update the installed tacit knowledge used in the fourth terminal device 200D by transmitting a new suitable tacit knowledge application to the fourth terminal device 200D. In addition, the new suitable tacit knowledge device 400 may be installed or introduced, which is the same as the example described above using FIG. 12.

As described above, if the processing unit 110 of the server system 100 receives the request from the second terminal device 200B to update or reconsider the medical information associated with a patient (the step S301), the processing unit 110 may perform processing to present the information prompting the change of the installed tacit knowledge in the first terminal device 200A (the step S302, S303). Thus, in this embodiment, the tacit knowledge registered by the medical caregivers can be updated based on the tacit knowledge of the care assistant who is a specialist in different fields, so that comprehensive care can be provided to the target patient.

In this embodiment, the care assistant may send the request to update the installed tacit knowledge registered by the other care assistant. In this case, the server system 100 may receive the request to update or reconsider the installed tacit knowledge from a given second terminal device 200B and send information to encourage the change of the installed tacit knowledge to be applied to the target patient to the other second terminal device 200B.

In the above case, we has described an example in which a medical caregiver using the first terminal device 200A or a care assistant using the second terminal device 200B alone sends the request to update the installed tacit knowledge, the processing of this embodiment is not limited to this processing. For example, the care assistance for the target patient may be considered by several specialists involved in the target patient, such as a care conference or community care conference, or by a team for the care assistance of the target patient which includes the family of the patient and several caregivers or several specialists. In this case, the request to update the installed tacit knowledge may be transmitted based on the determination or the agreement of the team concerned for example. For example, in addition to the terminal devices 200 used alone by the medical caregiver and the care assistant, the terminal devices 200 used by the team may be used to transmit the request and the request to update the installed tacit knowledge may be transmitted by the terminal devices 200. Alternatively, any specialist belonging to the team may transmit the request to update the installed tacit knowledge using the terminal device 200 of the specialist. However, the information related to the caregiver who transmits the request may be a factor that affects the validity of the request. Therefore, if any specialist transmits the request to update the installed tacit knowledge on behalf of the team, the information indicating that the request was transmitted by the team may be sent to the server system 100 and shared with all terminal devices 200 which all caregivers in charge of the target patient hold.

As an example of the request to update the installed tacit knowledge, we have described the case where tacit knowledge is not suitable for the patient in the above paragraphs, but the example of the request to update the installed tacit knowledge is not limited to this case. For example, some tacit knowledge may be difficult to use correctly if the skill level of the caregiver is too low (for example, if the caregiver is a family caregiver, an unskilled nurse etc.). Therefore, the processing unit 110 of the server system 100 may determine whether the skill level of the caregiver is insufficient to use the selected tacit knowledge based on the history of the care assistance from the electronic medical record or nursing record software, etc. If the processing unit 110 determined that the skill level of the caregiver is insufficient to user the selected tacit knowledge, the processing unit 110 may perform a process to prompt or to encourage the medical caregiver or the care assistant to update or to reconsider the tacit knowledge by sending the request to update the installed tacit knowledge automatically. Also, as explained here, the processing unit 110 may perform processing to support the determination of the medical caregiver or the care assistant as to whether or not the medical caregiver or the care assistant should make the request of tacit knowledge. For example, the processing unit 110 may determine whether or not the currently installed tacit knowledge is suitable for the target patient by referring to data such as an electronic medical record. If the processing unit 110 determined that the currently installed tacit knowledge is not suitable for the target patient, the processing unit 110 may perform processing to prompt or to encourage the medical caregiver or the care assistant to update or to reconsider the tacit knowledge.

3.4 Medicine Management

As described above using the area RE13 in FIG. 11, the medical information in this embodiment may include the information about the medicine prescribed for the target patient. However, doctors and pharmacists prepare prescriptions and provide medicines according to the prescriptions, but they do not directly check out whether the target patient had taken the prescribed medicine correctly. Therefore, it may not be easy for them to distinguish specific situations, such as whether the medicines were not effective although the target patient had taken the prescribed medicines, or whether the target patient had not taken the prescribed medicines in the first place, for example, if some risk regarding the target patient is detected. Moreover, it is not easy for them to know whether the target patient had taken the medicines inappropriately, such as taking the medicines with the wrong dosage and wrong usage, or taking the medicines prescribed to others incorrectly.

In addition, if the caregiver such as the care assistant in the nursing facility is near the target patient when the target patient takes the prescribed medication, the caregiver can check out the amount and type of medicine and whether the target patient had taken the medicine appropriately. However, one caregiver need to take care of a large number of the target patients in the nursing facility, and plurality of medicines may be prescribed for a single target patient. Depending on the type of medicine, the target patient may take these medicines at different times or at different doses. This situation makes it difficult for the caregivers to manage medicine manually. There are also known medicine management robots that notify timing which the target patient should take the medicine, discharge the medicine from the medicine management robots based on user operations, and manage medicine history, etc., but these medicine management robots cannot determine whether the target patient had actually taken the discharged medicine.

Therefore, in this embodiment, the medicine management may be performed by determining whether the target patient had actually taken the prescribed medicine using a device which can detect swallowing of the target patient (in a narrow sense, the swallowing choke detection device 460). The examples of detailed methods are described below.

Figure 14:
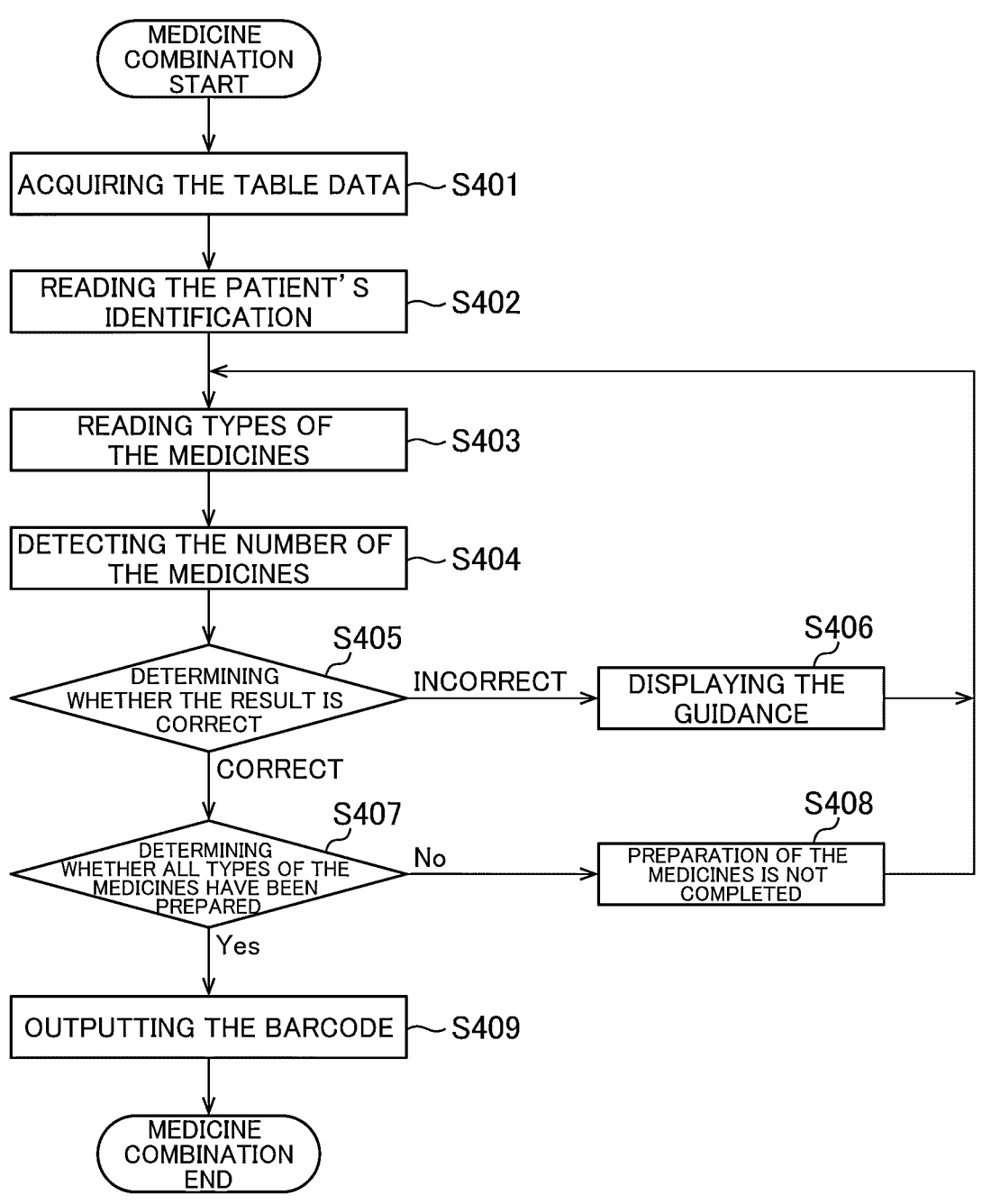
FIG. 14 is a flowchart illustrating a preparation processing of medication management.

The FIG. 14 is a flowchart illustrating the process of preparing medicines for each target patient and each timing the target patient takes the medicine, for example, in the nursing facility. For example, in the nursing facility, the medicines prescribed for multiple target patients are received from the pharmacy for once a week or for once a day for example, the medical caregiver such as the nurse may distribute the medicines to each target patient. The FIG. 14 represents the processing flow to support this work to distribute the medicines to each target patient. In FIG. 14, the processing is performed by the second terminal device 200B for example. However, the processing shown in FIG. 14 may be performed by other devices such as a management PC located in a station or the like arranged in the nursing facility or by using the swallowing choke detection device 460. Various modifications can be made in view of which device performs the processing shown in FIG. 14.

First, in the step S401, the processing unit 210 of the second terminal device 200B acquires table information which is related to the medicine prescribed to the target patient. The table information is information associated with, for example, the ID identifying the target patient, the timing of taking the medicine, the name of the medicine, and the dose of the medicine one time. By referring to the table information, it is possible to identify the type and amount of the medicine for each patient and for each timing. For example, the server system 100 may store the table information as part of the electronic medical record, etc., and the second terminal device 200B may perform processing to acquire the table information from the server system 100.

In the step S402, the processing unit 210 of the second terminal device 200B identifies the target patient and the timing the target patient have to take the medicine. For example, a user ID that uniquely identifies the target patient is set in the nursing facility or the like, and a bar code or QR code (registered trademark) representing the user ID may be generated in advance. In this case, for example, the second terminal device 200B identifies the target patient by acquiring images of the bar code or QR code using the imaging unit 260 of the second terminal device 200B. The second terminal device 200B also identifies the timing the target patient have to take the medicine by receiving, for example, the input of the operation unit 250 by the care assistant. For example, the care assistant uses the operation unit 250 to input and select any one of several candidates, such as a timing before meal at breakfast, a timing after meal at breakfast, a timing before meal at lunch, a timing after meal at lunch, a timing before meal at dinner, a timing after meal at dinner, a timing before meal morning snack, a timing after meal at morning snack, a timing before meal at afternoon snack, a timing after meal at afternoon snack, a timing the target patient is waking up, or a timing the target patient is going to bed, etc. It should be noted that both the information to identify the patient and the timing the target patient takes the medicine may be determined based on the operation input of the care assistant. Furthermore a method identifying the timing is not limited to this embodiment, other method such as using a clock data in the second terminal device 200B can be applied to this embodiment. Various modifications would be made.

Based on the table information acquired in the step S401 and the user ID and the timing acquired in the step S402, the processing unit 110 can identify the amount and type of medicines to be taken by the target patient. For example, the second terminal device 200B may perform processing to display the type and amount of the identified medicines on the display unit 240. The medical caregivers will prepare the necessary medicine for the target patient based on the information displayed on the display unit 240.

The second terminal device 200B then performs processing to detect the type and amount of medicines prepared by the medical caregivers. For example, a medicine ID that uniquely identifies the medicine is set in the nursing facility or the like, and a bar code or QR code representing the medicine ID may be generated in advance. For example, the medical caregiver may take the action to scan the bar code or QR code corresponding to the medicine to be prepared over the imaging unit 260 of the second terminal device 200B. The bar code or QR code may be attached to the box of the medicine or be displayed on the display unit of another terminal device. In the step S403, the second terminal device 200B determines the type of medicine prepared by the medical caregiver based on the acquired image by the imaging unit 260. The type here is the name of the medicine for example, but may include information such as the content of the active ingredient per a tablet or per a package.

In addition, the medical caregiver take out some medicines and divide the necessary amount of the medicine for the target patient, and perform the operation of imaging by the imaging unit 260. In the step S404, the second terminal device 200B determines whether the amount of the medicine divided by the medical caregiver is appropriate or not based on the image acquired by the imaging unit 260. Here, the amount of the medicine is the number of capsules or tablets, or the number of packages if the medicine is a powder. It should be noted that the above example of explaining the type of medicines using a bar code or QR code has been explained, but this embodiment is not limited to this example. For example, the type of medicine may be identified based on image recognition such as characters printed on the box or characters printed on the packaging sheet of the medicine. In this case, for example, both the steps S403 and S404 may be performed by acquiring images of the medicine by the imaging unit 260 of the second terminal device 200B.

In the step S405, the processing unit 210 of the second terminal device 200B determines whether there is any error by comparing the type and amount of the medicines identified from the table information with the type and amount of the medicines detected in the steps S403 and S404. For example, if a type of the prepared medicine is not included in the table information, or if the amounts of the prepared medicine do not match with the amount in the table information, or both, the processing unit 210 determines that there is error or incorrect about the prepared medicine (the step S405: error). In this case, in the step S406, the processing unit 210 performs processing to display guidance or instruction on the display unit 240, etc., and then returns to the processing in the step S403. For example, in the step S406, the difference between the correct answer and a status of the prepared medicine is displayed on the display unit 240, such as the type of medicine is different or the amount of medicine is too much or too little. The medical caregivers will re-prepare the medicine based on the guidance or the instruction displayed on the display unit 240.

If the type of the prepared medicine is included in the table information and the amount of the prepared medicine also matches with the amount in the table information, the processing unit 210 determines that there is no error that the prepared medicine is correct (the step S405: correct). In this case, in the step S407, the processing unit 210 determines whether all types of the medicines have been prepared. For example, in the case that the target patient takes multiple medicines in a single dose (one time), even if one type of the medicine is prepared (the step S405: correct), the other types of the medicine is insufficient. If all types of the medicines are not available in this way (the step S407: No), in the step S408, the second terminal device 200B displays the guidance or the instruction on the display unit 240 that the preparation of the medicines is not completed and returns to the step S403. In the step S408, the second terminal device 200B may perform processing to display the type and amount of the medicines that are lacking.

If all types of the medicines are prepared (the step S407: Yes), in the step S409, the second terminal device 200B performs processing to output a barcode or QR code associated with the target patient and the timing. For example, the second terminal device 200B is electrically connected or communicable to a printer for printing the barcode or QR code through a network, and the processing unit 210 performs processing to instruct the printer to print the barcode or QR code in the step S409. Alternatively, the second terminal device 200B may perform processing to transmit the barcode data to another terminal device 200 or the like.

Figure 15A:
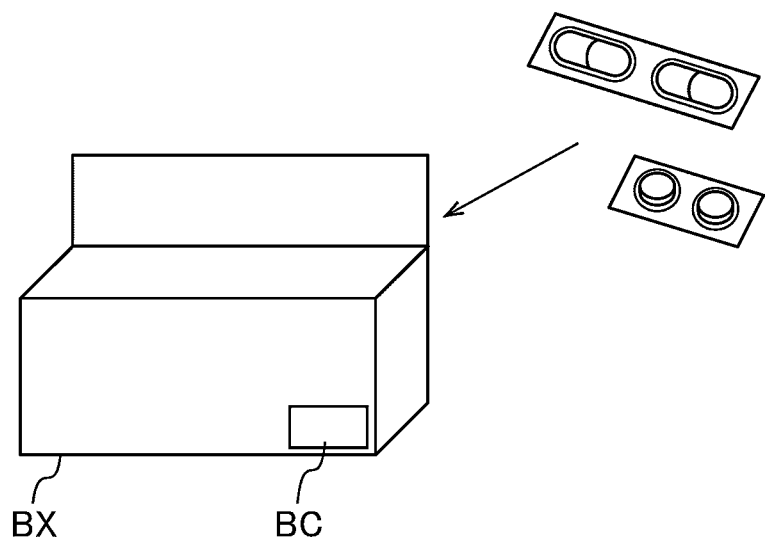
FIG. 15A is a schematic diagram illustrating the procedure of a medication preparation.
Figure 15B:
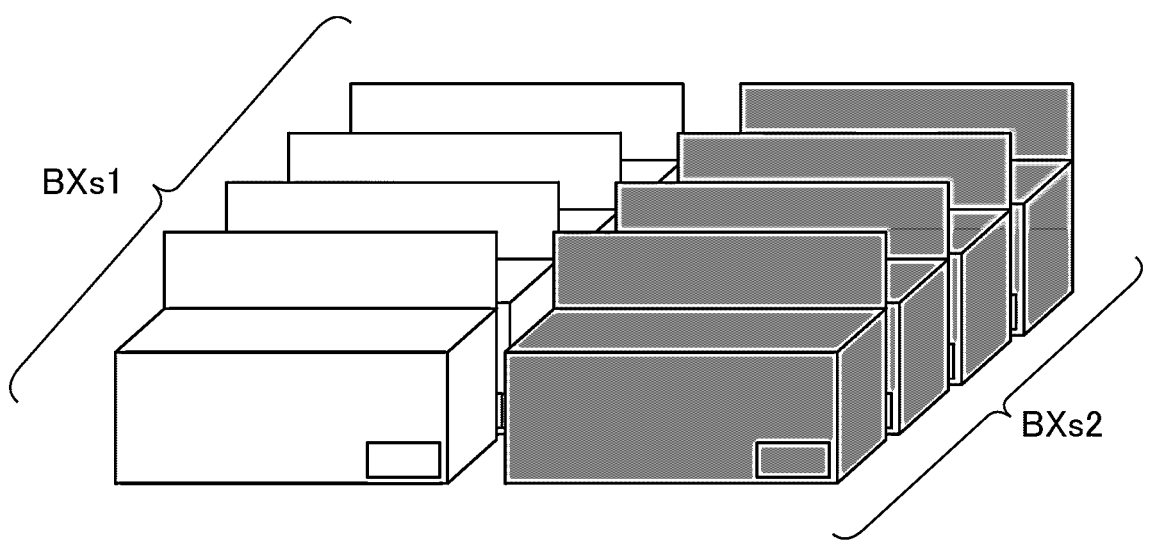
FIG. 15B is a schematic diagram illustrating the procedure of the medication preparation.

The FIGS. 15A and 15B are schematic diagrams illustrating the method of managing medicines in the nursing facility or the like. For example, as shown in FIG. 15A, the medical caregiver puts the medicines prepared through the process shown in FIG. 14 into a container BX and attaches a code BC output in the step S409 to the container BX. The code BC may be the barcode or the QR code as described above. This ensures that prepared medicines that one target patient should take at a given timing are stored together in one container BX. The container BX may stock the package which necessary medicine the target patient will take one time is packed.

For example, in the nursing facilities, a plurality of containers BX for a plurality of target patients may be stored together for each timing as shown in FIG. 15B. For example, the plurality of containers BXs1 in FIG. 15B are a set of the containers BX for storing the medicines to be taken after breakfast, each container corresponds to each target patient. Similarly, the plurality of containers BXs2 in FIG. 15B are a set of the containers BX for storing medicines to be taken after dinner, each container corresponds to each target patient. For example, the different colors, shapes, etc. of multiple containers BXs1 and multiple containers BXs2 make it possible to clearly indicate the timing of taking the medicine, making it easier to determine which container BX should be taken to the target patient.

The care assistant selects the appropriate container BX from the multiple containers BX shown in FIG. 15B based on the target patient in charge and the current timing, and performs the medicine assistance to have the patient in charge take the medicine in the container BX. The medicine management processing supporting the medicine assistance is described below.

Figure 16:
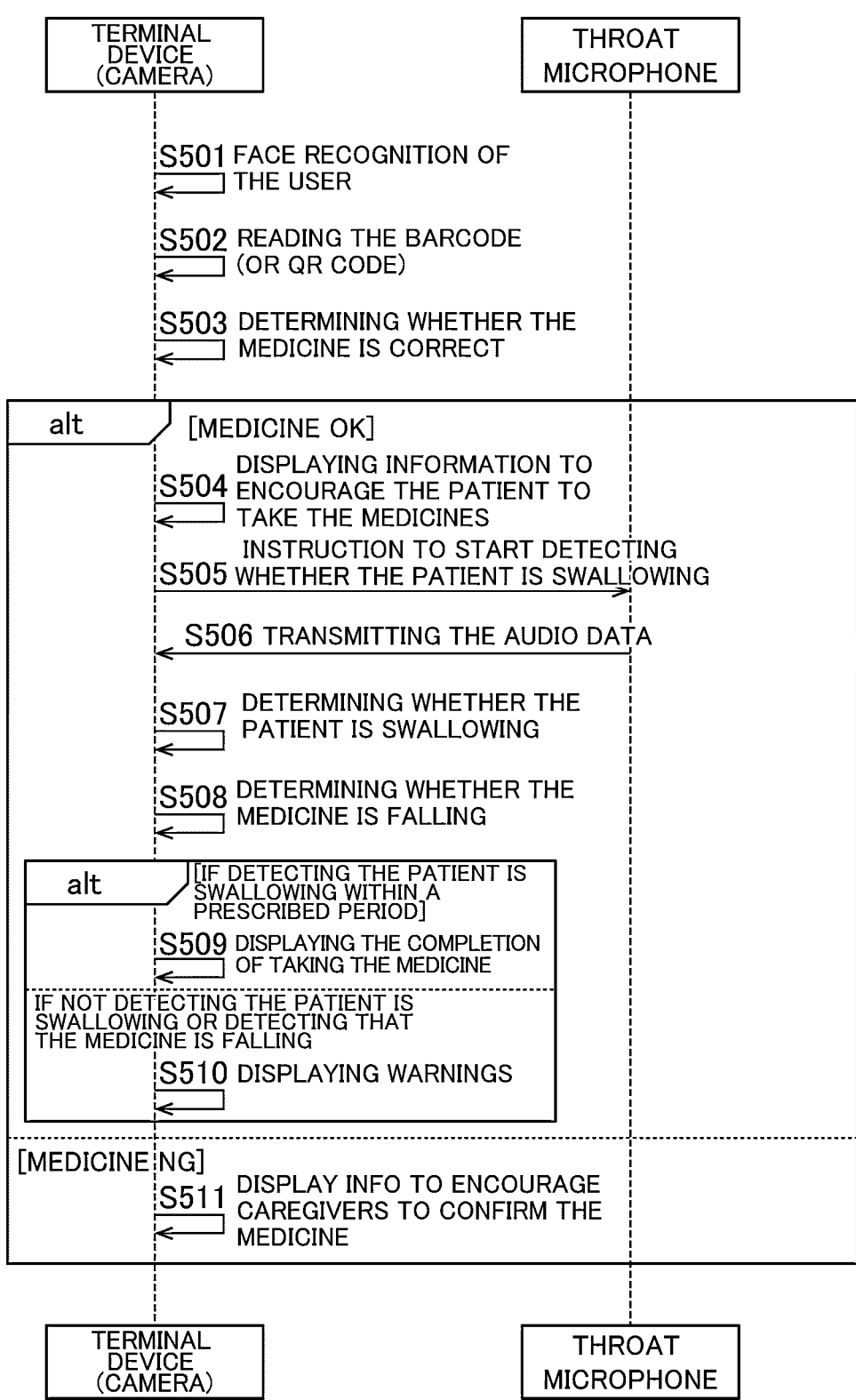
FIG. 16 is a sequence diagram illustrating the medication management processing.

The FIG. 16 is a sequence diagram illustrating the medicine management processing using the swallowing choke detection device 460. The swallowing choke detection device 460 includes the throat microphone 461 as described above and a terminal device 462 with a camera. In the following, an example is described in which the terminal device 462 performs various processing such as image recognition, but these processing may be performed by a processing unit 110 or the like of the server system 100.

Firstly, in the step S501, the terminal device 462 performs processing of a face recognition of the target patient using the camera. The FIG. 17 is a screen example displayed on the terminal device when the terminal device performs processing of the face recognition of the target patient. In the following, the screen example displayed on the display unit of the terminal device 462 is described below, but the screen shown in FIG. 17 or the like may be displayed on other devices such as the second terminal device 200B.

Figure 17:
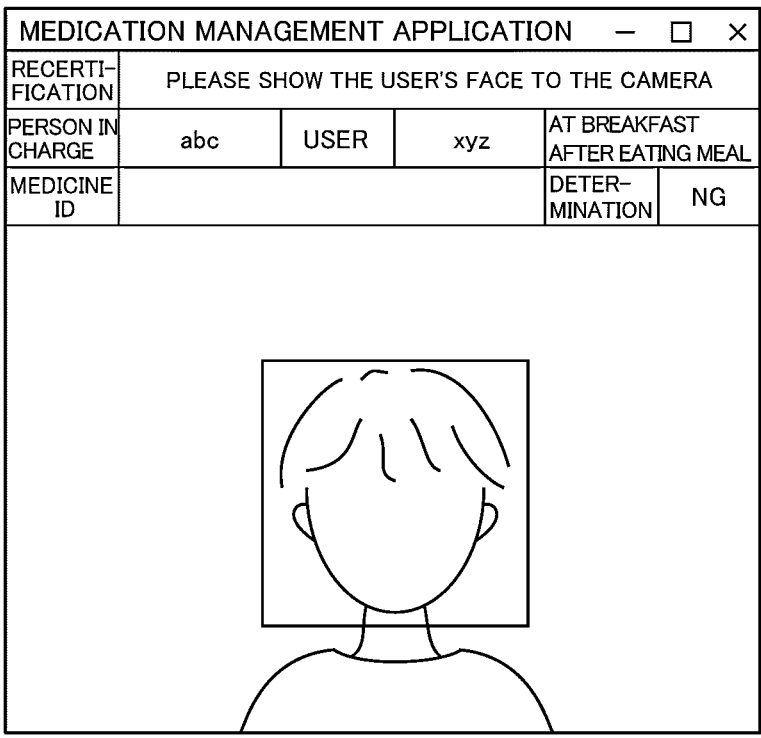
FIG. 17 shows a screen example to perform a face recognition processing in medication management.

As shown in FIG. 17, the screen for processing of the face recognition includes the text "Please show your face on the camera" and an area for displaying the acquired image of the camera. The care assistant may adjust the location and the angle of the terminal device 462 so that the target patient's face is positioned within the images acquired from camera. Alternatively the care assistant may change the target patient's sitting position or the target patient's posture, or assist the target patient re-sit on the wheelchair so that the target patient's face is positioned within the images acquired from camera The processing unit of the terminal device 462 recognizes the target patient's face using known face recognition techniques or known object recognition techniques. For example, the server system 100 stores the face image data of the target patients in each facility and the feature quantities extracted from the face image data in association with the target patients. The terminal device 462 acquires the information stored in the server system 100 as template data and performs processing of the face recognition by comparing the template data with the acquired image. In the example in FIG. 17, as a user (the patient), the target patient with the name 'xyz' is detected. In addition, as shown in FIG. 17, in view of the medicine management, the terminal device 462 may receive the information about the caregiver in charge of the target patient (in a narrow sense, the care assistant). In the example of FIG. 17, as the care assistant in charge of the target patient, the care assistant with the name "abc" has been entered. The information about the care assistant in charge of the target patient may be entered on the basis of user operation or by processing of the face recognition based on acquired images as in the above example.

Also, in the step S501, the terminal device 462 may receive the information about the timing the target patient will take the medicines by inputting the information identifying the timing as shown in FIG. 17. For example, if the terminal device 462 receive the input operation about the timing on the input area in FIG. 17 (the area where "during breakfast—after meal" is displayed), multiple candidates for the timing may be displayed in a pull-down menu on the input area. The care assistant may select one of them based on the current timing. The processing unit of the terminal device 462 identifies the timing based on the input operation. Hereafter, an example in which after-meal at lunch is selected in the step S501 will be described.

Figure 18A:
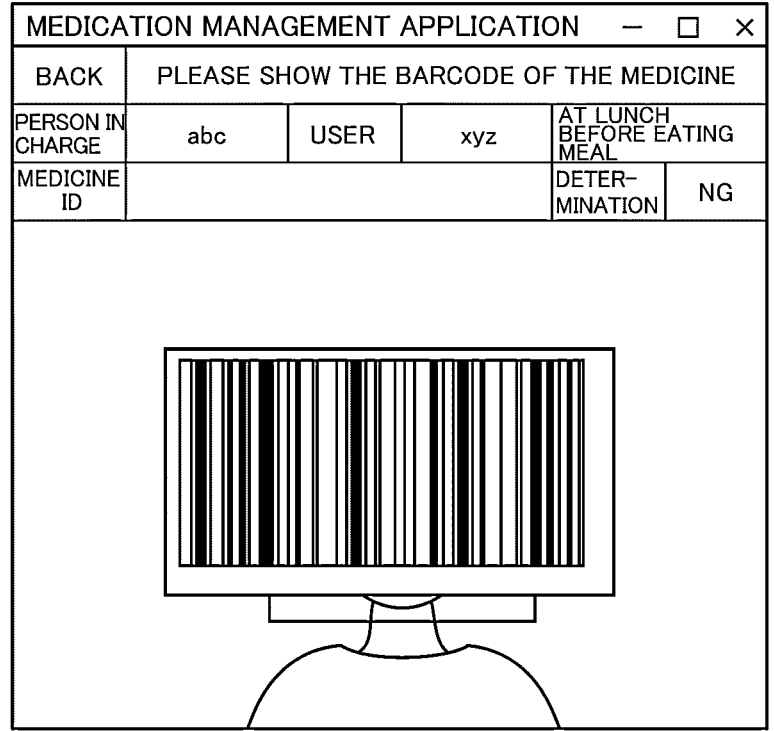
FIG. 18A shows a screen example to perform a barcode recognition processing in medication management.

Next, the processing unit of the terminal device 462 performs processing to read the code BC attached to the container BX. The FIG. 18A is a screen example displayed on the terminal device if the terminal device performs processing of the barcode recognition of the medicine. As shown in FIG. 18A, the screen for processing of the barcode recognition includes the text "Scanning the barcode of the medicine" and an area to display the captured image of the camera. The care assistant moves the container BX so that the code BC of the container BX comes in front of the camera for example. The processing unit of the terminal device 462 identifies the target patient for whom the medicine in the container BX has been prescribed and the timing the target patient will take the medicines by reading the code BC.

In the step S503, the terminal device 462 determines whether the prepared medicines is correct or incorrect. Specifically, the terminal device 462 identifies the target patient in front of the camera based on the processing in the step S501 and the timing the target patient should take the medicines by the assistance of the care assistant, and identifies the patient associated with the medicines and the timing the target patient should take the medicines based on the reading result in the step S502. The terminal device 462 determines that the medicines to be taken is correct if the patient identified in the step S501 matches with the patient identified in the step S502 and the timing identified in the step S501 matches with the timing identified in the step S502, and determines that the medicines to be taken is incorrect if the patient identified in the step S501 does not match with the patient identified in the step S502, the timing identified in the step S501 does not match with the timing identified in the step S502, or both. The terminal device 462 may display the determination result, for example, in a determination area shown in FIG. 18A. The FIG. 18A shows the situation before reading the bar code, and the terminal device 462 displays the determination result indicating "NG" in the determination area.

If the terminal device determines that medicines to be taken is correct (the sign indicating "medicines OK" in FIG. 16), the terminal device 462 notifies a notification to encourage the target patient to take the medicines in the step S504. For example, the terminal device 462 may display a text information to encourage the target patient to take the medicines on the display of the terminal device 462 or may output an audio information to encourage the target patient to take the medicines using a speaker. The FIG. 18B shows a screen example on the display unit of the terminal device if the terminal device determines that medicines to be taken is correct. As shown in FIG. 18B, the reading result of the bar code is displayed in a medicine ID area. Here, a bar code with the name xyz when the meal at lunch is read, and the target patient identified by the bar code and the timing identified by the bar code match the user (xyz) acquired in the step S501 and the timing input by the care assistant (e.g. the meal at lunch). Therefore, the terminal device will display the result of determination as OK in the determination area, indicating that medicines to be taken is correct. In this case, as shown in FIG. 18B, the terminal device displays a first record button to acquire video data and a second record button to acquire image data on the screen, along with the text "Press the first record button or the second record button". The first and second record buttons here are buttons to start determining whether the target patient takes the prepared medicines based on data related to whether the patient is swallowing. For example, the first record button may be a button to start a mode for recording the moving image acquired by the imaging unit of the terminal device 462 and for recording the result related to whether the patient is swallowing, and the second record button may be a button to start a mode for storing only the result related to whether the patient is swallowing without recording the moving image. If the care assistant had confirmed that the screen shown in FIG. 18B is displayed, the care assistant removes the bar code from the imaging range and selects the first record button or the second record button to start recording the data whether the target patient in charge had taken the medicines.

If the care assistant selects the first record button or the second record button, the terminal device 462 performs processing to instruct the throat microphone 461 to start tracking the audio data to determine whether the patient is swallowing in the step S505. For example, the throat microphone 461 starts acquiring the audio data based on the instruction in the step S505 and outputs the acquired audio data to the terminal device 462 in the step S506.

In the step S507, the terminal device 462 performs processing to determine whether the patient is swallowing based on the output data from the throat microphone 461. Also, the camera of the terminal device 462 continues to acquire the moving image of the target patient and may determine whether the medicines are falling from the table or his or her hands for example as shown in the step S508. For example, if the terminal device 462 can detect the medicines in the image by object detection, the terminal device may determine that the medicines has dropped from the hands or the table the target patient uses if the terminal device detected that the medicines is falling or moving fast based on certain thresholds.

If the terminal device detects that the target patient had swallowed within a predetermined period after encouraging or promoting the patient should take the medicines in the step S504 and the terminal device does not detect that the medicines have been falling. the terminal device 462 outputs that the medication has been completed in the step S509. The start point of the predetermined period may be, for example, the timing when the care assistant selects the first record button or the second record button. On the other hand, if the terminal device does not detect that the target patient had swallowed within the predetermined period, the medication may not have been completed. Also, if the terminal device detects that the medicines have been falling in the step S508 even though the terminal device detects that the target patient had swallowed, proper medication may not have been completed. Therefore, in these cases, the terminal device 462 activates the alarm or presents a warning to the care assistant. FIG. 19 is a screen example displayed in the step S510. In the example of FIG. 19, the terminal device may display the alarm or the warning notification indicating that the medicines have been falling with superimposing on the area where the captured image is displayed.

In addition, if at least one of the patient identified in the step S501 does not match with the patient identified in the step S502 and the timing identified in the step S501 does not match with the timing identified in the step S502, in the processing of the step S503 (the sign indicating "medicines NG" in FIG. 16), in the step S511, the terminal device 462 performs processing to present the notification to prompt and encourage the care assistant to confirm whether the prepared medicines is correct. For example, the terminal device 462 may continue to display the sign NG in the determination area shown in FIG. 18A, etc. Alternatively, the terminal device 462 may continue to display the sign NG in the determination area and may additionally display some text, etc., to encourage the care assistant to confirm at least one of whether the target patient is correct or whether the prepared medicines are correct, the timing is correct, and the medicine container BX is correct.

As described above, in this embodiment, whether or not the target patient had taken the prescribed medicines can be accurately determined by using whether the target patient had been swallowing or not. The processing shown in FIG. 16 is an example of the medication management, and the detailed processing is not limited to this above example. For example, in the step S501, we explained an example of specifying the timing when the target patient should take the medicines based on user input (that is, the selection from the care assistant for example), but the terminal device 462 includes a timer unit and automatically sets the timing when the target patient should take the medicines based on the current time obtained by the timing unit. Also, a text including the name of the target patient and the timing when the target patient should take the medicines may be provided as a label to the container BX, etc., and the target patient associated with the medicines and the timing when the target patient should take the medicines may be identified by performing text mining of the label in the step S502. In addition, various modifications can be made to the details of the processing.

Figure 20:
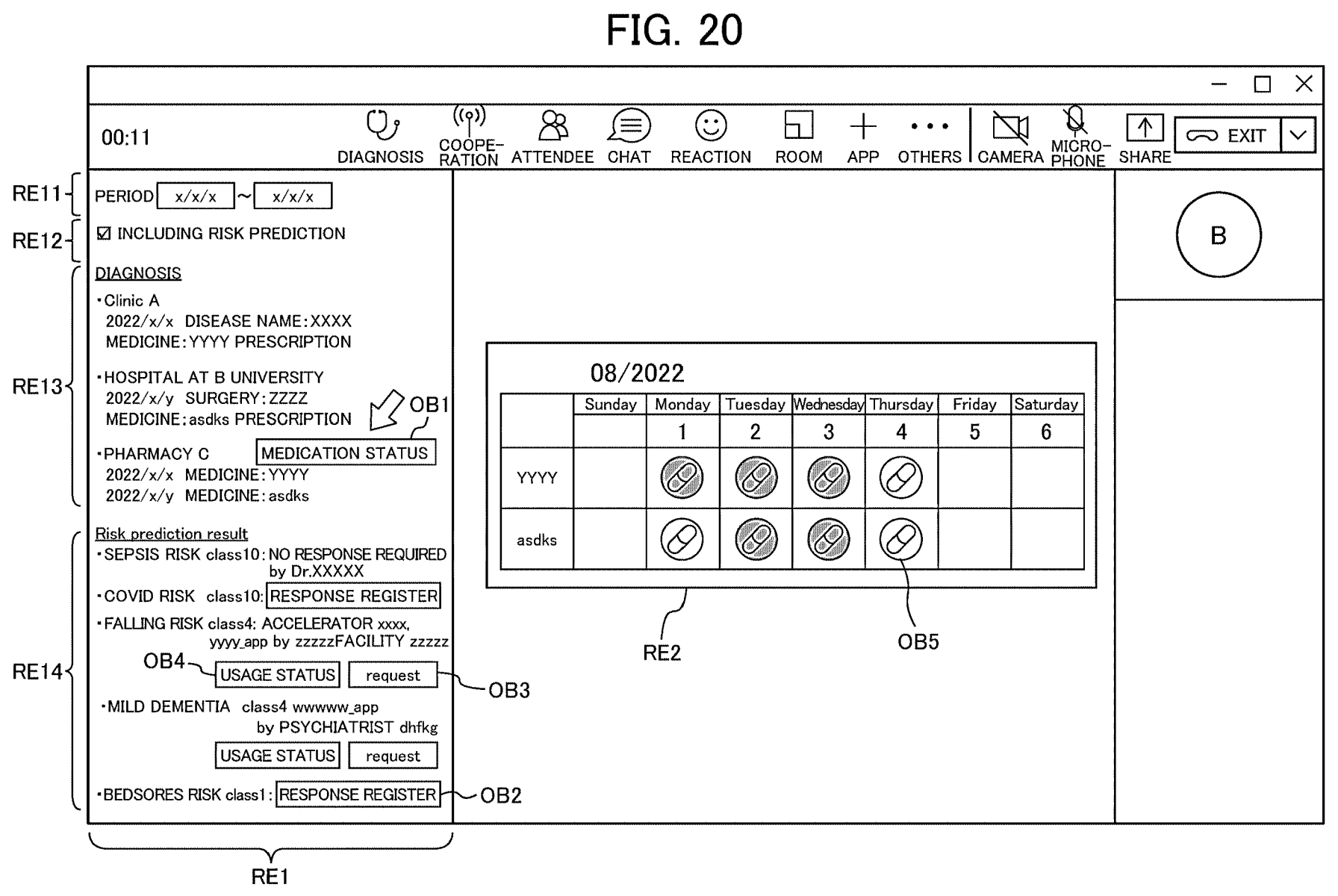

The processing unit 110 of the server system 100 may perform processing to acquire the result regarding the target patient's medication status based on the information from a camera for acquiring image of the target patient and the information from a device for detecting whether the target patient had been swallowing. For example, the processing unit 110 may acquire the result of the processing shown in FIG. 16 from the terminal device 462. Alternatively, the processing unit 110 may acquire the audio data from the throat microphone 461 and the images acquired from the terminal device 462, and perform the processing of each step shown in FIG. 16 based on the audio data and the acquired image. Then, the processing unit 110 may perform processing to make the result regarding to the target patient's medication status present in association with the medical information and assistance information on the screen of the first terminal device 200A or the second terminal device 200B. In this way, in addition to accurately determining the actual medication status based on the information from a camera for acquiring image of the target patient and the information from a device for detecting whether the target patient had been swallowing, the result regarding to the target patient's medication status can be shared among multiple specialists such as the skilled caregivers. The result regarding to the target patient's medication status is, for example, whether the medication was properly completed (processing of the step S509 was performed) or not properly completed. However, the result regarding to the target patient's medication status may include more detailed information such as whether the medicines have been falling or not For example, as shown in FIG. 11, the terminal device may display the medication status object OB1 for confirming the medication status in association with the information indicating the prescription result of the medication on the screen of the terminal device, and the screen of the terminal device may already display the medical information and the care assistance information. If the terminal device receives the selection operation of the medication status object OB1 by the medical caregiver or the care assistant, the first terminal device 200A or the second terminal device 200B notifies that terminal device receives the selection operation of the medication status object OB1 to the server system 100. The processing unit 110 may then perform processing to cause the first terminal device 200A or the second terminal device 200B to display a screen showing the target patient's medication status The FIG. 20 shows a screen example of the medication status displayed on the display unit of the first terminal device 200A or the second terminal device 200B if the caregiver selects the medication status object OB1 on the display unit. The screen example of the medication status may include, for example, an area RE2 for displaying the information indicating a medication status in addition to the area RE1 shown in FIG. 11. For example, an object OB5 representing the medication status for each day and for each medicine is displayed in the area RE2.

Here, this example shows that the target patient would take the medicine named as "YYYY" and the medicine named as "asdks" one time per day. Thus, per day, the object OB5 corresponding to "YYYY" and the object OB5 corresponding to "asdks" are shown one by one. For example, if the terminal device determined that the target patient had taken the medicines properly in the processing shown in FIG. 16 (the step S509), the object OB5 is displayed in a first mode, and if the terminal device determined that the target patient had not taken the medicines properly (the step S510, etc.), the object OB5 may be displayed in a second mode, which is different from the first mode. That is, the color or figure or shape of the object OB5 in the first mode is different from that of the object OB5 in the second mode.

In the example shown in FIG. 20, since the both two objects OB5 are displayed in the first mode on August 2 and August 3, the target patient had taken the both medicines "YYYY" and "asdks" properly. In the contrast, the object OB5 corresponding to the medicine "YYYY" is displayed in the first mode on August 1, but the object OB5 corresponding to the medicine "asdks" is displayed in the second mode on August 1. Therefore, the medical caregiver or the care assistant who had browsed this screen in FIG. 20 would understand that the target patient had taken the medicine "YYYY" properly but had not taken the medicine "asdks" properly on August 1. Also, the both two objects, OB5 are displayed in the second mode on August 4, and thus, neither the medicine named as "YYYY" nor the medicine named as "asdks" was taken properly. By displaying the screen shown in FIG. 20, the medication status can be shared among multiple specialists such as the skilled caregivers. For example, medical caregivers and the care assistants may change their response to the risk according to the medication status.

In addition, the server system 100 may transmit the information including the medication status of plurality of target patients, time series changes of the target patient's risk, and time series changes of the target patient's ADL level to the fifth terminal device 200E of the pharmaceutical company. In this way, it becomes possible to provide a statistical data that can be used to determine the effect of the medication, the effect of stopping the medication, etc., for the medicine manufactured by the target pharmaceutical company.

The results of medication management are not limited to those used to display the screen shown in FIG. 20. For example, the operating mode of the device or application may be changed based on the results of medication management. For example, if the terminal device determined that the target patient had taken the medicine properly based on the processing described above (the step S509), the terminal device or the server system 100 will instruct to start processing to the swallowing choke detection device 460, and the swallowing choke detection device 460 may initiate the processing regarding the meal assistance described above. This makes it possible to smoothly preform a medication assistance and the meal assistance, for example, in the case that the target patient should take the prepared medicine before eating the meal. In the present embodiment, if the swallowing choke detection device 460 detects the target patient had completed to eat the meal in the meal assistance, the swallowing choke detection device 460 will instruct to start processing related to the medication management to the terminal device directly or through the server system 100. The terminal device may start the processing related to the medication management automatically, and various modifications can be made to the specific action.

3.5 Tacit Knowledge

<Usage Situation of the Tacit Knowledge>

As described above using the area RE14 in FIG. 11, the information related to tacit knowledge may be displayed on a screen to share the medical information and the care assistance information in the method of this embodiment. However, the tacit knowledge is the substantially same as medication, and even if the tacit knowledge application or the tacit knowledge device 400 has already been introduced or installed to the target patient, the target patient, or caregivers cannot receive the benefit or effect from the tacit knowledge if caregivers did not use the tacit knowledge application or the tacit knowledge device 400. For example, it is important for the caregivers such as the medical caregivers or the care assistants to know the specific circumstances such as whether the tacit knowledge already introduced or installed was not effective or whether the tacit knowledge was not used in the first place if some risk regarding the target patient is detected.

Therefore, the processing unit 110 of the server system 100 may acquire information representing the usage status of the tacit knowledge from the tacit knowledge application, which is the application software corresponding to the tacit knowledge, or the tacit knowledge device 400 which performs the operation corresponding to the tacit knowledge. For example, the device installed the tacit knowledge application (the fourth terminal device 200D in a narrow sense) or the tacit knowledge device 400 can grasp the usage status of the tacit knowledge from its operation history. For example, the fourth terminal device 200D can acquire information such as a start timing, an end timing and a continuous usage period of the tacit knowledge application. Similarly, the tacit knowledge device 400 can also acquire information indicating when the tacit knowledge device 400 is active, or the start timing, the end timing and the continuous usage period of the tacit knowledge device 400. Therefore, the fourth terminal device 200D or the tacit knowledge device 400 transmits these information to the server system 100 as information indicating the usage status.

Then, the processing unit 110 may perform processing to make the first terminal device 200A and the second terminal device 200B present the usage status on the display units of the first terminal device 200A and the second terminal device 200B. In this way, it becomes possible for all caregivers not only to share the introduced or installed tacit knowledge but also to share the usage status of the tacit knowledge in details.

For example, as shown in FIG. 11, the first or second terminal device 200 may display a usage status object OB4 for confirming the usage status in association with the information representing the tacit knowledge introduced or installed by any specialist such as the medical caregiver and the care assistant on the screen which the medical information and the care assistance information may also be displayed. If the caregiver selects the usage status object OB4 on the screen of the first terminal device 200A or the second terminal device 200B, the first terminal device 200A or the second terminal device 200B transmits to the server system 100 that the usage status object OB4 is selected. The processing unit 110 may then perform processing to make the first terminal device 200A or the second terminal device 200B present or display the usage status on the screen.

Figure 21:
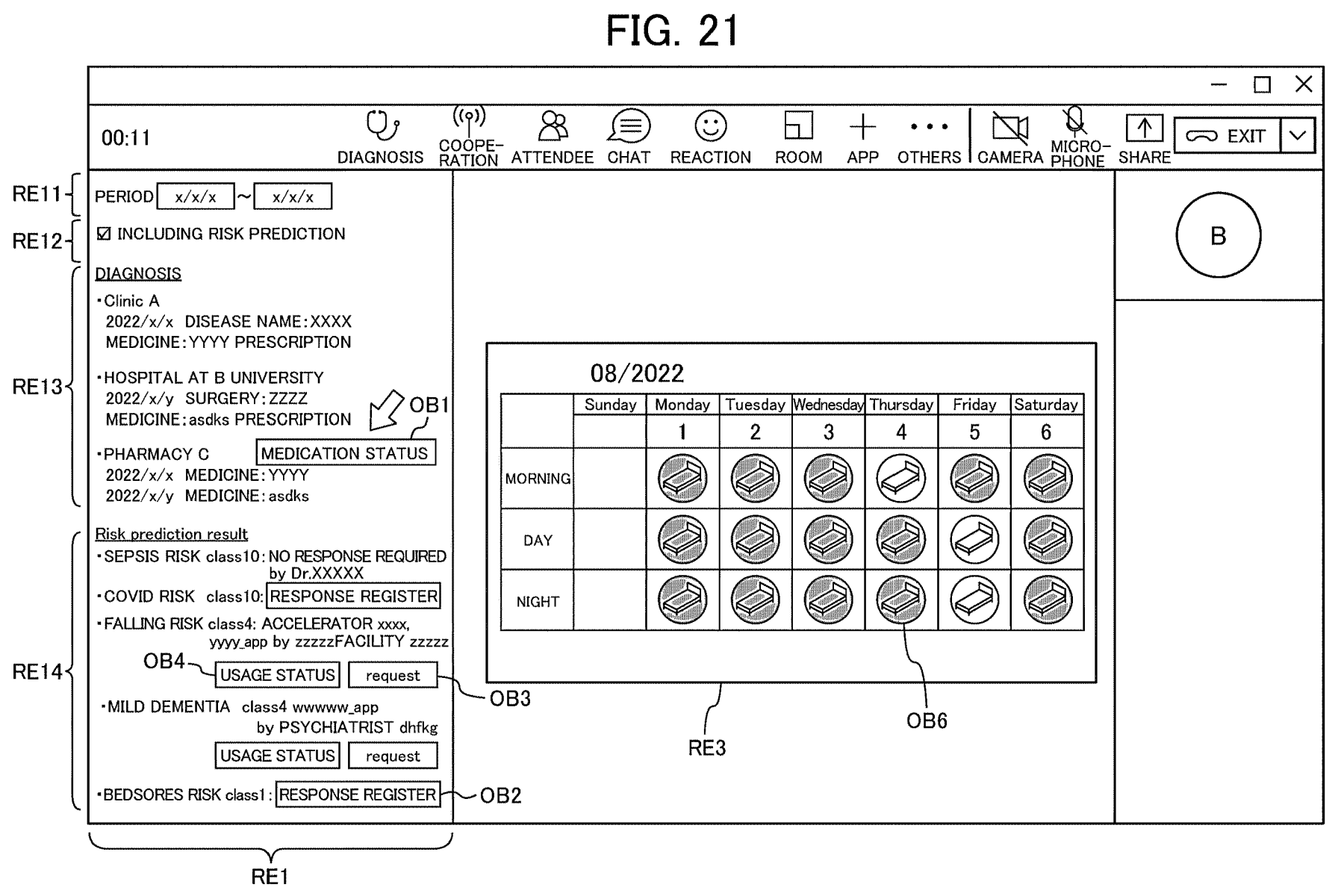

The FIG. 21 shows a screen example showing the usage status displayed on the display unit 240 of the first terminal device 200A or the second terminal device 200B if the caregiver selects the usage status object OB4 on the screen of the first terminal device 200A or the second terminal device 200B. The screen can include, for example, an area RE3 indicating the information of the usage status in addition to the area RE1 shown in FIG. 11. For example, the area RE3 displays an object OB6 representing whether or not the target knowledge is used at each timing.

For example, if the positioning application is used to support the care assistance when the caregivers may change the target patient's diaper, the timing when the caregivers change the target patient's diaper is already determined to some extent in a care assistance schedule of the nursing facilities or hospitals. For example, we consider an example in which the caregivers will change the target patient's diaper three times one day: morning, noon and night in FIG. 21. In this case, if the positioning application is used properly every time when the caregivers change the target patient's diaper, the positioning application would store a usage history of the positioning application every timing when the positioning application is activated.

Thus, for example, if the tacit knowledge is used at the appropriate timings, the object OB6 is displayed in the first mode, and if the tacit knowledge is not used at the appropriate timings, the object OB6 is displayed in the second mode. The second mode is different from the first mode.

In the example of FIG. 21, the objects OB6 corresponding to each of morning, noon, and night on August $1^{st}$ to August $3^{rd}$ are displayed in the first mode. Therefore, the positioning application is properly used to determine the posture of the target patient, the position of the target patient, the posture of the caregiver when changing the target patient's diaper, the position of the diaper, etc. In contrast, the object OB6 corresponding to the morning on August 4 is displayed in the second mode, so the positioning application is not used when changing the target patient's diaper in the morning on August $4^{th}$. Similarly, since the objects OB6 corresponding to the day and night on August 5 are displayed in the second mode, the objects OB6 in the second mode indicate that the positioning application is not used when changing the target patient's diaper.

By displaying the screen shown in FIG. 21, the usage status of the tacit knowledge can be shared among multiple specialists. For example, the medical caregiver and the care assistant may change their response to the predicted risk depending on the usage status of tacit knowledge.

<Metaverse>

Also, even if the user of the tacit knowledge application or the tacit knowledge device can know the information such as the name of the tacit knowledge and the scene which the tacit knowledge application or the tacit knowledge device should be applied, it is not easy to concretely understand how the tacit knowledge application or the tacit knowledge device operates unless that user is a skilled person or a highly skilled specialist in the same field. For example, even if the information that the tacit knowledge created by a care manager who is a specialist in the field of the care assistance is used to support the target patient is shared among a plurality of caregivers such as nurses in a different filed from the care assistance, the nurses for example may not be able to understand or grasp the operation of the tacit knowledge application or the tacit knowledge device. Moreover, since it is not always the case that the specialist has introduced the tacit knowledge device 400, for example there is a case that the caregiver who do not have highly skill for the care assistance uses the tacit knowledge device 400, so it is not easy to directly experience the operation of the tacit knowledge device in accordance with the tacit knowledge.

Therefore, the processing unit 110 of the server system 100 may preform processing to let the user of the first terminal device 200A or the second terminal device 200B experience the tacit knowledge which is already registered in the server system 100 or selected by the user in a virtual space if the first terminal device 200A or the second terminal device 200B receives a request to experience the tacit knowledge on the screen of the terminal device displaying the medical information and the care assistance information.

For example, although the experience object is not displayed in FIG. 11, FIG. 20, and FIG. 21, the experience objects in association with the tacit knowledge may be displayed in the region RE11. For example, the experience objects may be displayed side by side with the request object OB3 and the usage status object OB4. If the first terminal device 200A or the second terminal device 200B receive the input to select the experience objects, the first terminal device 200A or the second terminal device 200B may transmit to the server system 100 that the terminal device receives the input to select the experience objects.

For example, the user of the first terminal device 200A or the second terminal device 200B may introduce or install a goggle-type device VRG that displays VR (Virtual Reality) images. The Goggle-type device VRG here is a device that outputs, for example, two parallax images to each of the user's right and left eyes. Hereafter, we will describe the device VRG having a communication function and an image processing function in the following example. However, the device VRG may be a device to which the first terminal device 200A or the second terminal device 200B can be attached and which outputs the two parallax images displayed on the display unit 240 to each of the right and left eyes using a lens. In this case, the communication processing and the image processing may be performed by the first terminal device 200A or the like.

For example, if the processing unit 110 of the server system 100 receives a request to experience the tacit knowledge, the processing unit 110 generates 3D data corresponding to the tacit knowledge and performs processing to transmit the 3D data to the device VRG. The device VRG calculates the position and posture of the virtual camera on the basis of the input from the user using the change of the posture of the user and the operation unit, and generates and outputs the two parallax images, which is two-dimensional image data, on the basis of the calculation result. Alternatively, the server system 100 may create the virtual space to experience the selected tacit knowledge in a virtual space constructed online such as a metaverse. The device VRG may display the information corresponding to the tacit knowledge by utilizing the metaverse through the communication unit.

Figure 22:
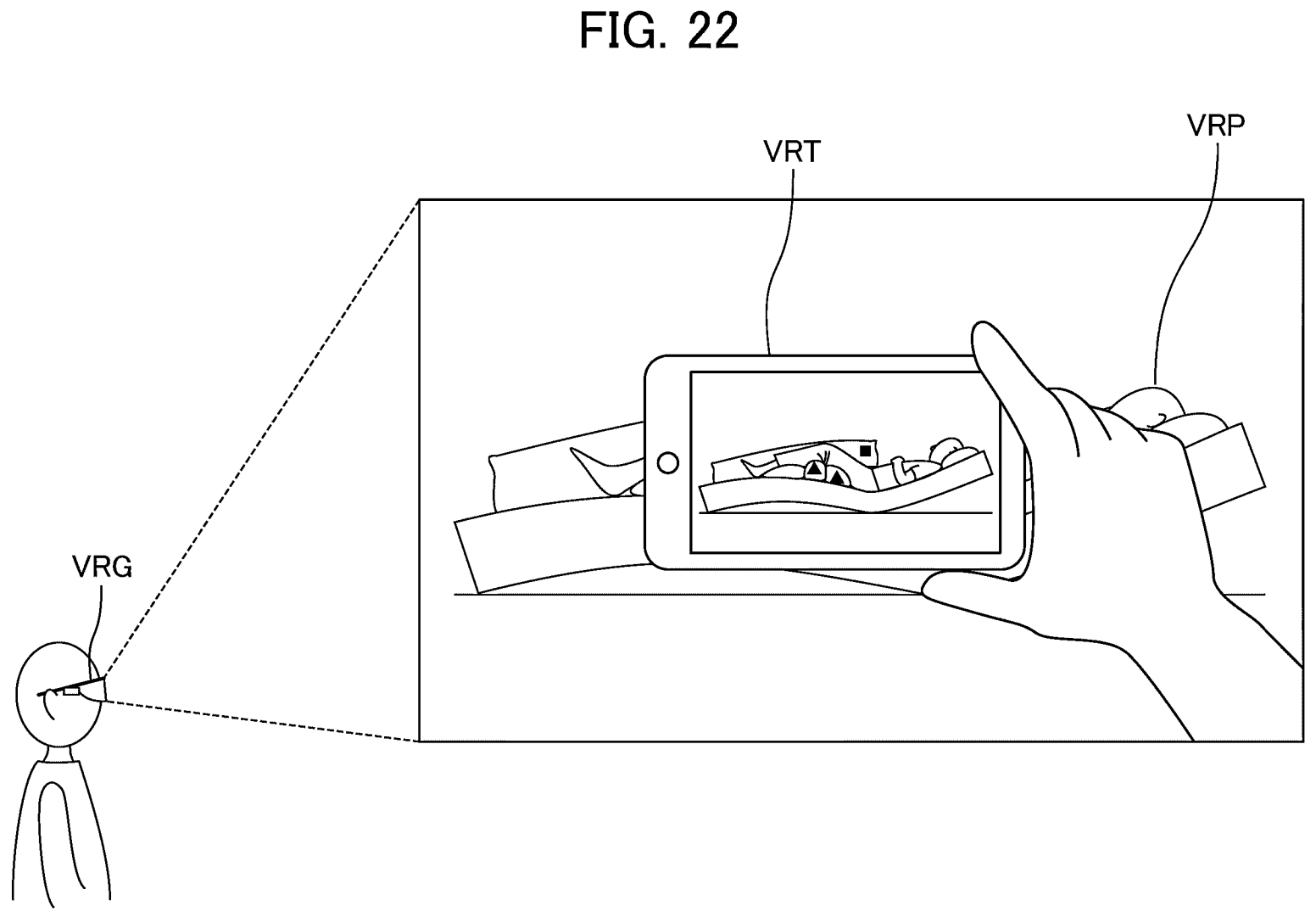

The FIG. 22 is a schematic diagram illustrating an experience method in the virtual reality space. For example, we will consider a case where a medical caregiver or a care assistant makes a request to experience the positioning application to adjust the position or the posture of the target patient who is lying in the bed. In case that the caregiver wants to experience the positioning application, if the user holds a terminal device such as a smartphone in his or her hand and acquires the images of the target patient, estimated and transparent correct data is superimposed on the acquired image as described above using, for example, FIGS. 8A and 8B.

In the example of FIG. 22, a virtual patient VRP and a virtual user are in the virtual space, and the virtual user holds a virtual terminal device VRT such as the smartphone. In this case, the virtual user can check out how the tacit knowledge application or the tacit knowledge device is used such as the correct answer data (transparent correct data) looks when using tacit knowledge by performing operations such as changing the position or the posture of the virtual patient VRP in the bed, moving around the virtual patient VRP, and moving the virtual user's arm holding the virtual terminal device VRT.

In addition, when the positioning application has a function for determining whether the position or the posture of the patient is correct or not compared with the transparent correct data as OK or NG, the user may obtain the determination result as OK or NG by performing an operation to change the posture of the virtual patient VRP and then performing an operation to acquire images of the virtual patient VRP with the virtual terminal device VRT. In this way, it is possible to confirm in the virtual space the criterion such as in what case the determination result would be OK when the user uses the selected tacit knowledge.

<Tacit Knowledge Search>

In addition, the method of this embodiment may be used or applied to the cases in which medical caregivers such as the doctor conduct remote diagnosis (telemedicine) of target patients and the care assistants conduct remote care of target patients. In this case, since there are no geographical restrictions about the telemedicine or the remote care, the telemedicine and remote care may be conducted across countries. However, different countries have different languages and cultures. Therefore, if the tacit knowledge is used or selected, for example, as the response to the predicted risk, it may be difficult for the caregivers such as doctors to decide which the tacit knowledge to use. For example, if an American doctor encourages Japanese target patients to use the tacit knowledge, the doctor may have knowledge which the tacit knowledge to use that is widely used in the United States, but that tacit knowledge used in the United States may not be suitable for the Japanese target patients due to linguistic and cultural factors for example. Therefore, in the present embodiment, the processing unit 110 may perform processing to search appropriate tacit knowledge required by the user, who is the medical caregiver or the care assistant, based on a search request by the first terminal device 200A or the second terminal device 200B, and perform processing to display the search result on the display unit of the first terminal device 200A or the second terminal device 200B. Thus, the processing to search appropriate tacit knowledge can support the selection of tacit knowledge by the medical caregiver or other caregivers.

Figure 23:
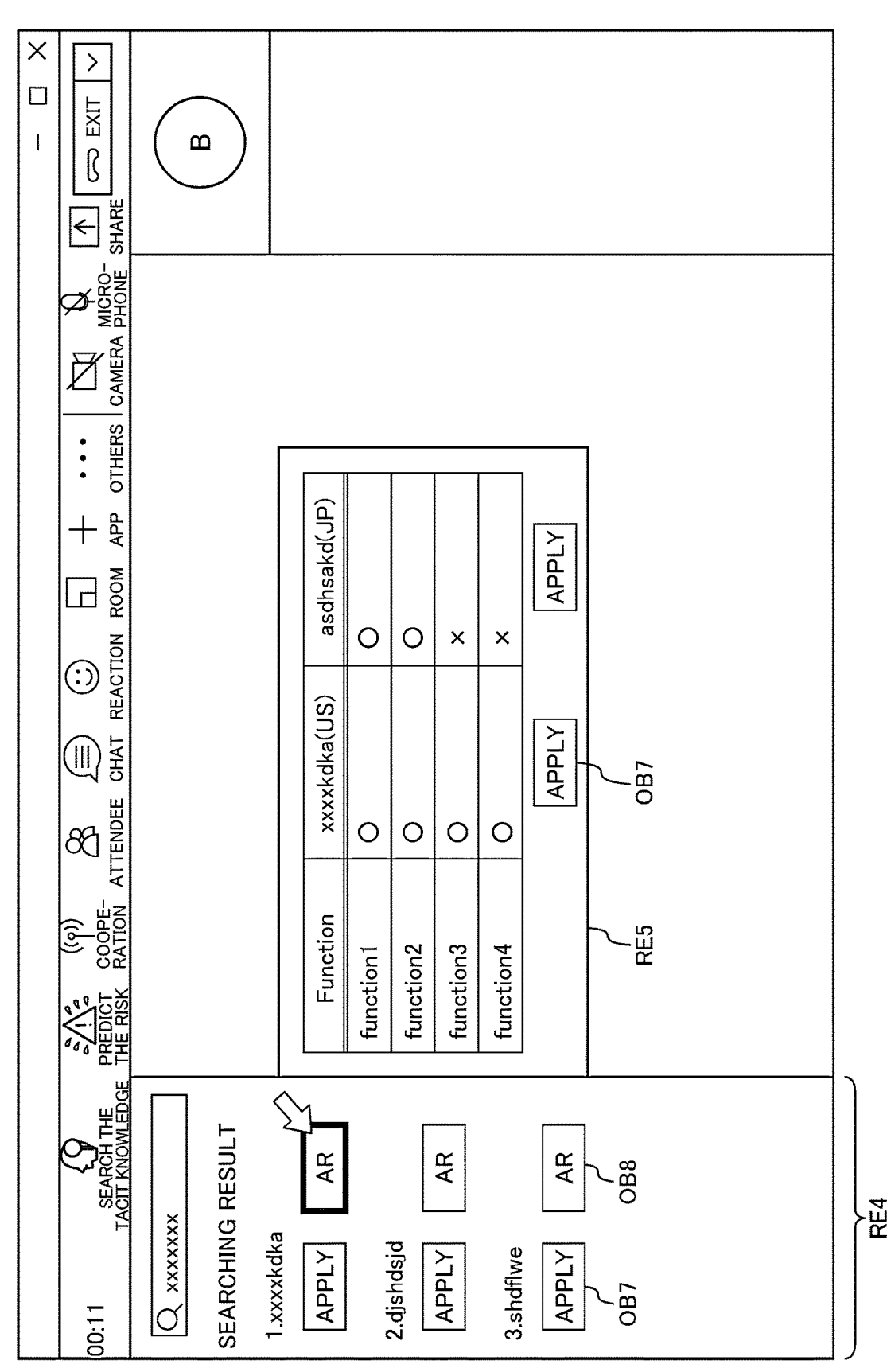
FIG. 23 is a screen example to display the search results of tacit knowledge.

The FIG. 23 shows a screen example of searching the tacit knowledge displayed on the first terminal device 200A and the second terminal device 200B. The processing to search the tacit knowledge is activated, for example, if caregivers select an icon to search the tacit knowledge, which is displayed at the top of the screen. When the processing to search the tacit knowledge is activated, the screen includes a text box for entering a search keyword and an area RE4 for displaying a search result based on the search keyword.

For example, the caregiver enters a purpose of the tacit knowledge such as "fall prevention" into the text box. The processing unit 110 performs processing to search the tacit knowledge using the relevant "fall prevention" as a search keyword and returns the search result. The first terminal device 200A and the second terminal device 200B display the search result under a text box in the area RE4. In the example of FIG. 23, three tacit knowledge are displayed as the search result: "xxxxkdkaj," "djshdsjd", and "shdflwe".

An application object OB7 and a similar object OB8 may be displayed in association with each search result in the area RE4. If the caregivers select the application object OB7, the tacit knowledge corresponding to the application object OB7 is applied to the care assistance for the target patient. For example, in a case that the caregivers select a certain tacit knowledge (the certain tacit knowledge application or the certain tacit knowledge device) as a response to the predicted risk, the certain tacit knowledge selected by the application object OB7 may be transmitted to the server system 100 as the response how to deal with the predicted risk.

Also, if the caregivers select the similar object OB8, the server system 100 may perform processing to search an another tacit knowledge similar to the selected tacit knowledge and send the search result to the first terminal device 200A or the second terminal device 200B. For example, the processing unit 110 transmits to the first terminal device 200A or the like the tacit knowledge that is highly similar to the search result among the tacit knowledge that is widely used in the region of the patient or among the tacit knowledge that is widely used for patients with attributes similar to the target patient. In this case, the processing unit 110 may determine the similarity by comparing the functions between plurality of the tacit knowledge and the selected tacit knowledge. The processing unit 110 may also transmit the information comparing the functions of between each tacit knowledge and the selected tacit knowledge together.

The function described here is a function implemented in the tacit knowledge, and for example, the processing unit 110 may transmit the information indicating whether each tacit knowledge has each of the multiple functions widely used in the medical or the care assistance field. For example, in the case of tacit knowledge for the purpose of fall prevention, the functions such as a function to determine whether the posture of the target patient is good or not in the standing position, a function to determine whether the posture of the target patient is good or not in the sitting position, a function to determine whether there is the possibility of falling or not, and a function to notify the notification to encourage or prompt the caregiver to intervene are considered, and which functions are applied to the tacit knowledge may differ depending on tacit knowledge.

For example, in FIG. 23, a doctor who is a medical caregiver lives in the United States, and as the search result, the doctor had obtained the tacit knowledge of "xxxxkdka", which is widely used in the United States. However, since the patient lives in Japan, the doctor wants to know the tacit knowledge which is similar to the tacit knowledge of "xxxxkdka" and is applicable to the Japanese patients. In this case, the processing unit 110 performs processing to search the tacit knowledge which is in the same field as the tacit knowledge "xxxxkdka", is widely used in Japan, and has a function similar to the tacit knowledge "xxxxkdka", based on the operation of the similar object OB8 input by the doctor. For example, the processing unit 110 may search another tacit knowledge which has the same or similar function to that of the tacit knowledge "xxxxkdka". Here, the processing unit 110 specifies the tacit knowledge "asdhsakdj" as the tacit knowledge which satisfies the condition, and sends the information comparing the function of the tacit knowledge "xxxxkdka" with the function of the tacit knowledge "asdhsakd" to the first terminal device 200A.

For example, the screen to show the search result of the tacit knowledge shown in FIG. 23 includes an area RE5 to display the comparison result of the functions. The function of the tacit knowledge that corresponds to the search result (e.g., "xxxxkdka") and the function of the tacit knowledge (e.g., "asdhsakd") as the reference are comparatively displayed in the area RE5. In the example of FIG. 23, the tacit knowledge "xxxxkdka" has all functions 1 to 4. On the other hand, the tacit knowledge "asdhsakd" has only the functions 1 and 2, but does not have any functions 3 and 4.

The doctors may select the tacit knowledge from plurality of tacit knowledge based on the display of the area RE5. For example, if the doctors consider that the functions 1 and 2 are relatively importance compared to the functions 3 and 4 and the functions 3 and 4 are relatively not importance compared to the functions 1 and 2, the doctors may decide to apply the tacit knowledge "asdhsakd" to the target patient. For example, if the doctors select the application object OB7 (in the area RE5) associated with the tacit knowledge "asdhsakd", the tacit knowledge "asdhsakd" is selected as the tacit knowledge to be used for the target patient. On the other hand, if the doctors consider that the functions 3 and 4 are relatively importance compared to the functions 1 and 2, the doctors may consider to select the tacit knowledge 'xxxxkdka' to be preferable and to be used for the target patient, even considering regional differences. For example, if the doctors select the application object OB7 (in the area RE4 or the area RE5) associated with the tacit knowledge "xxxxkdka", the tacit knowledge "xxxxkdka" is selected as the tacit knowledge used for the target patient. The doctors may also select search results other than the tacit knowledge "xxxxkdka" or other tacit knowledge to be functionally compared with the search results.

<Estimated ADL and Tacit Knowledge>

Figure 24:
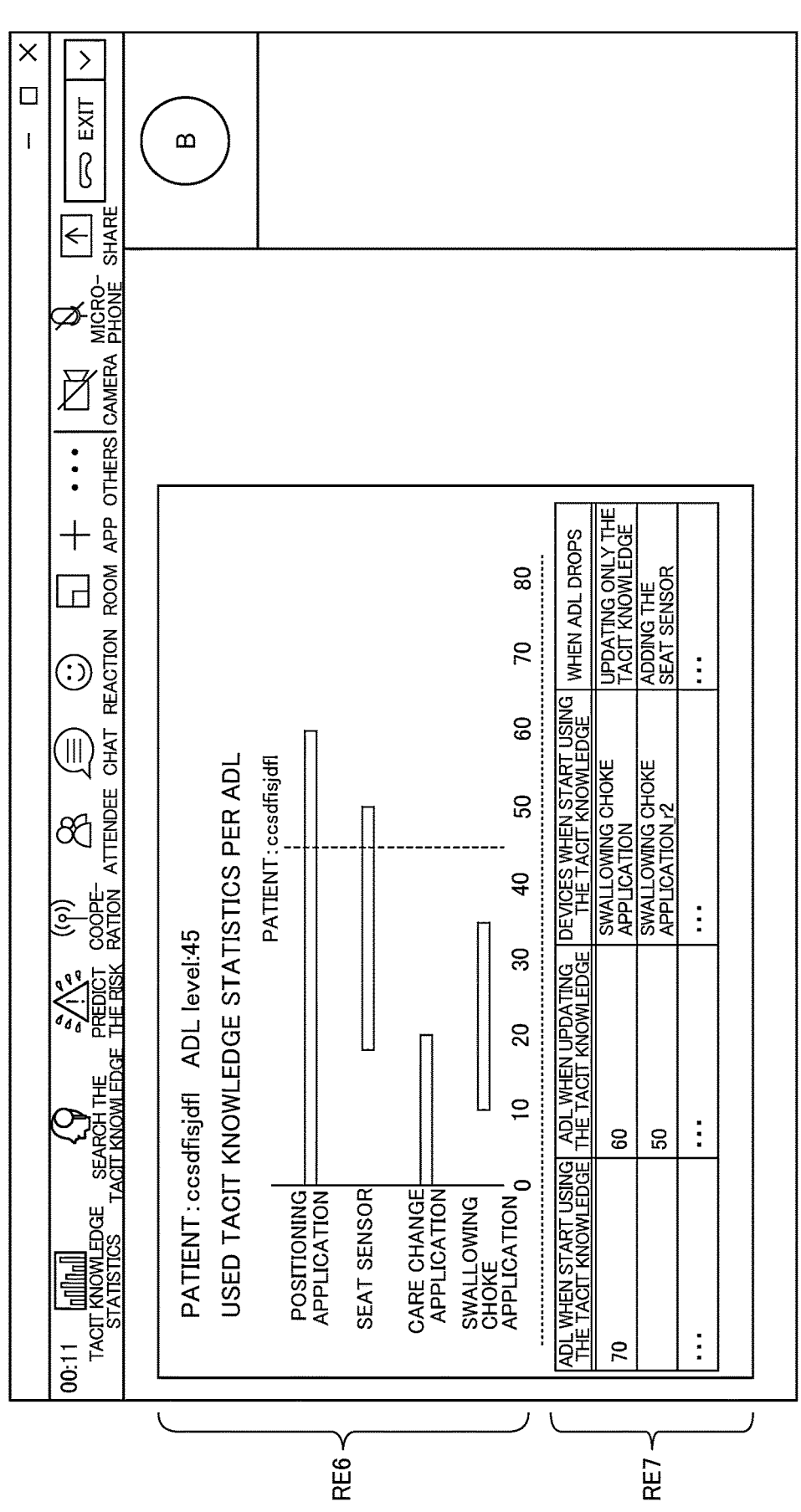
FIG. 24 is a screen example to display the relationship between ADL and tacit knowledge.

The FIG. 24 is a screen example displayed in the terminal device 200 such as the first terminal device 200A and the second terminal device 200B, and the screen example showing the relationship between the ADL level and the tacit knowledge. For example, if the caregivers select a tacit knowledge statistics icon displayed at the top of the screen of the terminal device shown in FIG. 24, the information shown in the area RE6 of FIG. 24 is displayed. The statistical data showing what kinds of the tacit knowledge is used for each ADL level is displayed in the area RE6. For example, the processing unit 110 calculates the ADL level and what kinds of the tacit knowledge should be used for each ADL level based on the information that associates the estimated ADL for each target patient with the tacit knowledge used to the target patient.

In the example of FIG. 24, the positioning application, a care change application, and the swallowing choke application are illustrated as the tacit knowledge applications, and the seat sensor 440 is illustrated as the tacit knowledge device 400. The horizontal axis of the area RE6 represents the ADL level of the patients, and the larger the value of the ADL level is, the higher the patient's level is, that is, the patient can live on their own for the daily life.

As we can see in the example of FIG. 24, the caregiver can understand that the positioning application is used for patients with ADL levels of from 0 to around 60. Similarly, the seat sensor 440 is used for patients with ADL levels between around 20 and around 50.

The care change applications are used for patients with ADL levels of from 0 to around 20 or so. The care change applications are applications to suggest that, for example, when the terminal care (the end-of-life care) should be started based on the information how much the target patient had taken the meal and water and the information related to BMI. The terminal care represents the care assistance to a patient who is likely to die in the near future. The terminal care differs from ordinary care assistance in that it emphasizes relief from physical and mental pain and support for a dignified life for the target patient. The care change application is no limited to the above suggestion, but the care change applications estimate when the status of the target patient would be changed to the status the target patient becomes bedridden, or when the status of the target patient would be changed to the status the risk of aspiration pneumonia would be increased.

The swallowing choke applications are used for patients with ADL levels of from around 10 to around 35 for example. The swallowing choke applications are applications which can perform various processing related to the meal assistance described above based on the audio data from, for example, the throat microphone 461 or the information acquired from the camera of the terminal device 462. The swallowing choke application may be an application that operates in the swallowing choke detection device 460 (the terminal device 462 in a narrow sense), or may be an application that operates in other devices that can acquire the audio data or the images acquired from the swallowing choke detection device 460.

Also, as shown in FIG. 24, the information representing the ADL level of the target patient may be displayed in the area RE6. In the example of FIG. 24, the ADL level of the target patient is displayed as 45 along with the name of the target patient, and the position of the ADL level 45 is indicated by a dashed line in the graph. As the result of this graph, it is possible to make caregivers appropriately select a significant tacit knowledge to be applied to the target patient at the current timing. In the example shown in FIG. 24, the positioning application, the seat sensor 440, may be effective for the care assistance of the target patient at current timing, and the care change applications and the swallowing choke applications may be used in the future when the ADL level of the target patient decreases.

Also, if the caregivers select any tacit knowledge application or tacit knowledge device 400 in area RE6, that is the terminal device receives a selection operation from the user, the processing unit 110 may perform processing to display detailed information about the selected tacit knowledge application or the tacit knowledge device 400. For example, the first terminal device 200A or the like displays the detailed information in the area RE7.

The detailed information about the relationship between the tacit knowledge (tacit knowledge applications or the tacit knowledge devices) and ADL is displayed in the area RE7. For example, the information displayed in area RE7 may include the information about the history of other target patients who used each tacit knowledge. For example, the information is displayed in the area RE7 that associates the ADL level when the target patient had used the tacit knowledge, the ADL level when the algorithm or determination methods of the tacit knowledge may be changed or modified, the tacit knowledge application or the tacit knowledge device 400 introduced or installed at a starting timing, and the methods how to deal with the situation when the ADL level drops. The example in FIG. 24 shows that the target patient had introduced or installed the swallowing choke application when the ADL level of the target patient is around 70 and had updated the used tacit knowledge when the target patient's ADL level decreased to around 60. For example, this used swallowing choke application would be updated to the version "r2" when the target patient's ADL level decreased to around 60. The second line of the area RE7 shows the information after this used swallowing choke application had been updated, for example, and the column of the used device at the starting timing is updated to the version "r2" of the swallowing choke applications. The second line also shows that the target patient had introduced or installed the seat sensor 440 when the ADL level of the target patient further decreases and the ADL level becomes around 50. In this way, detailed installation and update procedures for the target tacit knowledge (including procedures for linking with other tacit knowledge) are shared among plurality of caregivers, so that it is possible to support to select the appropriately tacit knowledge by the medical caregivers or the care assistants.

It should be noted that the server system 100 in this embodiment may not only estimate the current ADL level of the target patients, but also predict how the ADL level of the target patients may drop or worsen over a certain period in the future. For example, as described above, the processing unit 110 may predict the ADL level in the future from the time-series input data by using the machine learning model or deep learning model such as LSTM or the like as a learned model to estimate the ADL level in the future. In this case, the processing unit 110 may preferentially present any applications or any devices that have high affinity with the applications or the devices that will be required in the future in the processing for presenting the search results of the tacit knowledge (FIG. 23) and in the processing for presenting statistical data of the tacit knowledge (FIG. 24).

For example, we assume that the processing unit 110 predicts the target patient's ADL level will drop or worsen in the near future, and from the degree of the drop, there is a high probability of introducing the seat sensor 440 in consideration of moving such as walking, transferring from one device to another device and eating in the wheelchair 630. In this scene where the seat sensor 440 would be used in the near future, the positioning applications has a high affinity of the seat sensor 440, because caregivers will adjust the placement of cushions in the wheelchair to prevent pressure ulcers, or adjust the posture or the position of the target patient, to suppress aspiration when the target patient is eating in the wheelchair 630. Therefore, the processing unit 110 may preferentially present the positioning applications when the target patients is expected to introduce or install the seat sensor 440 in the near future. It should be noted that the seat sensor 440 and the positioning applications are examples of the applications or the devices with high affinity, and this embodiment is not limited to this specific case and the various modification can be made.

In addition, in the above examples, we have described the examples to use the predicted results of the ADL level of the target patient in the future to present the appropriate tacit knowledge, but this embodiment is not limited to this examples. For example, the predicted results of the ADL level of the target patient in the future can be applied to propose and search for some applications or devices that do not include the tacit knowledge.

For example, if the target patient is diagnosed with MCI (Mild Cognitive Impairment), which indicates a tendency to develop dementia, the processing unit 110 may suggest introducing or installing the medication assistance devices in the future. The medication assistance device here may include a device to confirm, based on whether the target patient is swallowing, whether the target patient had taken the prescribed medicines, as described above using FIGS. 16 to 19. However, if the medication is prescribed and the target patient starts to take the prescribed medicines, there is concern about the side effects of the prescribed medicines. The side effects may be various aspects such as decreased activity, deterioration of mental state, and deterioration of sleep quality at night. Therefore, the processing unit 110 may present or display some devices preferentially to acquire these information in advance when proposing and searching for applications or devices because the processing unit 110 will monitor the daily activity, the mental state, the sleep quality, of the target patient. In this way, since the index value related to the activity etc. before the target patient takes the medicines can be stored as the index value in the normal state, the processing unit 110 can perform processing to compare the state after the target patient had taken the medicines with the normal state, etc.

4. Interface for Developers

As described above, in the information processing system 10 of this embodiment, the tacit knowledge of a skilled person is digitized and used, and the usage status is shared among plurality of caregivers such as the medical caregivers, and the care assistants. However, a range of sharing the information on the tacit knowledge is not limited to this, and these information may be output to developers who create the tacit knowledge applications or the tacit knowledge devices, etc.

4.1 Screen Examples

As shown in FIG. 4, the communication unit 130 of the server system 100 of this embodiment may communicate with a third terminal device 200 C used by a developer who creates the tacit knowledge product that includes at least one of the tacit knowledge applications, which are application software corresponding to the tacit knowledge, and the tacit knowledge device 400 that can operate based on the information digitizing the tacit knowledge. The processing unit 110 may then perform processing to present the information about other products such as the tacit knowledge products created by other developers, which are used together with the developer's tacit knowledge products, in the third terminal device 200C. In this way, each developer can acquire not only the information about its own products, but also the status of cooperation with other companies' products. Details are described below.

Figure 25:
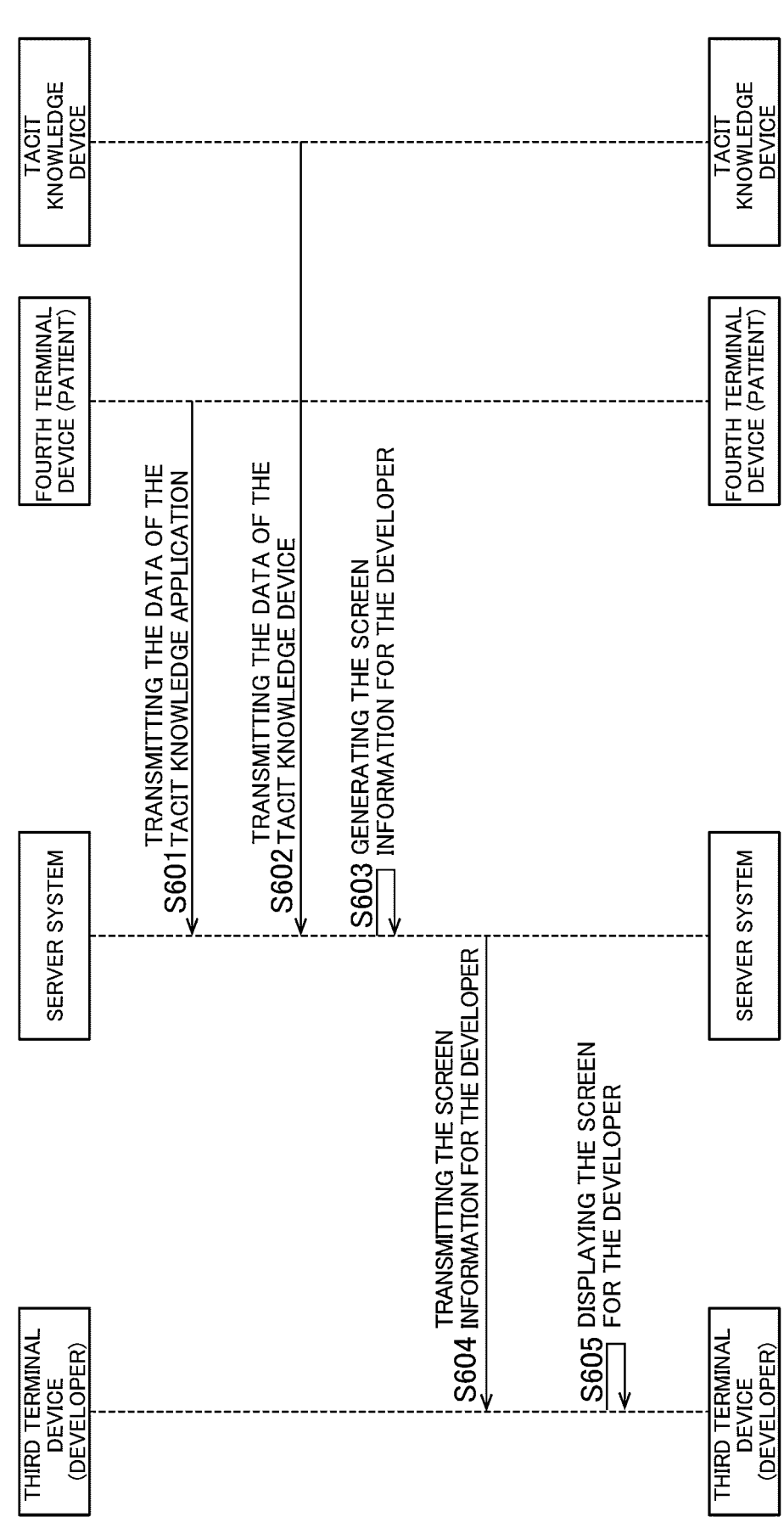
FIG. 25 is a sequence diagram illustrating the processing for developers.

The FIG. 25 is a sequence diagram illustrating the process of presenting the information to the developers. Firstly, in the step S601, the fourth terminal device 200D where the tacit knowledge application operates transmits the information representing the usage status of the tacit knowledge application to the server system 100. In the step S602, the tacit knowledge device 400 transmits the information representing the usage status of the tacit knowledge device 400 to the server system 100. In addition, the tacit knowledge applications or the tacit knowledge device 400 may transmit more detailed information such as sensing data (e.g., pressure value in the seat sensor 440) to the server system 100 in addition to the information regarding the usage status.

Thus, the processing unit 110 of the server system 100 can determine the usage status of the tacit knowledge in the tacit knowledge product. In the step S603, the processing unit 110 generates a developer screen, which is a screen for developers.

In the step S604, the processing unit 110 transmits screen information for displaying the developer screen to the third terminal device 200C via the communication unit 130. In the step S605, the processing unit 210 of the third terminal device 200C performs processing to display the developer screen on the display unit 240.

Figure 26:
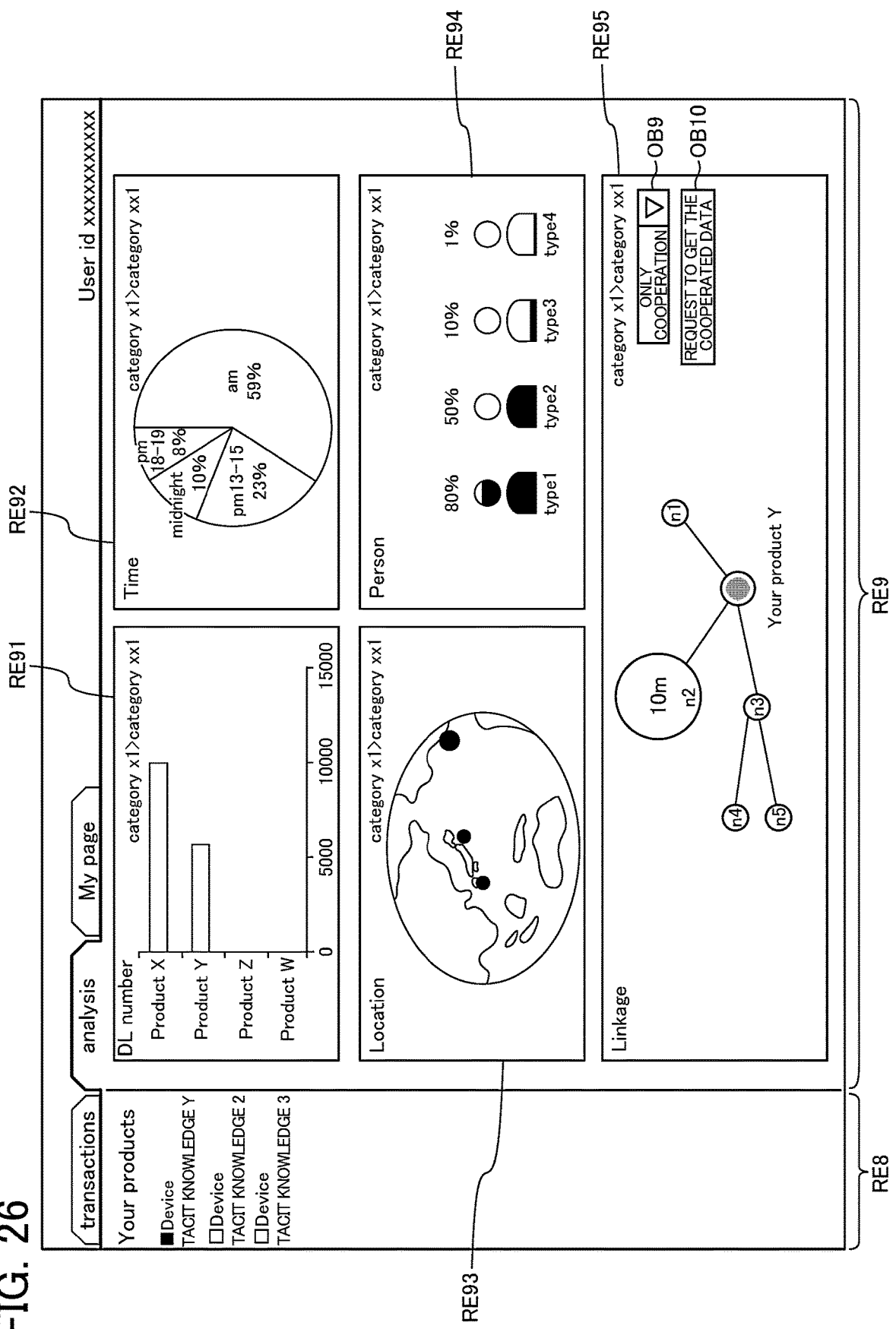
FIG. 26 shows a screen example for developers displayed on a developer's third terminal device.

The FIG. 26 is a screen example for the developer. The FIG. 26 includes an area RE8 for selecting the tacit knowledge product to be viewed and an area RE9 for displaying detailed information of the tacit knowledge product selected in the area RE8.

As shown in FIG. 26, for example, a list of tacit knowledge products created by the target developer and objects (e.g., radio buttons and checkboxes) for selecting one of the tacit knowledge products are displayed in the area RE8. If the processing unit 110 receive a selection operation of one of the tacit knowledge products, the processing unit 110 displays the detailed information about the selected tacit knowledge product in the area RE9.

In addition, the area RE9 includes an area RE91 indicating the number of sales (number of downloads), an area RE92 indicating the time zone of using the tacit knowledge products, an area RE93 indicating the region of using the tacit knowledge products, an area RE94 to display the patient attributes, and an area RE95 to display of other companies' products to be used together.

The information comparing the number of sales of the tacit knowledge product selected in the area RE8 with other tacit knowledge products that are the user's products is displayed in the area RE91. In the example of FIG. 26, the vertical axis represents the tacit knowledge products that are the user's products and the horizontal axis represents the number of sales or the number of downloads. The information of the tacit knowledge product selected in the area RE8 may be highlighted and displayed in comparison with the information of other tacit knowledge products. With the information shown in the area RE91, it is possible to make the developer understand the sales status of the user's products (the products of the company).

The time zone in which the tacit knowledge product selected in the area RE8 is used is displayed in the area RE92. As described above in relation to FIG. 21, each tacit knowledge product can transmit the information about the usage status to the server system 100. Therefore, the processing unit 110 may perform processing to specify the time zone in which the tacit knowledge products are used based on the information of the usage status from the tacit knowledge product and display the statistical information in the area RE91. In the case of the example corresponding to FIG. 26, the user can understand that the tacit knowledge Y selected in the area RE8 is used most frequently in the morning, followed by 13:00 to 15:00, midnight, and 18:00 to 19:00 based on a circle graph representing the usage ratio for each time zone.

The information about the country or region where the tacit knowledge product is used is displayed in the area RE93. For example, each tacit knowledge product is managed in association with the users (the patients and their families, hospitals, nursing homes, etc.) who use the tacit knowledge product. Therefore, by acquiring the address as the user attribute, the processing unit 110 can identify the place or the location where the tacit knowledge product is used. For example, a map information and an object representing the place or the location the tacit knowledge is used on the map information may be displayed in the area RE93. In addition, the display mode (the size, the color, or the shape, etc.) of the object may be changed or modified according to the number of uses, the number of sales, or the number of downloads. As mentioned above, if the telemedicine and the remote care are widely used by the caregivers such as the medical caregivers and the care assistants, the tacit knowledge may be also used all over the world. In this regard, by displaying the information shown in the area RE93, it is possible to present to developers in an easy-to-understand manner what kind of countries and regions their products will be used in.

In the area RE94, it is displayed what attributes of the users the tacit knowledge products selected in the area RE8 will be used for patients with. The attributes of the users may include various information such as sex, age, height, weight, medical history, medication history, ADL, etc., as described above. Four patient attributes type 1 to type 4 are displayed in the example of FIG. 26, and the ratio of the patients who use the tacit knowledge Y corresponding to each attribute is displayed. Note that the case where one patient has multiple attributes (corresponding to two or more of type 1 to type 4) is also considered. The FIG. 26 shows that 80% of patients who belong to the type 1 use the tacit knowledge Y, thereby such the tacit knowledge Y is more likely to be effective for patients with attributes corresponding to type 1.

The information indicating what kind of other products is associated with the tacit knowledge product selected in the area RE8 is displayed in the area RE95. It should be noted that the other products here includes the tacit knowledge products using the tacit knowledge in a narrow sense, but the other products are not limited to the tacit knowledge products. The other products may include applications and devices that do not use the tacit knowledge. It should be noted that the other products to be displayed may be those of other companies, but the other products are not limited to this, the other products may be its own products. Therefore the area RE95 can indicate the status of cooperation among its own products or multiple company's products.

The cooperation in this embodiment may include a cooperation case in which one result which one tacit knowledge application or one tacit knowledge device outputs affects another tacit knowledge application or another tacit knowledge device (for example, one output from one tacit knowledge application or one tacit knowledge device is used as the input of another tacit knowledge application or another tacit knowledge device), or a cooperation case in which two products are used at the same time but no data is transmitted or received. The cooperation in this embodiment may broadly include a cooperation case in which the same user uses two products (for example, each product is used at a different time).

For example, the processing unit 110 may receive the user input to select the cooperation case using an object such as the pull-down menu OB9. Then, the processing unit 110 may perform processing to select and display the tacit knowledge products that cooperate with the tacit knowledge Y in the selected cooperation case based on the usage status of each tacit knowledge product. For example, in the case that the output from one tacit knowledge application or one tacit knowledge device is used for the input of another tacit knowledge application or another tacit knowledge device, the software of the tacit knowledge application or the tacit knowledge device 400 needs to have a function for performing the cooperation. Therefore, the storage unit 120 may store the information including for example, the version of each tacit knowledge product and the function that the each version has, and the processing unit 110 may specify the cooperation mode based on the information. Whether or not a plurality of products are used at the same time can be determined from the usage status of each tacit knowledge product.

For example, each tacit knowledge product is shown as a node, and a line connecting two nodes may be displayed by a link (edge) in the area RE95 so as to indicate that the tacit knowledge products corresponding to two connected nodes has the cooperation relationship. Also, the nodes corresponding to the tacit knowledge products selected in the area RE8 may be highlighted. In the example of FIG. 26, the nodes n1 to n3 are connected to the nodes corresponding to the tacit knowledge product Y selected in the area RE8. This makes it easy to present to developers that the tacit knowledge products corresponding to the nodes n1 to n3 respectively cooperate together with the tacit knowledge product Y.

Here, the display mode or display method of each node or of each line corresponding to the connection may be changed or modified according to the number of times the tacit knowledge product corresponding to the node is cooperated with other tacit knowledge products. In the example of FIG. 26, the number of times the tacit knowledge product Y and the tacit knowledge corresponding to the node n2 are cooperated is 10 M (million) times, which is larger than the number of times the tacit knowledge products corresponding to the nodes n1 and n3 is cooperated, so the node n2 is displayed relatively larger.

Also, the tacit knowledge product displayed in the area RE95 is not limited to the tacit knowledge product directly cooperated with the tacit knowledge product Y (a primary cooperation), but may include the tacit knowledge product (secondary cooperation) cooperating with the tacit knowledge product having the primary cooperation for the tacit knowledge product Y. In the example of FIG. 26, the processing unit 110 determines that the number of cooperation between the tacit knowledge product corresponding to the node n3 and the prescribed tacit knowledge product "a" is equal to or greater than a predetermined threshold based on the usage status of each tacit knowledge product. Similarly, the processing unit 110 determines that the number of cooperation between the tacit knowledge product corresponding to the node n3 and another tacit knowledge product "b" is equal to or greater than the predetermined threshold. In this case, the processing unit 110 may perform processing to display the node n4 corresponding to the tacit knowledge "a" and the node n5 corresponding to the tacit knowledge "b" in the area RE95. For example, the nodes n4 and n5 are connected to the node n3 by a link of line. In this way, it is possible to present the information of the tacit knowledge product indirectly cooperated with the tacit knowledge product Y to the developer in an easy-to-understand manner.

Also, the information displayed in the area RE9 of the developer screen is not limited to the above examples. The FIGS. 27A to 27D are other examples of the detailed information of the tacit knowledge products displayed in the area RE9.

Figure 27A:
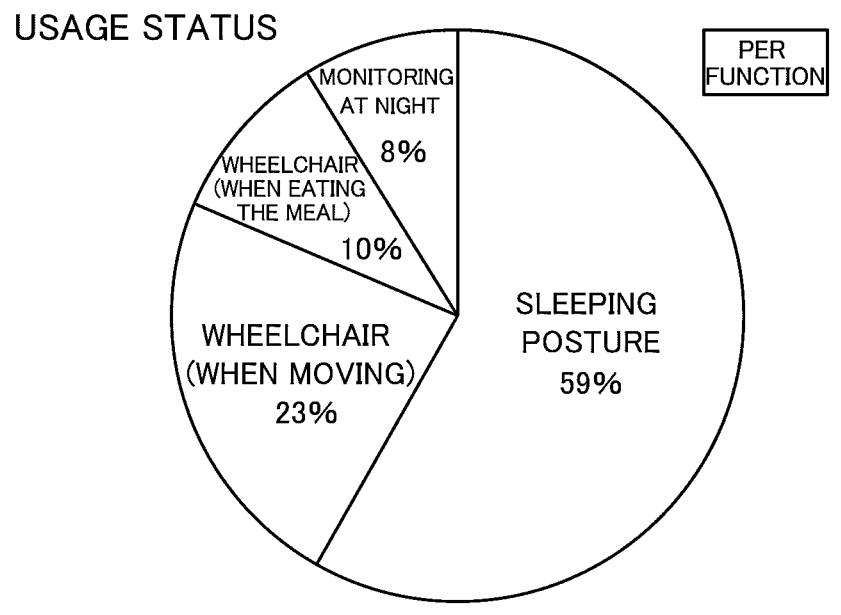
FIG. 27A shows another example of information displayed on a developer screen.

The FIG. 27A indicates the information representing the usage of the tacit knowledge and the purpose of using the tacit knowledge. For example, the processing unit 110 may display a pie chart representing the usage ratio for each purpose in the area RE9. The purpose of using the tacit knowledge may be entered by the caregivers, for example, when the medical caregivers or the care assistants select that tacit knowledge product as a response to a risk, or the purpose of using the tacit knowledge may be entered by a patient or the like who uses the tacit knowledge product. For example, the purpose of using the positioning application may be a purpose to determine whether the posture or the position of the patient is appropriate or not when the patient is lying in the bed or the like, a purpose to determine whether the posture or the position of the patient is appropriate or not when the patient is sitting in the wheelchair 630, a purpose to determine whether the posture or the position of the patient is appropriate or not when the patient is eating in the wheelchair 630, or a purpose to monitor at night (Prevention of falling from the beds, prevention of falling when the patients is awaken and starts moving, etc.). In the example of FIG. 27A, the ratio of tacit knowledge Y used for the purpose of determining whether the posture or the position of the patient is appropriate or not when the patient is lying in the bed is relatively high, and followed by the purpose to determine whether the posture or the position of the patient is appropriate or not when the patient is sitting in the wheelchair 630, the purpose to determine whether the posture or the position of the patient is appropriate or not when the patient is eating in the wheelchair 630, and the purpose to monitor at night in that order. The usage of the tacit knowledge may be determined from the functions rather than the purposes. For example, a button of "per function" is displayed in FIG. 27A, and if the caregivers select the button of "per function" that is, the terminal device receive the selection input using the button of "pre function", the processing to move to a screen showing the usage ratio by function may be performed.

Figure 27B:
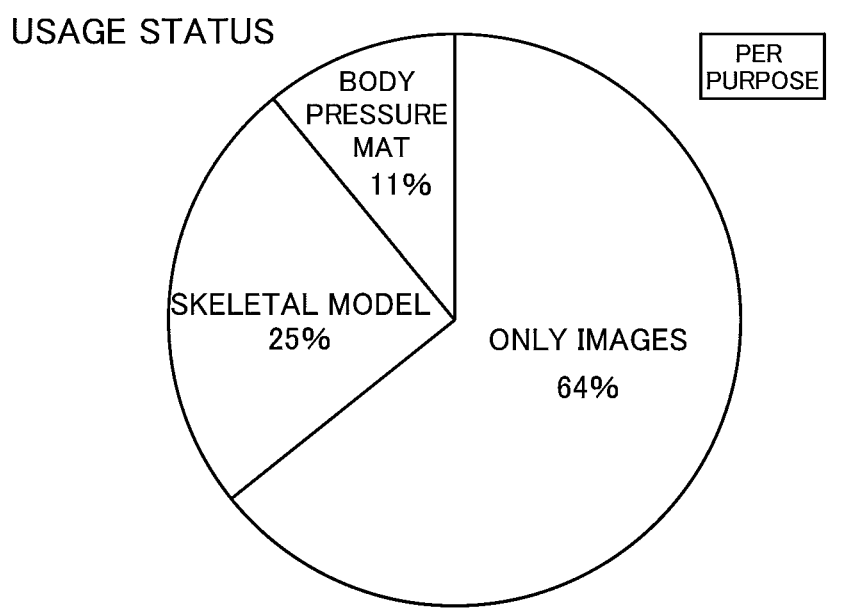
FIG. 27B shows another example of information displayed on a developer screen.

The FIG. 27B indicates the information showing the usage ratio by function of the tacit knowledge. For example, the processing unit 110 may display a pie chart showing the usage ratio for each function in the area RE9. Here, the function may indicate the information representing the input data that can be accepted when the processing is performed by the tacit knowledge, for example, or the information representing the output data that can be output by processing according to the tacit knowledge. In the example of FIG. 27B, three functions are shown as the examples: the function of using only images to determine whether the posture or the position of the patient is appropriate or not, the function of using the pressure value from the body pressure mat to determine whether the posture or the position of the patient is appropriate or not, and the function of acquiring a skeletal model in the image processing to determine whether the posture or the position of the patient is appropriate or not. In addition, a button of "per purpose" is shown in FIG. 27B, and if the caregivers select the button of the "pre purpose", that is, the terminal device receive the selection input using the button of "pre purpose", the processing to move to the screen shown in FIG. 27A may be performed.

Figures 27C, 27D:
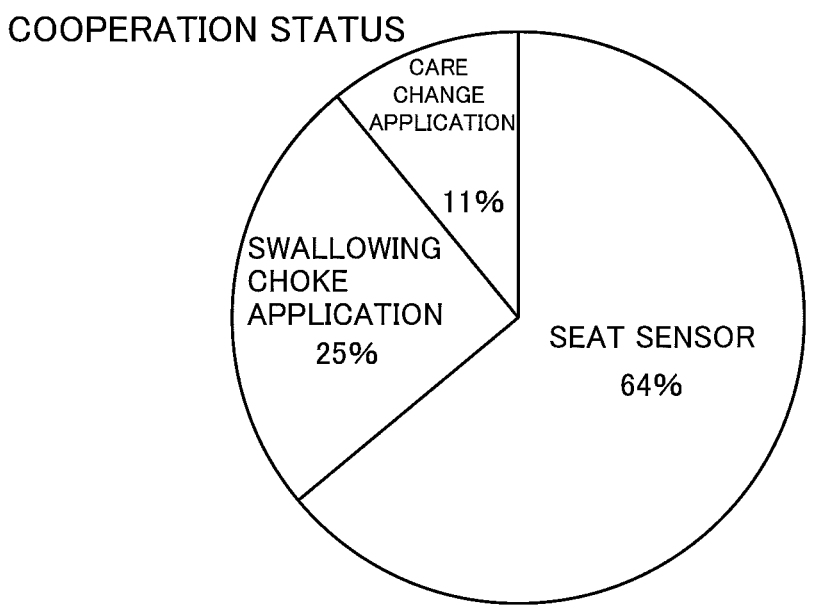
FIG. 27C shows another example of information displayed on a developer screen.
FIG. 27D shows another example of information displayed on a developer screen.

The cooperated tacit knowledge is specifically displayed in the area RE95 of FIG. 26, but in this embodiment, the statistical information of the cooperated tacit knowledge may be displayed. The FIG. 27C is an example of the statistical information of the cooperate status what kinds of tacit knowledge products are cooperated. For example, the processing unit 110 may display a pie chart representing the cooperation ratio for each type of device or application in the area RE9.

In the example of FIG. 27C, the statistical information shows that 64% of the total number of cooperation in which tacit knowledge Y worked together, were the cooperation with the seat sensor 440, 25% of the total number of cooperation were the cooperation with the swallowing choke application, and 11% of the total number of cooperation were the cooperation with the care change application. In this way, it is easy to present to the developer what kind of tacit knowledge product works with the selected tacit knowledge in area RE8.

In addition, if the caregivers select any kind of tacit knowledge product in FIG. 27C, detailed information on cooperating with the selected tacit knowledge product may be displayed. The FIG. 27D is an example of the information to be displayed if, for example, the caregivers select the seat sensor 440 in FIG. 27C. In FIG. 27D, a pie chart representing the ratio of functions used by the seat sensor 440 may be displayed if, for example, the tacit knowledge product Y and the seat sensor 440 are cooperated. For example, if the seat sensor 440 has a function to determine whether the patient loses his or her posture or position (determination whether the posture or the position of the patient shifts to forward or sideways), a notification function of body movement level, and a notification function indicating that the posture or the position of the patient is updated or changed, the information representing which function is used when the seat sensor 440 is used with the tacit knowledge Y is displayed. In the example of FIG. 27D, if the seat sensor 440 is used with the tacit knowledge Y, the function to determine whether the patient loses his or her posture or position is mostly used, followed by the notification function of body movement level, and the notification function indicating that the position or the position of the patient is updated or changed in that order. Since it is considered that the statistical information shown in FIG. 27D does not include the personal information, even if the seat sensor 440 is manufactured by another company, the process of acquiring the user's consent described later may be omitted. Alternatively, if the seat sensor 440 is manufactured by another company, the information shown in FIG. 27D may be displayed for only the data with the user's consent. In addition, although FIG. 27D illustrated the usage status of the seat sensor 440 by function when the seat sensor 440 cooperates with the tacit knowledge Y, the usage status of the tacit knowledge Y by function when the tacit knowledge Y cooperates with the seat sensor 440 may be displayed, and various modifications can be made to the information to be displayed.

4.2 Request to Acquire Data from the Cooperated Tacit Knowledge Product

As shown in the area RE95 in FIG. 26, the information about other companies' products that are cooperated with their own products may be displayed in the developer screen. In this case, the developer can accurately analyze the patient's condition, the effectiveness of the own tacit knowledge products, and the functions required for the tacit knowledge product, etc., by correlating the data from the own tacit knowledge products with the data from other companies' products. Since the server system 100 may collect the information about each tacit knowledge product, the above developer can get the information acquired by the other's companies tacit knowledge products which are different from the above developers. However, there is a high probability that the data of the applications or the devices used by the target patients will become personal information of the target patients. And we can assume that the target patients and concerned person such as the family member of the target patient may have licensed the data acquired by the tacit knowledge device to the developers who made the tacit knowledge products such as the applications or the devices, but not to the other developers other than that developer. Therefore, it is not desirable to supply the data acquired by the tacit knowledge applications and tacit knowledge devices 400 to the other developers other than that developer without the consent of the patients or the concerned person, etc.

Therefore, the server system 100 of this embodiment perform processing to get the consent from the users such as the patients thorough the cooperated tacit knowledge product, if the server system 100 receives a request from a prescribed developer to get the data acquired from products cooperated with its own product. Hereafter, the product that cooperates with the tacit knowledge product of the prescribed developer is denoted as the cooperated product, and the data related to the cooperated product is denoted as the cooperated data. For example, if the processing unit 110 receiving a request to acquire the cooperated data from the third terminal device 200C, the processing unit 110 may output the information to encourage or prompt the user using the cooperated product to input whether or not to approve the data acquisition. In this way, since the server system 100 performs processing to get the consent of the patients or the concerned person, the developer does not need to request the consent individually, thus improving the convenience to collect the data acquired from the products of the third party.

Figure 28:
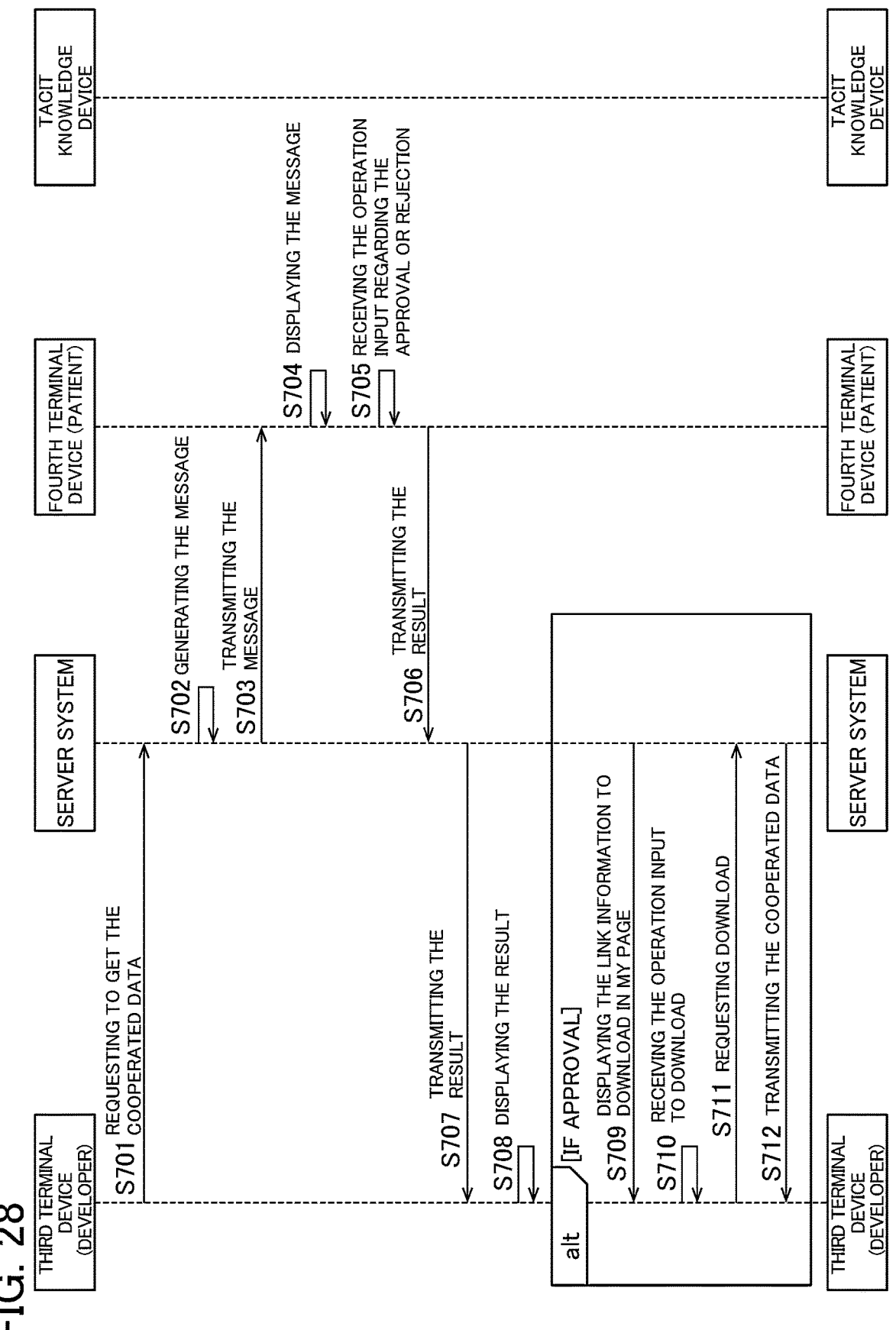
FIG. 28 shows a sequence diagram illustrating the sharing processing of linked data.

The FIG. 28 is a sequence diagram illustrating the processing related to the request to get the data. Firstly, the third terminal device 200C transmits a request to get the cooperated data to the server system 100 in the step S701. For example, the third terminal device 200C will perform processing of the step S701 if the third terminal device 200C receives the selection input using the object OB10 representing the request to get the cooperated data in the area RE95 of FIG. 26. If the multiple cooperated products are displayed in the area RE95, the developer can select at least one of the multiple cooperated products, and the information representing the selected result by the developer may be transmitted to the server system 100 in the step S701.

In the step S702, the processing unit 110 of the server system 100 generates a message for the patient by performing processing to identify the cooperated products related to data the developer has requested and performing processing to identify the patient using the developer's tacit knowledge product and the corresponding tacit knowledge product in a coordinated manner. Here, the message is addressed to the fourth terminal device 200D corresponding to the identified patient, and includes some questions whether or not to approve the request to acquire the cooperated data on the cooperated product and to transmit the cooperated data to that developer. In the step S703, the processing unit 110 transmits the message to the fourth terminal device 200D via the communication unit 130.

In the step S704, the fourth terminal device 200D inquires whether the patient or the concerned person agrees with or approves data acquisition by displaying the received message. In the step S705, the fourth terminal device 200D receives the operation input regarding the approval or rejection by the patient or the like from the display unit of the fourth terminal device 200D. In the step S706, the fourth terminal device 200D transmits the operation input to the server system 100.

In the step S707, the server system 100 transmits the operation input transmitted from the fourth terminal device 200D to the third terminal device 200C that is the source of the request to acquire the cooperated data. In the step S708, the processing unit 210 of the third terminal device 200C may display the result whether the patient or the concern person agree with or approve the request or not on the display unit 240.

If the server system 100 receives the user's approval from the fourth terminal device 200D, the processing unit 110 may perform processing to output the information about other tacit knowledge products (the cooperated data related to the cooperated product) to the third terminal device 200C. For example, since the storage unit 120 of the server system 100 also collects the data from the cooperated products as described above, the storage unit 120 also stores the cooperated data. Therefore, the processing unit 110 may read the cooperated data from the storage unit 120 and provide the cooperated data to the third terminal device 200C.

For example, as shown in the step S709 in FIG. 28, if the server system 100 receives the user's approval from the fourth terminal device 200D, the processing unit 110 performs processing to display the link information to download the cooperated data on the screen in the third terminal device 200C (for example, the screen of "My Page" displayed after login).

In the step S710, the third terminal device 200C receives the download operation from the developer based on the link information. In the step S711, the third terminal device 200C sends a download request to the server system 100. In the step S712, the processing unit 110 sends the cooperated data to the third terminal device 200C based on the request. In this way, it is possible to properly perform processing to transmit and receive the cooperated data between the server system 100 and the third terminal device 200C if the server system 100 receives the user's approval.

The user's approval or the user's rejection for the request is determined for each user such as the patient or the concern person. Therefore, the third terminal device 200C receives the cooperated data of the users who have approved the request and does not receive the cooperated data of the users who have rejected the request. For example, we assumed that the cooperation is performed 10 M (million) times, and the server system 100 receives the user's approval for 1 M times of the cooperation. In this case, the server system 100 transmits the cooperated data for 1 M times to the third terminal device 200C from the cooperated data for 10 M times, and does not transmit the remaining cooperated data for 9 M times.

The server system 100 may manage the data of each tacit knowledge product separately as summary data which is neither secret information nor personal information, and as detail data which includes secret information or personal information. In this case, a range which the user can input whether or not to approve or reject the request may be limited to only the summary data. Alternatively, the user may be able to individually set whether or not to approve or reject the request for each of Summary data and detail data. Furthermore various modifications can be made to the content of data provided to the third terminal device 200C.

However, the information on other tacit knowledge products is not limited to those transmitted from the server system 100. For example, each tacit knowledge product can naturally acquire the information on the tacit knowledge product itself. Therefore, the information on the other tacit knowledge product may be directly transmitted from the other tacit knowledge product to the third terminal device 200C.

Figure 29:
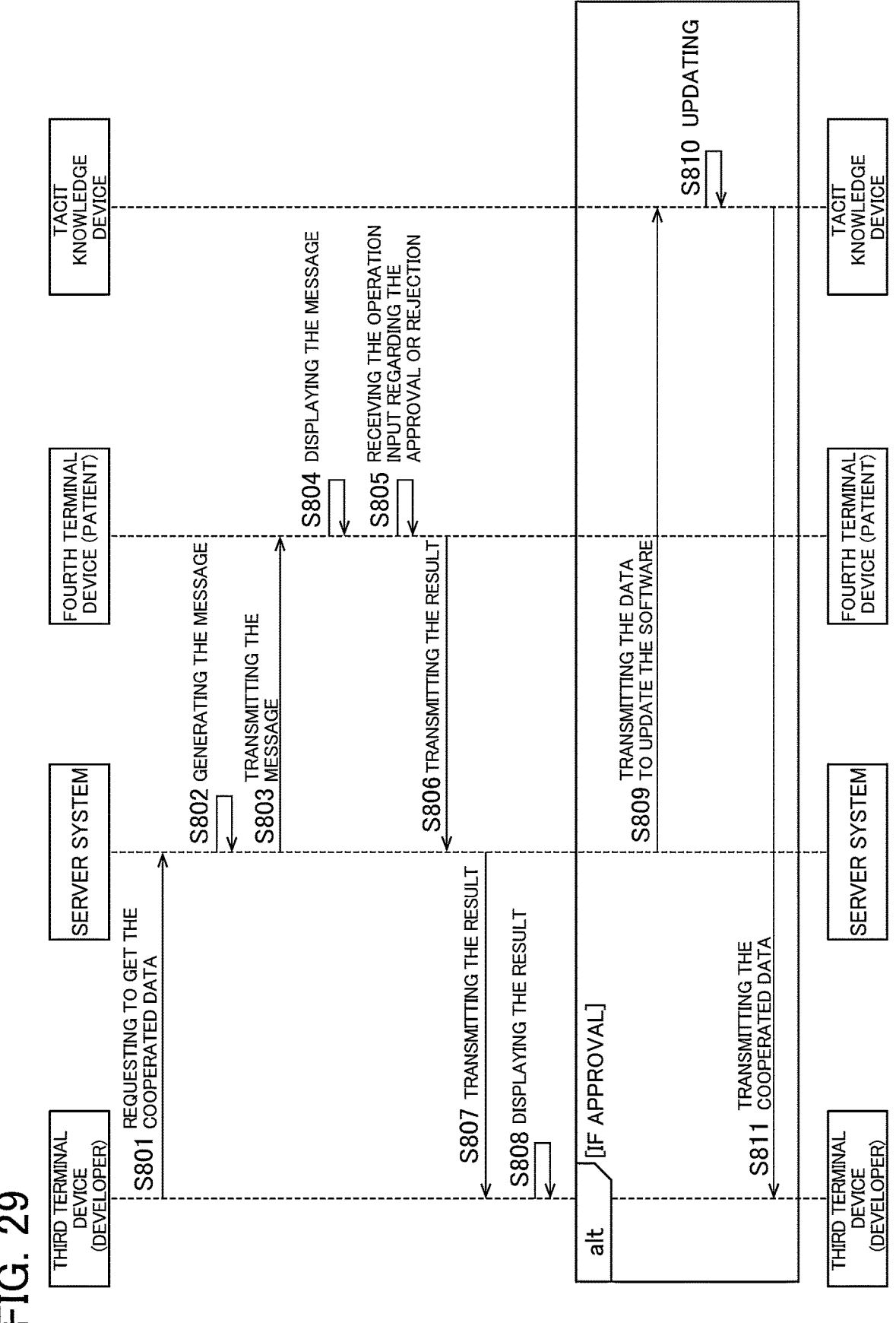
FIG. 29 shows a sequence diagram illustrating the sharing processing of linked data.

The FIG. 29 is another sequence diagram illustrating the processing on the request. Since the steps S801 to S808 in FIG. 29 are substantially similar to the steps S701 to S708 in FIG. 28, a detailed explanation is omitted.

The processing unit 110 of the server system 100 may perform processing to provide update data to transmit the data from other tacit knowledge products to the third terminal device 200C if the server system 100 receives the user's approval. In this way, it becomes possible to transmit the information from other company's tacit knowledge products to the developer's third terminal device 200C without going through the server system 100.

For example, in the case that the tacit knowledge product is the tacit knowledge device 400, the processing unit 110 transmits the update data to update the software of the tacit knowledge device 400, as shown in the step S809 in FIG. 29. For example, the update data includes connection information (e.g., IP address, etc.) to communicate between the third terminal device 200C and the tacit knowledge device 400, and an algorithm to transmit the data to the third terminal device 200C based on the connection information.

In the step S810, the tacit knowledge device 400 may perform processing to update the software which has already installed based on the update data. In the step S811, the tacit knowledge device 400 may perform processing to transmit data (the cooperated data) related to the tacit knowledge device 400 to the third terminal device 200C using the function add by processing of the step S810. In this way, it is possible to properly perform processing to transmit and receive the cooperated data without going through the server system 100 if the tacit knowledge device 400 receives the user's approval.

In the above example, we have described the cases to require the cooperated data on the tacit knowledge product that directly cooperates (or primarily links) with the company's products, the cases are not limited to this. For example, the third terminal device 200C may request the cooperated data on the tacit knowledge product that cooperates (or secondarily links) to the tacit knowledge product that cooperates directly with its products. For example, the tacit knowledge product corresponding to nodes n4 and n5 shown in the area RE95 in FIG. 26 is tacit knowledge that cooperates secondarily with the tacit knowledge product Y (the product Y).

For example, if the processing unit 110 receives the request to acquire the cooperated data on the tacit knowledge products that cooperates secondarily from the third terminal device 200C, the processing unit 110 may perform processing shown in FIGS. 28 and 29 for the target patient who is using a first tacit knowledge product of the developer corresponding to the third terminal device 200C and who is using the tacit knowledge products that cooperate secondarily with the first tacit knowledge product. In this way, it is possible to provide the cooperated data about the tacit knowledge product that cooperates secondarily to the developer. In addition, it may be possible to request the cooperated data related to the tacit knowledge that is cooperated with the tacit knowledge that is linked by secondary linkage, and various modifications can be made to the range of the requests.

Although the present embodiment has been described in detail as described above, it will be easy for those skilled in the art to understand that many modifications are possible that do not materially deviate from the novel matters and effects of the present embodiment. Therefore, all such modifications are to be included in the scope of this disclosure. For example, a term appearing at least once in the description or drawings together with a different term that is broader or synonymous may be replaced by that different term anywhere in the description or drawings. All combinations of this embodiment and variations are also included in the scope of this disclosure. Also, the configuration and operation of information processing devices, information processing systems, server systems, terminal devices, etc. are not limited to those described in this embodiment, and various variations can be implemented.

Although the present embodiment has been described in detail as described above, a person skilled in the art will readily understand that many modifications can be made that do not materially deviate from the novel matters and effects of the present embodiment. Therefore, all such variations shall be included in the scope of this disclosure. For example, a term appearing at least once in a description or drawing with a different term that is broader or synonymous may be replaced by that different term anywhere in the description or drawing. All combinations of the present embodiment and variations are also included in the scope of this disclosure. Also, the configuration and operation of the information processing device and the information processing method, etc. are not limited to those described in this embodiment, and various modifications can be performed.

What is claimed is:

1. An information processing device comprising:
a communicator configured to communicate with a first terminal device and a second terminal device, the first terminal device being held by a medical caregiver, the second terminal device being held by a care assistant; and
a processor configured to acquire a medical information and a care assistance information, the medical information including a first method how to deal with a diagnosis of a patient taken by the medical caregiver, the care assistance including a second method how to deal with a status of the patient taken by the care assistant through the communicator, wherein
the processor is configured to provide the medical information and the care assistance information in association with the patient on the first terminal device and the second terminal device,
the processor is configured to generate a medication status of the patient for display on the first terminal device or second terminal device, wherein the medication status is based on the medical information and the care assistance information,
the processor is configured to control an operating mode of a detection device to initiate a meal assistance procedure, based on the generated medication status of the patient,
the detection device comprises a microphone to capture audio data of the patient or an imaging device to capture an image of the patient, the processor is configured to control the detection device to initiate the meal assistance procedure, based on the captured audio data of the patient or the captured image of the patient, wherein in the meal assistance procedure, the detection device is controlled to determine whether the patient is choking based on the captured audio data or monitor whether the patient is consuming a meal based on the captured image, and wherein the medical information is set by a first authorization and the care assistance information is set by a second authorization, the first authorization being different from the second authorization.

2. The information processing device according to the claim 1, wherein the processor is configured to provide information indicating a request has been received to the second terminal device if the processor receives the request to reconsider the care assistance information associated with the patient from the first terminal device.

3. The information processing device according to the claim 2, wherein the processor is configured to acquire the care assistance information from the second terminal device, the care assistance information including information digitizing a first tacit knowledge of the care assistant, and the processor is configured to provide information to encourage the care assistant to update or change the first tacit knowledge to the second terminal device if the processor receives the request to reconsider the care assistance information associated with the patient from the first terminal device.

4. The information processing device according to the claim 1, wherein the processor is configured to provide information indicating a request has been received to the first terminal device if the processor receives the request to reconsider the medical information associated with the patient from the second terminal device.

5. The information processing device according to the claim 4, wherein the processor is configured to acquire the medical information from the first terminal device, the medical information including information digitizing a second tacit knowledge of the medical caregiver, and the processor is configured to provide information to encourage the medical caregiver to update or change the second tacit knowledge to the first terminal device if the processor receives the request to reconsider the medical information associated with the patient from the second terminal device.

6. The information processing device according to the claim 1, wherein the processor is configured to acquire the medical information and the care assistance information, the care assistance information including information digitizing a first tacit knowledge of the care assistant, the medical information including information digitizing a second tacit knowledge of the medical caregiver.

7. The information processing device according to the claim 6, wherein the processor is configured to acquire information indicating an usage status of the first tacit knowledge or the second tacit knowledge from a tacit knowledge application or a tacit knowledge device, the tacit knowledge application being an application software corresponding to the first or second tacit knowledge, the tacit knowledge device being configured to perform processing corresponding to the first or second tacit knowledge, and the processor is configured to provide the information indicating the usage status of the first tacit knowledge or the second tacit knowledge on the first terminal device or the second terminal device.

8. The information processing device according to the claim 6, wherein the processor is configured to perform processing to make the medical caregiver or the care assistant experience the first or second tacit knowledge in the virtual reality space if the processor receives a request to the experience of the first or second tacit knowledge in a screen of the first terminal device or the second terminal device.

9. The information processing device according to the claim 6, wherein the communicator is configured to communicate with a third terminal device, the third terminal device being used by a developer who creates at least one of a first tacit knowledge application or a first tacit knowledge device, the first tacit knowledge application being an application software corresponding to the first or second tacit knowledge, the first tacit knowledge device being configured to perform processing corresponding to the first or second tacit knowledge, and the processor is configured to provide information about a second tacit knowledge application or a second tacit knowledge device which cooperates with the first tacit knowledge application or the first tacit knowledge device, the second tacit knowledge application being different from the first tacit knowledge application, and the second tacit knowledge device being different from the first tacit knowledge device.

10. The information processing device according to the claim 7, wherein the communicator is configured to communicate with a third terminal device, the third terminal device being used by a developer who creates at least one of a first tacit knowledge application or a first tacit knowledge device, the first tacit knowledge application being an application software corresponding to the first or second tacit knowledge, the first tacit knowledge device being configured to perform processing corresponding to the first or second tacit knowledge, and the processor is configured to provide information about a second tacit knowledge application or a second tacit knowledge device which cooperates with the first tacit knowledge application or the first tacit knowledge device, the second tacit knowledge application being different from the first tacit knowledge application, and the second tacit knowledge device being different from the first tacit knowledge device.

11. The information processing device according to the claim 9, wherein the processor is configured to output information to encourage the patient or concern person of the patient to input whether or not to approve to acquire data and to transmit the data to the developer if the processor receives a request to acquire the data using other tacit knowledge application or other tacit knowledge device from the third terminal device.

12. The information processing device according to the claim 10, wherein the processor is configured to output information to encourage the patient or concern person of the patient to input whether or not to approve to acquire data and to transmit the data to the developer if the processor receives a request to acquire the data using other tacit knowledge application or other tacit knowledge device from the third terminal device.

13. The information processing device according to the claim 11, wherein the processor is configured to perform processing to output information about the other tacit knowledge application or the other tacit knowledge device to the third terminal device or to update a software to transmit data from other tacit knowledge application or the other tacit knowledge device to the third terminal device if the processor receives an approval to acquire the data.

14. The information processing device according to the claim 12, wherein the processor is configured to perform processing to output information about the other tacit knowledge application or the other tacit knowledge device to the third terminal device or to update a software to transmit data from other tacit knowledge application or the other tacit knowledge device to the third terminal device if the processor receives an approval to acquire the data.

15. The information processing device according to the claim 1, wherein the communicator is configured to receive image data of the patient and audio data for detecting whether the patient is swallowing, and the processor is configured to perform processing to acquire determination result on a medication status of the patient based on the image data and the audio data and perform processing to provide the determination result of the patient in association with the medical information and the care assistance information in the first and second terminal device.

16. The information processing device according to the claim 14, wherein the communicator is configured to receive image data of the patient and audio data for detecting whether the patient is swallowing, and

the processor is configured to perform processing to acquire determination result on a medication status of the patient based on the image data and the audio data and perform processing to provide the determination result of the patient in association with the medical information and the care assistance information in the first and second terminal device.

17. An information processing method comprising:

acquiring a medical information from a first terminal device, the medical information including a first method how to deal with a diagnosis of a patient taken by a medical caregiver;

acquiring a care assistance information from a second terminal device, the care assistance information including a second method how to deal with a status of the patient taken by the care assistant;

providing the medical information and the care assistance information in association with the patient on the first terminal device and the second terminal device;

generating a medication status of the patient for display on the first terminal device or second terminal device, wherein the medication status is based on the medical information and the care assistance information; and controlling an operating mode of a detection device to initiate a meal assistance procedure, based on the generated medication status of the patient, wherein the detection device comprises a microphone to capture audio data of the patient or an imaging device to capture an image of the patient, and the information processing method further comprises controlling the detection device to initiate the meal assistance procedure, based on the captured audio data of the patient or the captured image of the patient, wherein in the meal assistance procedure, the method further comprises determining whether the patient is choking based on the captured audio data or monitoring whether the patient is consuming a meal based on the captured image.

* * * * *